United States Patent
Anderson et al.

(10) Patent No.: US 7,144,569 B1
(45) Date of Patent: Dec. 5, 2006

(54) DIAGNOSIS OF COELIAC DISEASE USING A GLIADIN EPITOPE

(75) Inventors: Robert Paul Anderson, Headington (GB); Adrian Vivian Sinton Hill, Oxford (GB); Derek Parry Jewell, Oxford (GB)

(73) Assignee: ISIS Innovation Limited, Oxford (GB)

( * ) Notice: Subject to any disclaimer, the term of this patent is extended or adjusted under 35 U.S.C. 154(b) by 91 days.

(21) Appl. No.: 10/089,700

(22) PCT Filed: Oct. 2, 2000

(86) PCT No.: PCT/GB00/03760

§ 371 (c)(1), (2), (4) Date: Jan. 9, 2003

(87) PCT Pub. No.: WO01/25793

PCT Pub. Date: Apr. 12, 2001

(30) Foreign Application Priority Data

Oct. 1, 1999 (GB) ................................ 9923306.6

(51) Int. Cl.
- A61K 39/35 (2006.01)
- C07K 7/04 (2006.01)
- G01N 33/53 (2006.01)

(52) U.S. Cl. ................. 424/9.81; 424/185.1; 435/7.24; 435/7.94; 435/7.95; 435/975; 514/2; 514/12; 514/13; 514/14; 514/15; 514/16; 530/324; 530/325; 530/326; 530/327; 530/328; 530/329; 530/372; 530/374; 530/402

(58) Field of Classification Search ................ 424/9.81, 424/185.1; 435/7.24, 7.94, 7.95, 975; 514/5, 514/12–16; 530/324–329, 372, 374, 402
See application file for complete search history.

(56) References Cited

U.S. PATENT DOCUMENTS

| | | |
|---|---|---|
| 4,459,355 A | 7/1984 | Cello et al. |
| 4,536,475 A | 8/1985 | Anderson |
| 4,945,050 A | 7/1990 | Sanford et al. |
| 5,036,006 A | 7/1991 | Sanford et al. |
| 5,100,792 A | 3/1992 | Sanford et al. |
| 5,177,010 A | 1/1993 | Goldman et al. |
| 5,179,022 A | 1/1993 | Sanford et al. |
| 5,187,073 A | 2/1993 | Goldman et al. |
| 5,204,253 A | 4/1993 | Sanford et al. |
| 5,371,014 A | 12/1994 | Matsuyama et al. |
| 5,405,765 A | 4/1995 | Vasil et al. |
| 5,464,763 A | 11/1995 | Schilperoort et al. |
| 5,478,744 A | 12/1995 | Sanford et al. |
| 5,484,956 A | 1/1996 | Lundquist et al. |
| 5,489,520 A | 2/1996 | Adams et al. |
| 5,508,468 A | 4/1996 | Lundquist et al. |
| 5,510,318 A | 4/1996 | Patel et al. |
| 5,538,877 A | 7/1996 | Lundquist et al. |
| 5,554,798 A | 9/1996 | Lundquist et al. |
| 5,565,346 A | 10/1996 | Facciotti |

FOREIGN PATENT DOCUMENTS

| | | |
|---|---|---|
| EP | 0242236 | 10/1987 |
| EP | 0255378 | 2/1988 |
| EP | 0293358 | 11/1988 |
| EP | 442174 | 8/1991 |
| EP | 486233 | 5/1992 |
| EP | 486234 | 5/1992 |
| EP | 604662 | 7/1994 |
| EP | 672752 | 9/1995 |
| EP | 0693119 | 1/1997 |
| EP | 0 905 518 A1 | 3/1999 |
| EP | 539563 | 10/2001 |
| WO | WO 91/02071 | 2/1991 |
| WO | WO 92/000377 | 1/1992 |
| WO | WO 92/17580 | 10/1992 |
| WO | WO 92/20809 | 11/1992 |
| WO | WO 94/13863 | 6/1994 |
| WO | WO 95/06128 | 3/1995 |
| WO | WO 98/23960 | 6/1998 |

(Continued)

OTHER PUBLICATIONS

Godkin, A.S. et al. Identification of a Coeliac Disease-Specific T Cell Epitope from A-Gliadin; *Gut*; vol. 44, suppl. p. A72, Apr. 1999.*

(Continued)

*Primary Examiner*—David Saunders
(74) *Attorney, Agent, or Firm*—Cozen O'Connor, P.C.

(57) ABSTRACT

A method of diagnosing coeliac disease, or susceptibility to coeliac disease, in an individual comprising: (a) contacting a sample from the host with an agent selected from (i) the epitope comprising sequence which is: SEQ ID NO: 1 or 2, or an equivalent sequence from a naturally occurring homologue of the gliadin represented by SEQ ID NO: 3, (ii) an epitope comprising sequence comprising: SEQ ID NO: 1, or an equivalent sequence from a naturally occurring homologue of the gliadin represented by SEQ ID NO: 3, which epitope is an isolated oligopeptide derived from a gliadin protein, (ii) an analogue of (i) or (ii) which is capable of being recognised by a T cell receptor that recognises (i) or (ii), which in the case of a peptide analogue is not more than 50 amino acids in length, or (iv) a product comprising two or more agents as defined in (i), (ii) or (iii), and (b) determining in vitro whether T cells in the sample recognises the agent; recognition by the T cells indicating that the individual has, or is susceptible to, coeliac disease. Therapeutic compositions which comprise the epitope and gliadin proteins which do not cause coeliac disease are also provided.

19 Claims, 39 Drawing Sheets

FOREIGN PATENT DOCUMENTS

| | | |
|---|---|---|
| WO | WO 98/45460 | 10/1998 |
| WO | WO 98/45461 | 10/1998 |
| WO | WO 99/20775 | 4/1999 |
| WO | WO 02/083722 | 10/2002 |
| WO | WO 03/066079 | 8/2003 |
| WO | WO 03/096984 | 11/2003 |
| WO | WO 03/104273 | 12/2003 |

OTHER PUBLICATIONS

Arentz-Hansen, Helene; The Intestinal T Cell Response to α-Gliadin in Adult Celiac Disease is Focused on a Single Deamidated Glutamine Targeted by Tissue Transglutaminase; *J. Exp. Med.* vol. 191, No. 4; Feb. 2000 603-612.

Anderson, Robert et al.; in vivo antigen challenge in celiac disease identifies a single transglutaminase-modified peptide as the dominant A-gliadin T-cell epitope; *Nature Medicine* vol. 6, No. 3, Mar. 2000; 337-342.

Uhlig, H. et al., Role of Tissue Transglutaminase in Gliadin Binding to Reticular Extracellular Matrix and Relation to Coeliac Disease Autoantibodies; *Autoimmunity*, vol. 28, pp. 185-195.

Database Swissprot Online! ID: GDA4-Wheat ACC:P04724, Aug. 13, 1987 (Abstract).

Okita, T. et al., Evolution and Heterogeneity of the α-1β-type and γ-type Gliadin DNA Sequences; *The Journal of Biological Chemistry*; vol. 260, No. 13, Jul. 5, 1985; pp. 8203-8213.

Troncone, R. et al. Cytokines produced by Gliadin-Specific T Cell Clones from the Coeliac Mucosa; *Gastroenterology*, vol. 110, No. 4, p. A103, Apr. 1996.

Van De Wal, Y et al., Small intestinal T cells of celiac disease patients recognize a natural pepsin fragment of gliadin; *Proc. Natl. Acad. Sci.* vol. 95, pp. 10050-10054, Aug. 1998; Immunology.

O'Keeffe, J. et al. T cell proliferation, MHC class II restriction and cytokine products of gliadin-stimulated peripheral blood mononuclear cells (PBMC); *Clin Exp. Immunol*; 1999; 117:269-276.

Altschul "A protein alignment scoring system sensitive at all evolutionary distances," *J Mol Evol* (1993) 36(3):290-300.

Altschul et al., "Basic local alignment search tool," *J Mol Biol* (1990) 215(3):403-410.

Bunce et al., "Phototyping:comprehensive DNA typing for HLA-A, B, C, DRB1, DRB3, DRB4, DRB5 & DQB1 by PCR with 144 primer mixes utilizing sequence-specific primers (PCR-SSP)," *Tissue Antigens* (1995) 46(5):355-367.

Dalta et al., "Plant promoters for transgene expression," *Biotechnology Ann Rev* (1997) 3:269-296.

Devereux et al., "A comprehensive set of sequence analysis programs for the VAX," *Nucleic Acids Research* (1984) 12(1 Pt 1):387-395.

Greenberg et al., "Transglutaminases: multifunctional cross-linking enzymes that stabilize tissues," *FASEB* (1991) 5(15):3071-3077.

Henikoff "Amino acid substitution matrices from protein blocks," *Proc. Natl. Acad Sci USA* (1992) 89(22):10915-10919.

Karlin et al., "Applications and statistics for multiple high-scoring segments in molecular sequences," *Proc Natl Acad USA* (1993) 90(12):5873-5887.

Kohler et al., "Continuous cultures of fused cells secreting antibody of predefined specificity," *Nature* (1975) 256(5517):495-497.

Kricka "Prospects for chemiluminescent and bioluminescent immunoassay and nucleic acid assays in food testing and the pharmaceutical industry," *J Biolumin Chemilumin* (1998) 13(4):189-193.

Lalvani et al., "Rapid effector function in CD8+ memory T cells," *J Exp Med* (1997) 186(6):859-865.

Mantzaris et al., "In vivo toxicity of a synthetic dodecapeptide from A gliadin in patients with coeliac disease," *Gastroenterol.* (1991) 26(4):392-398.

Maiuri et al., "In vitro activities of A-gliadin-related synthetic peptides: damaging effect on the atrophic coeliac mucosa and activation of mucosal immune response in the treated coeliac mucosa," *Scand J Gastroenterol.* (1996) 31(3):247-253.

Molberg et al., "Tissue transglutaminase selectively modifies gliadin peptides that are recognized by gut-derived T cells in celiac disease," *Nature Med* (1998) 4(6):713-717.

Mullighan et al., "High-resolution HLA-DQB1 typing using the polymerase chain reaction and sequence-specific primers," *Tissue Antigens* (1997) 50(6):688-692.

Olerup et al., "HLA-DQB1 and -DQA1 typing by PCR amplification with sequence-specific primers (PCR-SSP) in 2 hours," *Tissue Antigens* (1993) 41(3):119-137.

Ota et al., "T-cell recognition of an immunodominant myelin basic protein epitope in multiple sclerosis," *Nature* (1990) 346(6280):183-187.

Quarsten et al., "HLA binding and T cell recognition of a tissue transglutaminase-modified gliadin epitope," *Eur J Immunol* (1999) 29(8):2506-2514.

Thurau et al., "Oral tolerance in a murine model of relapsing experimental autoimmune uveoretinitis (EAU): induction of protective tolerance in primed animals," *Clin Exp Immunol* (1997) 109(2):370-376.

Vasil et al., "Herbicide Resistant Fertile Transgenic Wheat Plants Obtained by Microprojectile Bombardment of Regenerable Embryogenic Callus ," *Biotechnology* (1992) 10:667-674.

Weiner et al., "Oral tolerance: cytokine milieu in the gut and modulation of tolerance by cytokines," *Res Immunol* (1997) 148(8-9):528-533.

Yoshida et al., "The oral administration of low-dose antigen induces activation followed by tolerization, while high-dose antigen induces tolerance without activation," *Clin Immunol Immunopathol* (1997) 82:207-215.

Anderson "Identification of the Immunodominant T-Cell Epitope in Agliadin Recognized by Coeliac Disease (CD) Patients in Vivo," (1999) A165.

Dieterich et al., "Identification of tissue transglutaminase as the autoantigen of celiac disease," *Nature Medicine* (1997) 3(7):797-801.

Gutgemann et al., "Induction of rapid T cell activation and tolerance by systemic presentation of an orally administered antigen," *Immunity* (1998) 8:667-673.

McAdam et al., "Gliadin Specific Response by Small Intestinal T Cells," *Peptide Binding to HLA Molecules and T Cells*, Eighth International Symposium on Coeliac Disease, p. 17, (1999).

Sjostrom et al., "Identification of a gliadin T-cell epitope in coeliac disease: general importance of gliadin deamidation for intestinal T-cell recognition," *Scand J Immunol* (1998) 48(2):111-115.

Tian et al., "Antigen-based immunotherapy for autoimmune disease: from animal models to humans?" *Immunology Today* (1999) 20(4):190-195.

Van de Wal et al., "Selective deamidation by tissue transglutaminase strongly enhances gliadin-specific T cell reactivity," *The Journal of Immunology* (1998) 161(4):1585-1588.

Arentz-Hansen et al., "Celiac lesion T cells recognize epitopes that cluster in regions of gliadins rich in proline residues," *Gastroenterology* (2002) 123(3):803-809.

Jung et al., "From combinatorial libraries to MHC ligand motifs, T-cell superagonists and antagonists," *Biologicals* (2001) 29(3-4):179-181.

Mowat et al., "Coeliac disease—a future for peptide therapy?," *Lancet* (2000) 356(9226):270-271.

Madsen et al., "A humanized model for multiple sclerosis using HLA-DR2 and a human T-cell receptor," *Nature Genetics* (1999) 23(3):343-347.

Van de Wal et al., "Coeliac disease: it takes three to tango!," *Gut* (2000) 46(5):734-737.

Vader et al., "Specificity of Tissue Transglutaminase Explains Cereal Toxicity in Celiac Disease," *Journal of Experimental Medicine* (2002) 195(5):643-649.

Wieser et al., "Coeliac active peptides from gliadin: large-scale preparation and characterization," *Z Lebensm Unters Forsch* (1992) 194(3):229-234.

Kumar et al., "Human genome search in celiac disease: mutated gliadin T-cell-like epitope in two human proteins promotes T-cell activation," *Journal of Molecular Biology* (2002) 319(3):579-599.

Moustakes et al., "Structure of celiac disease-associated HLA-DQ8 and non-associated HLA-DQ9 alleles in complex with two disease-specific epitopes," *International Immunology* (2000) 12(8):1157-1166.

Piper et al., "High Selectivity of Human Tissue Transglutaminase for Immunoactive Gliadin Peptides: Implications for Celiac Sprue," *Biochemistry* (2002) 41(1):386-393.

Plebanski et al., "Protection from *Plasmodium berghei* infection by priming and boosting T cells to a single class I-restricted epitope with recombinant carriers suitable for human use," *Eur J Immunol* (1998) 28(12):4345-4355.

Vader et al., "The gluten response in children with celiac disease is directed toward multiple gliadin and glutenin peptides," *Gastroenterology* (2002) 122:1729-1737.

* cited by examiner

Fig.1a.
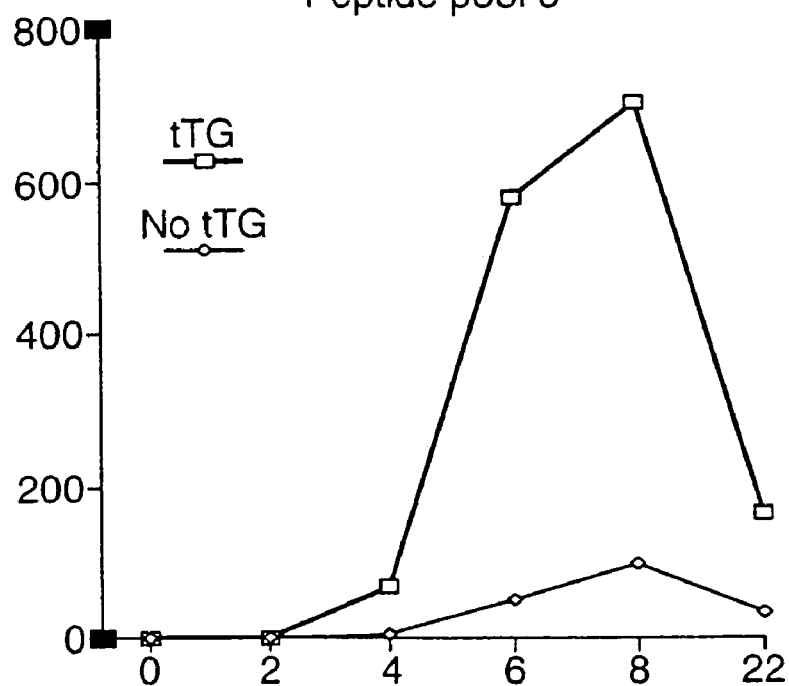
Peptide pool 3
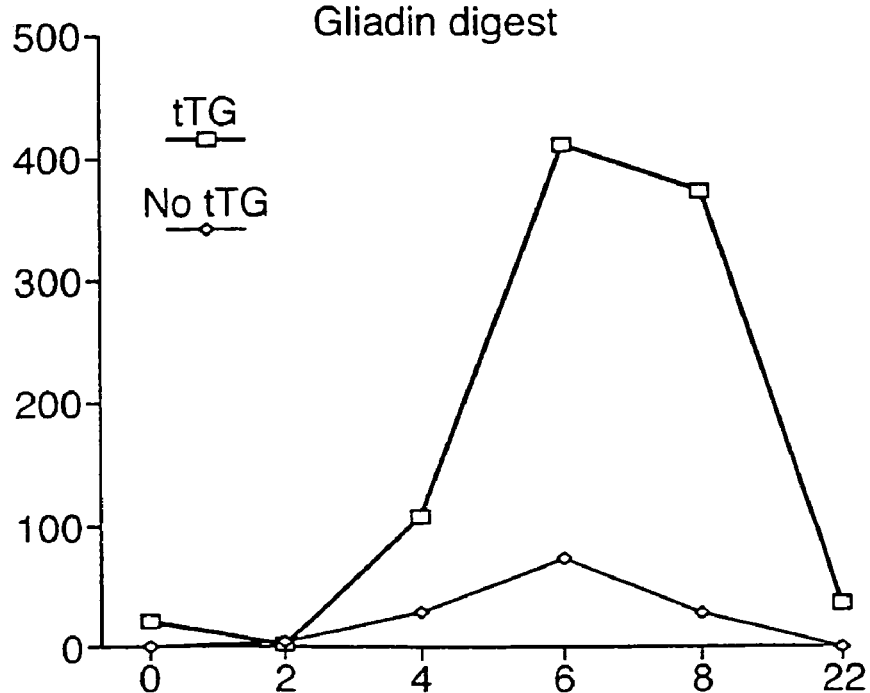
Gliadin digest

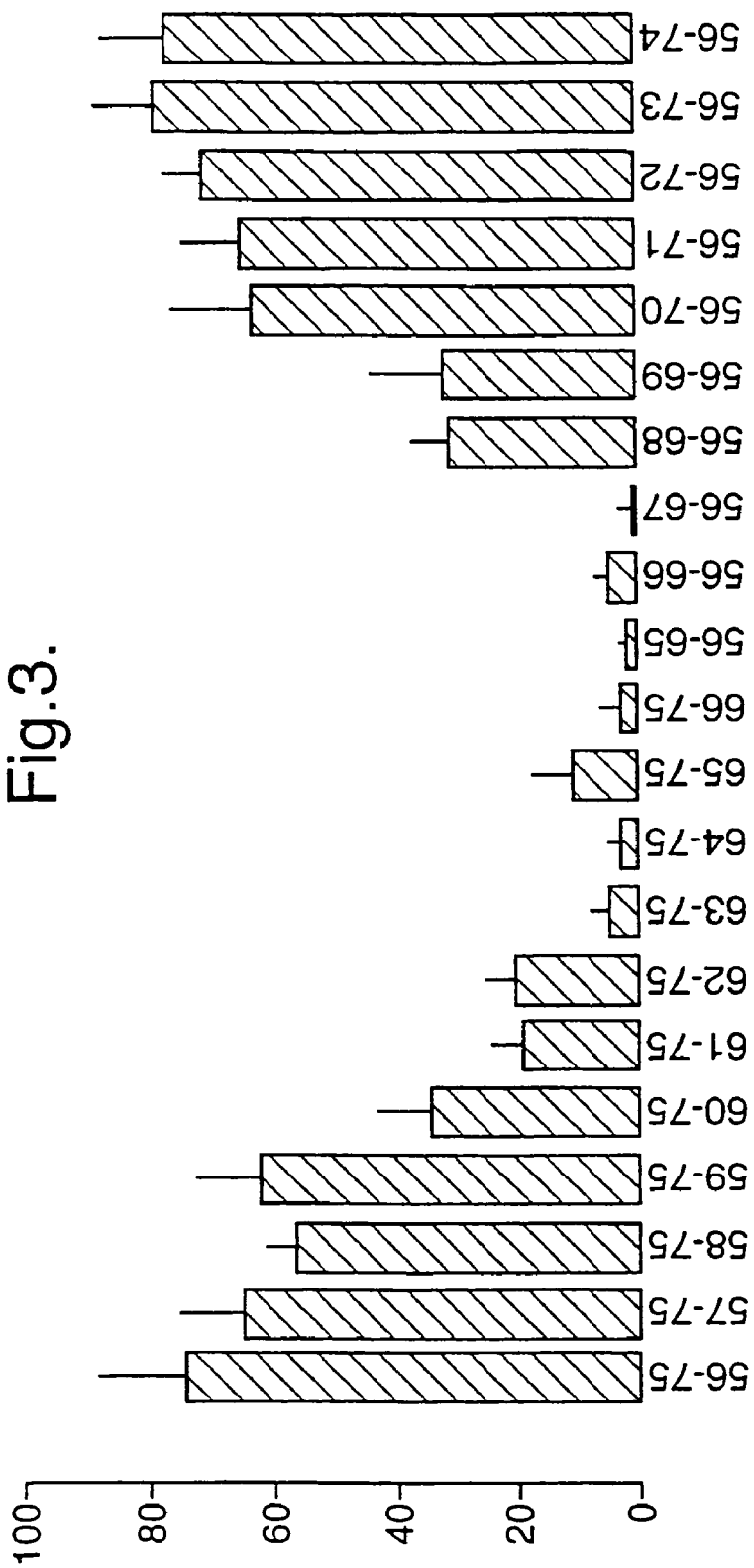

Fig. 10.
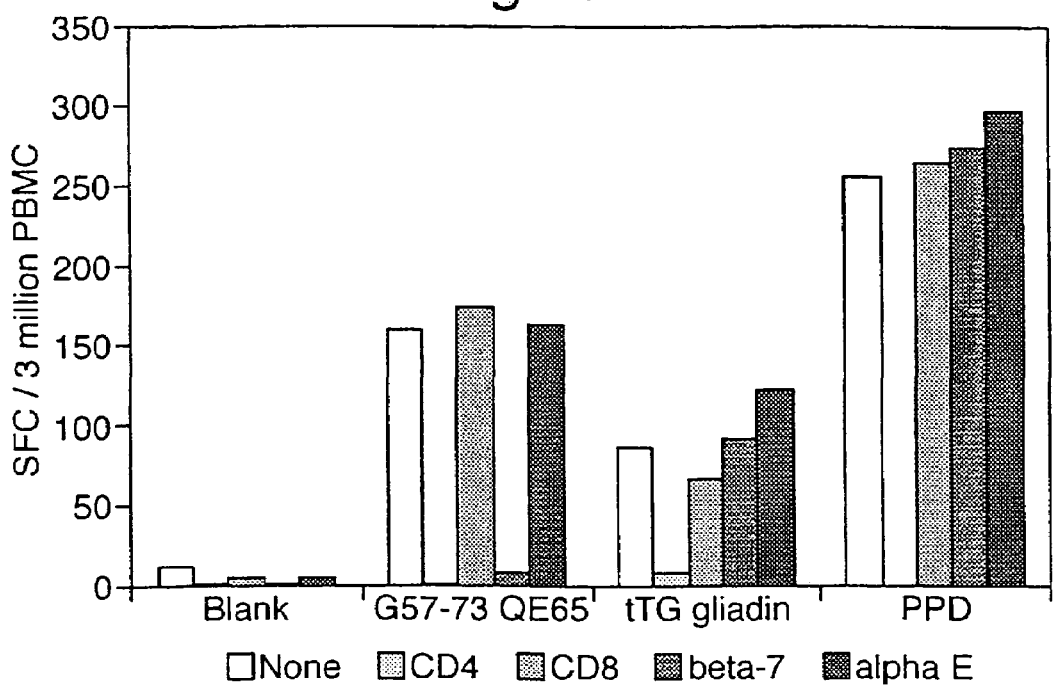
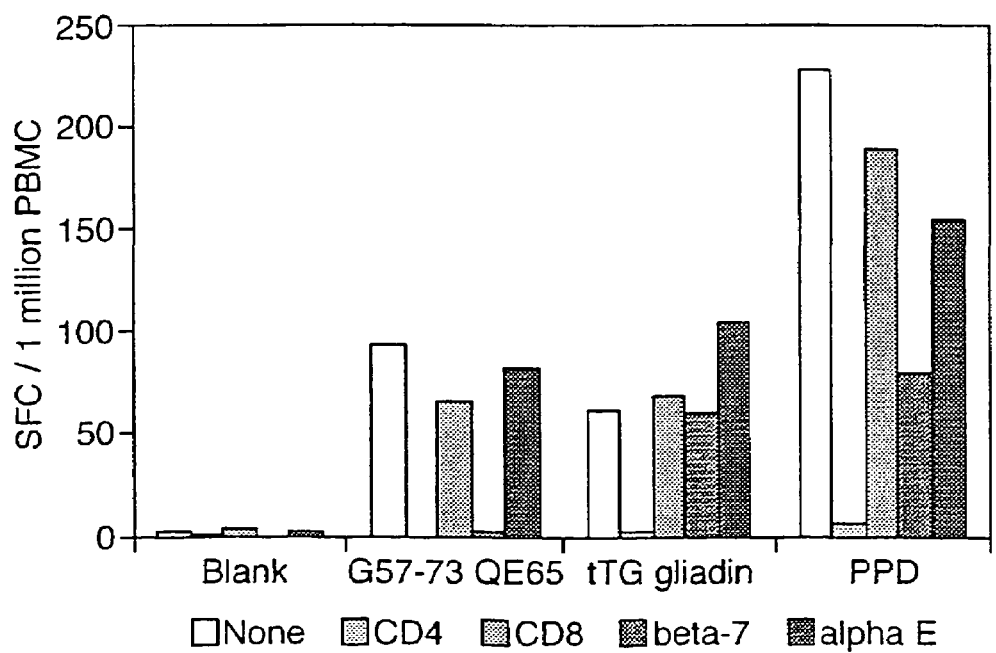

Dose response to A-gliadin 57-73 QE65:
QLQPFPQPELPYPQPQS.

Dose response to GDA4_WHEAT P04724 84-100 QE92:
PQLPYPQPELPYPQPQP.

Dose response to A-gliadin 57-73:
QLQPFPQPQLPYPQPQS (2.5, 25 & 250 mcg/ml),
and A-gliadin 57-73 (25 mcg/ml) + tTG treatment.

Dose response to GDA4_WHEAT P04724 84-100:
PQLPYPQPQLPYPQPQP (2.5, 25 & 250 mcg/ml),
and P04724 84-100 (25 mcg/ml) + tTG treatment.

Dose response to the DQ2-restricted α gliadin T cell epitope A-gliadin 57-68 QE65: QLQPFPQPELPY (E65) (2.5, 25 & 250 mcg/ml), and A-gliadin 57-68: QLQPFPQPQLPY (Q65) (25 mcg/ml) +/- tTG treatment.

Dose response to the DQ2-restricted α gliadin T cell epitope α-2 62-75 QE65 & QE72: PQPELPYPQPELPY (E65) (2.5, 25 & 250 mcg/ml), and α-2 62-75: PQPQLPYPQPQLPY (Q65) (25 mcg/ml) +/- tTG treatment.

Dose response to the DQ8-restricted α gliadin T cell epitope GDA9 202-219: QE208 & 216: QQYPSGEGSFQPSQENPQ (E) (25 & 250 mcg/ml), and to GDA9 202-219 QQYPSGQGSFQPSQQNPQ (Q) (25 mcg/ml) +/- tTG treatment.

Dose response to the DQ2-restricted γ gliadin T cell epitope GDB2 134-153 QE140, 148,150: QQLPQPEQPQQSFPEQERPF (E) (25 & 250 mcg/ml), and to GDB2 134-153: QQLPQPQQPQQSFPQQQRPF (Q) (25 mcg/ml) +/- tTG treatment.

Dose response to gliadin digest by chymotrysin.

Dose response to gliadin digested by chymotrysin then treated with tTG.

Total ELISpot responses to A-gliadin 57-73 QE65 (25mcg/ml) versus A-gliadin 57-73 QE65 responses as percent of tTG gliadin (500mcg/ml) responses.

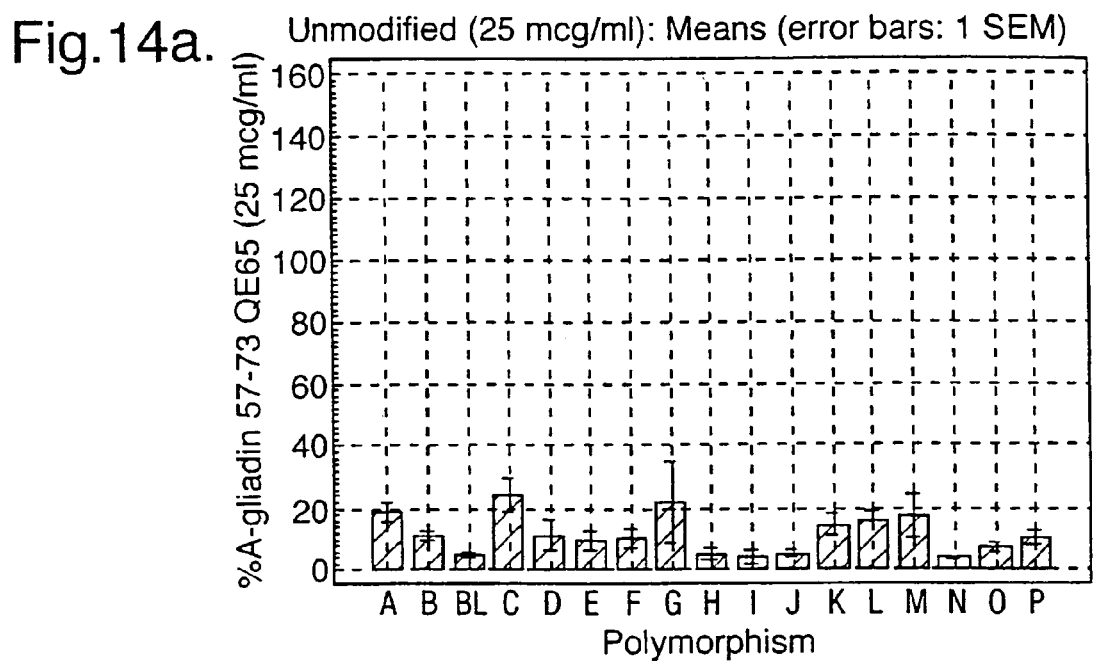

(Fig.14.)

Bioactivity of gliadin polymorphisms of A-gliadin 57-73 (A) in coeliac subjects 6/7 days after gluten challenge (Gamma-Interferon Elispot) (n=4).

Fig.14a.

| | | | |
|---|---|---|---|
| A | QLQPFPQPQLPYPQPQS | I | QLQPFPQPQLSYSQPQP |
| B | QLQPFPQPQLPYPQPQP | J | QPQPFPPPQLPYPQTQP |
| C | QLQPFPQPQLPYPQPQL | K | PQLPYPQPQLPYPQPQP |
| D | QLQPFPQPQLPYLQPQS | L | PQLPYPQPQLPYPQPQL |
| E | QLQPFPRPQLPYPQPQP | M | PQPQPFLPQLPYPQPQS |
| F | QLQPFPQPQLPYSQPQP | N | PQPQPFPPQLPYPQPQS |
| G | QLQPFLQPQLPYSQPQP | O | PQPQPFPPQLPYPQTQP |
| H | QLQPFSQPQLPYSQPQP | P | PQPQPFPPQLPYPQPPP |

A QLQPFPQPQLPYPQPQS
B QLQPFPQPQLPYPQPQP
C QLQPFPQPQLPYPQPQL
D QLQPFPQPQLPYLQPQS
E QLQPFPRPQLPYPQPQP
F QLQPFPQPQLPYSQPQP
G QLQPFLQPQLPYSQPQP
H QLQPFSQPQLPYSQPQP
I QLQPFPQPQLSYSQPQP
J QPQPFPPPQLPYPQTQP
K PQLPYPQPQLPYPQPQP
L PQLPYPQPQLPYPQPQL
M PQPQPFLPQLPYPQPQS
N PQPQPFPPQLPYPQPQS
O PQPQPFPPQLPYPQTQP
P PQPQPFPPQLPYPQPPP

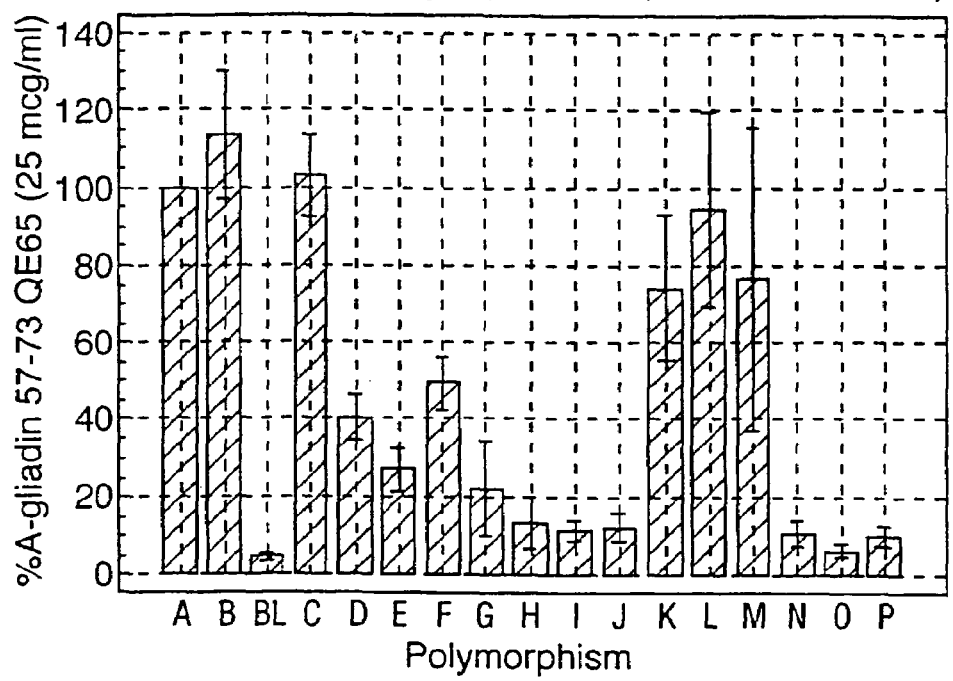

Fig. 14c.

QE65 substituted (25 mcg/ml): Means (error bars: 1 SEM)

A  QLQPFPQPQLPYPQPQS
B  QLQPFPQPQLPYPQPQP
C  QLQPFPQPQLPYPQPQL
D  QLQPFPQPQLPYLQPQS
E  QLQPFPRPQLPYPQPQP
F  QLQPFPQPQLPYSQPQP
G  QLQPFLQPQLPYSQPQP
H  QLQPFSQPQLPYSQPQP
I  QLQPFPQPQLSYSQPQP
J  QPQPFPPPQLPYPQTQP
K  PQLPYPQPQLPYPQPQP
L  PQLPYPQPQLPYPQPQL
M  PQPQPFLPQLPYPQPQS
N  PQPQPFPPQLPYPQPQS
O  PQPQPFPPQLPYPQTQP
P  PQPQPFPPQLPYPQPPP

A  QLQPFPQPQLPYPQPQS
B  QLQPFPQPQLPYPQPQP
C  QLQPFPQPQLPYPQPQL
D  QLQPFPQPQLPYLQPQS
E  QLQPFPRPQLPYPQPQP
F  QLQPFPQPQLPYSQPQP
G  QLQPFLQPQLPYSQPQP
H  QLQPFSQPQLPYSQPQP
I  QLQPFPQPQLSYSQPQP
J  QPQPFPPPQLPYPQTQP
K  PQLPYPQPQLPYPQPQP
L  PQLPYPQPQLPYPQPQL
M  PQPQPFLPQLPYPQPQS
N  PQPQPFPPQLPYPQPQS
O  PQPQPFPPQLPYPQTQP
P  PQPQPFPPQLPYPQPPP

Alanine scan: Means (error bars: 95% CI for mean)

Lysine scan: Means (error bars: 95% CI for mean)

Fig. 17.

Agonist activity of A-gliadin 57-73 QE65 variants according to position substituted (Mean of 8 coeliac subjects' PBMC responses in interferon gamma ELISPOT after gluten challenge)

QLQP<u>FPQPELPYPQ</u>PQS
60................70

P60: Means (error bars: 95% CI for mean)

Agonist activity of A-gliadin 57-73 QE65 variants according to position substituted (Mean of 8 coeliac subjects' PBMC responses in interferon gamma ELISPOT after gluten challenge)
QLQPFPQPELPY Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60.................70

Agonist activity of A-gliadin 57-73 QE65 variants according to position substituted (Mean of 8 coeliac subjects' PBMC responses in interferon gamma ELISPOT after gluten challenge)
QLQPFPQPELPY Agonist activity of A-gliadin 57-73 QE65 variants according to position substituted (Mean of 8 coeliac subjects' PBMC responses in interferon gamma ELISPOT after gluten challenge)

QLQPFPQPELPYPQPQS
60................70

Fig. 22.

Agonist activity of A-gliadin 57-73 QE65 variants according to position substituted (Mean of 8 coeliac subjects' PBMC responses in interferon gamma ELISPOT after gluten challenge)

QLQPFPQPELPYPQPQS
60.................70

Fig.23.

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60.................70

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60...................70

Agonist activity of A-gliadin 57-73 QE65 variants according to position substituted (Mean of 8 coeliac subjects' PBMC responses in interferon gamma ELISPOT after gluten challenge)
QLQPFPQPEL Agonist activity of A-gliadin 57-73 QE65 variants according to position substituted (Mean of 8 coeliac subjects' PBMC responses in interferon gamma ELISPOT after gluten challenge)
QLQPFPQPELPYPQPQ

Fig. 27.

Agonist activity of A-gliadin 57-73 QE65 variants according to position substituted (Mean of 8 coeliac subjects' PBMC responses in interferon gamma ELISPOT after gluten challenge)

QLQPFPQPELPYPQPQS
60.................70

Q70 Means (error bars: 95% CI for mean)

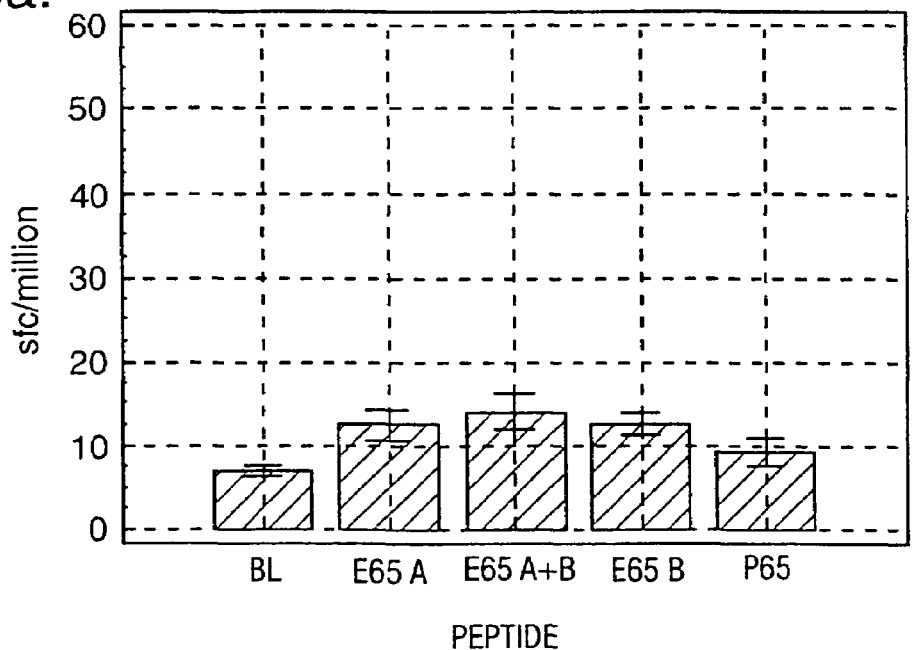
(Fig. 28.)
Interferon gamma ELISpot responses in newly diagnosed and treated coeliac subjects, before and after gluten challenge.
Fig. 28a. Untreated, newly diagnosed coeliacs (Mean+SEM, n=9)

DIAGNOSIS OF COELIAC DISEASE USING A GLIADIN EPITOPE

The invention relates to the diagnosis and therapy of coeliac disease, and to a gliadin protein which does not cause coeliac disease.

An immune reaction to gliadin (a component of gluten) in the diet causes coeliac disease. It is known that immune responses in the intestinal tissue preferentially respond to gliadin which has been modified by an intestinal transglutaminase. Coeliac disease is diagnosed by detection of anti-endomysial antibodies, but this requires confirmation by the finding of a lymphocytic inflammation in intestinal biopsies. The taking of such a biopsy is inconvenient for the patient.

Investigators have previously assumed that only intestinal T cell responses provide an accurate indication of the immune response against gliadins. Therefore they have concentrated on the investigation of T cell responses in intestinal tissue. Gliadin epitopes which require transglutaminase modification (before they are recognised by the immune system) are known[2].

The inventors have found the immunodominant T cell epitope recognised by the immune system in coeliac disease, and have shown that this is recognised by T cells in the peripheral blood of individuals with coeliac disease. Such T cells were found to be present at high enough frequencies to be detectable without restimulation (i.e. a 'fresh response' detection system could be used). The epitope was identified using a non-T cell cloning based method which provided a more accurate reflection of the epitopes being recognised. The immunodominant epitope requires transglutaminase modification (causing substitution of a particular glutamine to glutamate) before immune system recognition.

Based on this work the inventors have developed a test which can be used to diagnose coeliac disease at an early stage. The test may be carried out on a sample from peripheral blood and therefore an intestinal biopsy is not required. The test is more sensitive than the antibody tests which are currently being used.

The invention thus provides a method of diagnosing coeliac disease, or susceptibility to coeliac disease, in an individual comprising:

(a) contacting a sample from the host with an agent selected from (i) the epitope comprising sequence which is: SEQ ID NO: 1 or 2, or an equivalent sequence from a naturally occurring homologue of the gliadin represented by SEQ ID NO:3, (ii) an epitope comprising sequence comprising: SEQ ID NO:1, or an equivalent sequence from a naturally occurring homologue of the gliadin represented by SEQ ID NO:3, which epitope is an isolated oligopeptide derived from a gliadin protein, (iii) an analogue of (i) or (ii) which is capable of being recognised by a T cell receptor that recognises (i) or (ii), which in the case of a peptide analogue is not more than 50 amino acids in length, or (iv) a product comprising two or more agents as defined in (i), (ii) or (iii), and (b) determining in vitro whether T cells in the sample recognise the agent, recognition by the T cells indicating that the individual has, or is susceptible to, coeliac disease.

The invention also provides use of the agent for the preparation of a diagnostic means for use in a method of diagnosing coeliac disease, or susceptibility to coeliac disease, in an individual, said method comprising determining whether T cells of the individual recognise the agent, recognition by the T cells indicating that the individual has, or is susceptible to, coeliac disease.

The finding of an immunodominant epitope which is modified by transglutaminase also allows diagnosis of coeliac disease based on determining whether other types of immune response to this epitope are present. Thus the invention also provides a method of diagnosing coeliac disease, or susceptibility to coeliac disease, in an individual comprising determining the presence of an antibody that binds to the epitope in a sample from the individual, the presence of the antibody indicating that the individual has, or is susceptible to, coeliac disease.

The invention additionally provides the agent, optionally in association with a carrier, for use in a method of treating or preventing coeliac disease by tolerising T cells which recognise the agent. Also provided is an antagonist of a T cell which has a T cell receptor that recognises (i) or (ii), optionally in association with a carrier, for use in a method of treating or preventing coeliac disease by antagonising such T cells. Additionally provided is the agent or an analogue that binds an antibody (that binds the agent) for use in a method of treating or preventing coeliac disease in an individual by tolerising the individual to prevent the production of such an antibody.

The invention provides a method of determining whether a composition is capable of causing coeliac disease comprising determining whether a protein capable of being modified by a transglutaminase to an oligopeptide sequence as defined above is present in the composition, the presence of the protein indicating that the composition is capable of causing coeliac disease.

The invention also provides a mutant gliadin protein whose wild-type sequence can be modified by a transglutaminase to a sequence that comprises an epitope comprising sequence as defined above, but which mutant gliadin protein has been modified in such a way that it does not contain sequence which can be modified by a transglutaminase to a sequence that comprises such an epitope comprising sequence; or a fragment of such a mutant gliadin protein which is at least 15 amino acids long and which comprises sequence which has been modified in said way.

The invention also provides a protein that comprises a sequence which is able to bind to a T cell receptor, which T cell receptor recognises the agent, and which sequence is able to cause antagonism of a T cell that carries such a T cell receptor.

Additionally the invention provides a food that comprises the proteins defined above.

The invention is illustrated by the accompanying drawings in which:

FIG. 1 shows freshly isolated PBMC (peripheral blood mononuclear cell) IFNγ ELISPOT responses (vertical axis shows spot forming cells per $10^6$ PBMC) to transglutaminase (tTG)-treated and untreated peptide pool 3 (each peptide 10 μg/ml) including five overlapping 15mers spanning A-gliadin 51–85 (see Table 1) and a-chymotrypsin-digested gliadin (40 μg/ml) in coeliac disease Subject 1, initially in remission following a gluten free diet then challenged with 200 g bread daily for three days from day 1 (a). PBMC IFNγ ELISPOT responses by Subject 2 to tTG-treated A-gliadin peptide pools 1–10 spanning the complete A-gliadin protein during ten day bread challenge (b). The horizontal axis shows days after commencing bread.

FIG. 2 shows PBMC IFNγ ELISPOT responses to tTG-treated peptide pool 3 (spanning A-gliadin 51–85) in 7 individual coeliac disease subjects (vertical axis shows spot forming cells per $10^6$ PBMC), initially in remission on gluten free diet, challenged with bread for three days (days 1 to 3). The horizontal axis shows days after commencing bread.(a). PBMC IFNg Elispot responses to tTG-treated overlapping 15mer peptides included in pool 3; bars represent the mean (± SEM) response to individual peptides (10 µg/ml) in 6 Coeliac disease subjects' on day 6 or 7(b). (In individual subjects, ELISPOT responses to peptides were calculated as a % of response elicited by peptide 12—as shown by the vertical axis.)

FIG. 3 shows PBMC IFNγ ELISPOT responses to tTG-treated truncations of A-gliadin 56–75 (0.1 µM). Bars represent the mean (±SEM in 5 Coeliac disease subjects. (In individual subjects, responses were calculated as the % of the maximal response elicited by any of the peptides tested.)

FIG. 4 shows how the minimal structure of the dominant A-gliadin epitope was mapped using tTG-treated 7–17mer A-gliadin peptides (0.1 µM) including the sequence, PQP QLPY (A-gliadin 62–68) (a), and the same peptides without tTG treatment but with the substitution Q→E65 (b). Each line represents PBMC IFNg ELISPOT responses in each of three Coeliac disease subjects on day 6 or 7 after bread was ingested on days 1–3. (In individual subjects, ELISPOT responses were calculated as a % of the response elicited by the 17mer, A-gliadin 57–73.)

FIG. 5 shows the amino acids which were deamidated by tTG. A-gliadin 56–75 (LQLQPFPQPQLPYPQPQSFP) (0.1 µM) was incubated with tTG (50 µg/ml) at 37° C. for 2 hours. A single product was identified and purified by reverse phase HPLC. Amino acid analysis allowed % deamidation (Q→E) of each Gln residue in A-gliadin 56–75 attributable to tTG to be calculated (vertical axis).

FIG. 6 shows the effect of substituting Q→E in A-gliadin 57–73 at other positions in addition to Q65 using the 17mers: QLQPFPQP$\underline{E}$LPYPQPEIS (E57,65), QLQPFPQP ELPYPQP$\underline{E}$S (E65,72), $\underline{E}$LQPFPQP$\underline{E}$LPYPQP$\underline{E}$S (E57, 65, 72), and QLQPFPQP$\underline{E}$LPYPQPQS (E65) in three Coeliac disease subjects on day 6 or 7 after bread was ingested on days 1–3. Vertical axis shows % of the E65 response.

FIG. 7 shows that tTG treated A-gliadin 56–75 (0.1 µM) elicited IFN-g ELISPOT responses in (a) CD4 and CD8 magnetic bead depleted PBMC. (Bars represent CD4 depleted PBMC responses as a % of CD8 depleted PBMC responses; spot forming cells per million CD8 depleted PBMC were: Subject 4: 29, and Subject 6: 535). (b) PBMC IFNγ ELISPOT responses (spot forming cells/million PBMC) after incubation with monoclonal antibodies to HLA-DR (L243), -DQ (L2) and -DP (B7.21) (10 µg/ml) 1 h prior to tTG-treated 56–75 (0.1 µM) in two coeliac disease subjects homozygous for HLA-DQ a1*0501, b1*0201.

FIG. 10 shows CD8, CD4, β$_7$, and α$^E$-specific immunomagnetic bead depletion of peripheral blood mononuclear cells from two coeliac subjects 6 days after commencing gluten challenge followed by interferon gamma ELISpot. A-gliadin 57–73 QE65 (25 mcg/ml), tTG-treated chymotrypsin-digested gliadin (100 mcg/ml) or PPD (10 mcg/ml) were used as antigen.

FIGS. 17 to 27 show the agonist activity of A-gliadin 57–73 QE65 variants.

DETAILED DESCRIPTION OF THE INVENTION

Figure 1B:
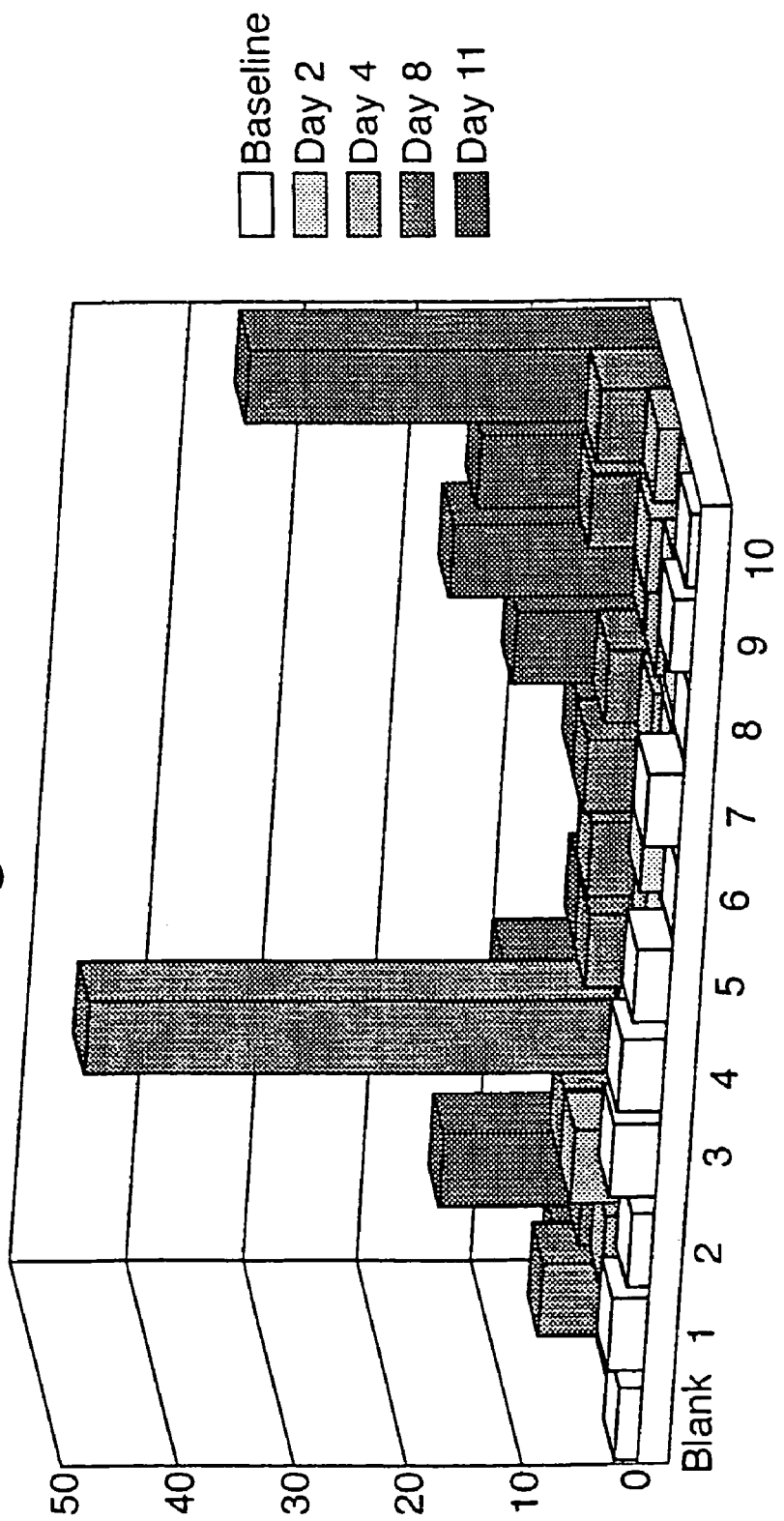

The term 'coeliac disease' encompasses a spectrum of conditions caused by varying degrees of gluten sensitivity, including a severe form characterised by a flat small intestinal mucosa (hyperplastic villous atrophy) and other forms characterised by milder symptoms.

The individual mentioned above (in the context of diagnosis or therapy) is human. They may have coeliac disease (symptomatic or asymptomatic) or be suspected of having it. They may be on a gluten free diet. They may be in an acute phase response (for example they may have coeliac disease, but have only ingested gluten in the last 24 hours before which they had been on a gluten free diet for 14 to 28 days).

The individual may be susceptible to coeliac disease, such as a genetic susceptibility (determined for example by the individual having relatives with coeliac disease or possessing genes which cause predisposition to coeliac disease).

The Agent

The agent is typically a peptide, for example of length 7 to 50 amino acids, such as 10 to 40, or 15 to 30 amino acids in length.

SEQ ID NO:1 is PQPELPY. SEQ ID NO:2 is QLQPF-PQPELPYPQPQS. SEQ ID NO:3 is shown in Table 1 and is the sequence of a whole A-gliadin. The glutamate at position 4 of SEQ ID NO:1 (equivalent to position 9 of SEQ ID NO:2) is generated by transglutaminase treatment of A-gliadin.

The agent may be the peptide represented by SEQ ID NO:1 or 2 or an epitope comprising sequence that comprises SEQ ID NO:1 which is an isolated oligopeptide derived from a gliadin protein; or an equivalent of these sequences from a naturally occurring gliadin protein which is a homologue of SEQ ID NO:3. Thus the epitope may be a derivative of the protein represented by SEQ ID NO:3. Such a derivative is typically a fragment of the gliadin, or a mutated derivative of the whole protein or fragment. Therefore the epitope of the invention does not include this naturally occurring whole gliadin protein, and does not include other whole naturally occurring gliadins.

The epitope may thus be a fragment of A-gliadin (e.g. SEQ ID NO:3), which comprises the sequence of SEQ ID NO:1, obtainable by treating (fully or partially) with transglutaminase, i.e. with 1, 2, 3 or more glutamines substituted to glutamates (including the substitution within SEQ ID NO:1).

Such fragments may be or may include the sequences represented by positions 55 to 70, 58 to 73, 61 to 77 of SEQ ID NO:3 shown in Table 1. Typically such fragments will be recognised by T cells to at least the same extent that the peptides represented by SEQ ID NO:1 or 2 are recognised in any of the assays described herein using samples from coeliac disease patients.

In the case where the epitope comprises a sequence equivalent to the above epitopes (including fragments) from another gliadin protein (e.g. any of the gliadin proteins mentioned herein or any gliadins which cause coeliac disease), such equivalent sequences will correspond to a fragment of a gliadin protein typically treated (partially or fully) with transglutaminase. Such equivalent peptides can be determined by aligning the sequences of other gliadin proteins with SEQ ID NO:3 (for example using any of the programs mentioned herein). Transglutaminase is commercially available (e.g. Sigma T-5398). Table 4 provides examples of suitable equivalent sequences.

The agent which is an analogue is capable of being recognised by a TCR which recognises (i) or (ii). Therefore generally when the analogue is added to T cells in the presence of (i) or (ii), typically also in the presence of an antigen presenting cell (APC) (such as any of the APCs mentioned herein), the analogue inhibits the recognition of (i) or (ii), i.e. the analogue is able to compete with (i) or (ii) in such a system.

The analogue may be one which is capable of binding the TCR which recognises (i) or (ii). Such binding can be tested by standard techniques. Such TCRs can be isolated from T cells which have been shown to recognise (i) or (ii) (e.g. using the method of the invention). Demonstration of the binding of the analogue to the TCRs can then shown by determining whether the TCRs inhibit the binding of the analogue to a substance that binds the analogue, e.g. an antibody to the analogue. Typically the analogue is bound to a class II MHC molecule (e.g. HA-DQ2) in such an inhibition of binding assay.

Typically the analogue inhibits the binding of (i) or (ii) to a TCR. In this case the amount of (i) or (ii) which can bind the TCR in the presence of the analogue is decreased. This is because the analogue is able to bind the TCR and therefore competes with (i) or (ii) for binding to the TCR.

T cells for use in the above binding experiments can be isolated from patients with coeliac disease, for example with the aid of the method of the invention. Other binding characteristics of the analogue may also be the same as (i) or (ii), and thus typically the analogue binds to the same MHC class II molecule to which the peptide binds (HLA-DQ2). The analogue typically binds to antibodies specific for (i) or (ii), and thus inhibits binding of (i) or (ii) to such antibodies.

The analogue is typically a peptide. It may have homology with (i) or (ii), typically at least 70% homology, preferably at least 80, 90%, 95%, 97% or 99% homology with (i) or (ii), for example over a region of at least 15 more (such as the entire length of the analogue and/or (i) or (ii), or across the region which contacts the TCR or binds the MHC molecule) contiguous amino acids. Methods of measuring protein homology are well known in the art and it will be understood by those of skill in the art that in the present context, homology is calculated on the basis of amino acid identity (sometimes referred to as "hard homology").

For example the UWGCG Package provides the BEST-FIT program which can be used to calculate homology (for example used on its default settings) (Devereux et al (1984) *Nucleic Acids Research* 12, p387–395). The PILEUP and BLAST algorithms can be used to calculate homology or line up sequences (typically on their default settings), for example as described in Altschul S. F. (1993) J Mol Evol 36:290–300; Altschul, S, F et al (1990) J Mol Biol 215: 403–10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873–5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous peptide analogues typically differ from (i) or (ii) by 1, 2, 3, 4, 5, 6, 7, 8 or more mutations (which may be substitutions, deletions or insertions). These mutation may be measured across any of the regions mentioned above in relation to calculating homology. The substitutions are preferably 'conservative'. These are defined according to the following Table. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Typically the amino acids in the analogue at the equivalent positions to amino acids in (i) or (ii) which contribute to binding the MHC molecule or are responsible for the recognition by the TCR, are the same or are conserved.

Typically the analogue peptide comprises one or more modifications, which may be natural post-translation modifications or artificial modifications. The modification may provide a chemical moiety (typically by substitution of a hydrogen, e.g. of a C—H bond), such as an amino, acetyl, hydroxy or halogen (e.g. fluorine) group or carbohydrate group. Typically the modification is present on the N or C terminus.

The analogue may comprise one or more non-natural amino acids, for example amino acids with a side chain different from natural amino acids. Generally, the non-natural amino acid will have an N terminus and/or a C terminus. The non-natural amino acid may be an L- or a D-amino acid.

The analogue typically has a shape, size, flexibility or electronic configuration which is substantially similar to (i) or (ii). It is typically a derivative of (i) or (ii). In one embodiment the analogue is a fusion protein comprising the sequence of SEQ ID NO:1 or 2, or any of the other peptides mentioned herein; and non-gliadin sequence.

In one embodiment the analogue is or mimics (i) or (ii) bound to a MHC class II molecule. 2, 3, 4 or more of such complexes may be associated or bound to each other, for example using a biotin/streptavidin based system, in which typically 2, 3 or 4 biotin labelled MHC molecules bind to a streptavidin moiety. This analogue typically inhibits the binding of the (i) or (ii)/MHC Class II complex to a TCR or antibody which is specific for the complex.

The analogue is typically an antibody or a fragment of an antibody, such as a Fab or (Fab)$_2$ fragment. The analogue may be immobilised on a solid support, particularly an analogue which mimics peptide bound to a MHC molecule.

The analogue is typically designed by computational means and then synthesised using methods known in the art. Alternatively the analogue can be selected from a library of compounds. The library may be a combinatorial library or a display library, such as a phage display library. The library of compounds may be expressed in the display library in the form of being bound to a MHC class II molecule, such as HLA-DQ2. Analogues are generally selected from the library based on their ability to mimic the binding characteristics (i) or (ii). Thus they may be selected based on ability to bind a TCR or antibody which recognises (i) or (ii).

Typically analogues will be recognised by T cells to at least the same extent as any of the agents (i) or (ii), for example at least to the same extent as the equivalent epitope and preferably to the same extent as the peptide represented by SEQ ID NO:2, is recognised in any of the assays described herein, typically using T cells from coeliac disease patients. Analogues may be recognised to these extents in vivo and thus may be able to induce coeliac disease symptoms to at least the same extent as any of the agents mentioned herein (e.g. in a human patient or animal model).

Analogues may be identified in a method comprising determining whether a candidate substance is recognised by a T cell receptor that recognises an epitope of the invention, recognition of the substance indicating that the substance is an analogue. Such TCRs may be any of the TCRs mentioned herein, and may be present on T cells. Any suitable assay mentioned herein can be used to identify the analogue. In one embodiment this method is carried out in vivo. As mentioned above preferred analogues are recognised to at least the same extent as the peptide SEQ ID NO:2, and so the method may be used to identify analogues which are recognised to this extent.

In one embodiment the method comprises determining whether a candidate substance is able to inhibit the recognition of an epitope of the invention, inhibition of recognition indicating that the substance is an analogue.

The agent may be a product comprising at least 2, 5, 10 or 20 agents as defined by (i), (ii) or (iii). Typically the composition comprises epitopes of the invention (or equivalent analogues) from different gliadins, such as any of the species or variety of or types of gliadin mentioned herein. Preferred compositions comprise at least one epitope of the invention, or equivalent analogue, from all of the gliadins present in any of the species or variety mentioned herein, or from 2, 3, 4 or more of the species mentioned herein (such as from the panel of species consisting of wheat, rye, barley, oats and triticale).

Diagnosis

As mentioned above the method of diagnosis of the invention may be based on the detection of T cells which bind the agent or on the detection of antibodies that recognise the agent.

The T cells which recognise the agent in the method (which includes the use mentioned above) are generally T cells which have been pre-sensitised in vivo to gliadin. As mentioned above such antigen-experienced T cells have been found to be present in the peripheral blood.

In the method the T cells can be contacted with the agent in vitro or in vivo, and determining whether the T cells recognise the agent can be performed in vitro or in vivo. Thus the invention provides the agent for use in a method of diagnosis practiced on the human body. Different agents are provided for simultaneous, separate or sequential use in such a method.

The in vitro method is typically carried out in aqueous solution into which the agent is added. The solution will also comprise the T cells (and in certain embodiments the APCs discussed below). The term 'contacting' as used herein includes adding the particular substance to the solution.

Determination of whether the T cells recognise the agent is generally done by detecting a change in the state of the T cells in the presence of the agent or determining whether the T cells bind the agent. The change in state is generally caused by antigen specific functional activity of the T cell after the TCR binds the agent The change of state may be measured inside (e.g. change in intracellular expression of proteins) or outside (e.g. detection of secreted substances) the T cells.

The change in state of the T cell may be the start of or increase in secretion of a substance from the T cell, such as a cytokine, especially IFN-γ, IL-2 or TNF-α. Determination of IFN-γ secretion is particularly preferred. The substance can typically be detected by allowing it to bind to a specific binding agent and then measuring the presence of the specific binding agent/substance complex. The specific binding agent is typically an antibody, such as polyclonal or monoclonal antibodies. Antibodies to cytokines are commercially available, or can be made using standard techniques.

Typically the specific binding agent is immobilised on a solid support. After the substance is allowed to bind the solid support can optionally be washed to remove material which is not specifically bound to the agent. The agent/substance complex may be detected by using a second binding agent which will bind the complex. Typically the second agent binds the substance at a site which is different from the site which binds the first agent. The second agent is preferably an antibody and is labelled directly or indirectly by a detectable label.

Thus the second agent may be detected by a third agent which is typically labelled directly or indirectly by a detectable label. For example the second agent may comprise a biotin moiety, allowing detection by a third agent which comprises a streptavidin moiety and typically alkaline phosphatase as a detectable label.

In one embodiment the detection system which is used is the ex-vivo ELISPOT assay described in WO 98/23960. In that assay IFN-γ secreted from the T cell is bound by a first IFN-γ specific antibody which immobilised on a solid support. The bound IFN-γ is then detected using a second IFN-γ specific antibody which is labelled with a detectable label. Such a labelled antibody can be obtained from MABTECH (Stockholm, Sweden). Other detectable labels which can be used are discussed below.

The change in state of the T cell which can be measured may be the increase in the uptake of substances by the T cell, such as the uptake of thymidine. The change in state may be an increase in the size of the T cells, or proliferation of the T cells, or a change in cell surface markers on the T cell.

In one embodiment the change of state is detected by measuring the change in the intracellular expression of proteins, for example the increase in intracellular expression of any of the cytokines mentioned above. Such intracellular changes may be detected by contacting the inside of the T cell with a moiety that binds the expressed proteins in a specific manner and which allows sorting of the T cells by flow cytometry.

In one embodiment when binding the TCR the agent is bound to an MHC class II molecule (typically HLA-DQ2), which is typically present on the surface of an antigen presenting cell (APC). However as mentioned herein other agents can bind a TCR without the need to also bind an MHC molecule.

Generally the T cells which are contacted in the method are taken from the individual in a blood sample, although other types of samples which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T cells and APCs. Thus in the method the APCs present in the separated MCs can present the peptide to the T cells. In another embodiment only T cells, such as only CD4 T cells, can be purified from the sample. PBMCs, MCs and T cells can be separated from the sample using techniques known in the art, such as those described in Lalvani et al (1997) *J. Exp. Med.* 186, p859–865.

In one embodiment the T cells used in the assay are in the form of unprocessed or diluted samples, or are freshly isolated T cells (such as in the form of freshly isolated MCs or PBMCs) which are used directly ex vivo, i.e. they are not cultured before being used in the method. Thus the T cells have not been restimulated in an antigen specific manner in vitro. However the T cells can be cultured before use, for example in the presence of one or more of the agents, and generally also exogenous growth promoting cytokines. During culturing the agent(s) are typically present on the surface of APCs, such as the APC used in the method. Pre-culturing of the T cells may lead to an increase in the sensitivity of the method. Thus the T cells can be converted into cell lines, such as short term cell lines (for example as described in Ota et al (1990) *Nature* 346, p183–187).

The APC which is typically present in the method may be from the same individual as the T cell or from a different host The APC may be a naturally occurring APC or an artificial APC. The APC is a cell which is capable of presenting the peptide to a T cell. It is typically a B cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalised cell line. The APC may express empty MHC class II molecules on its surface.

In the method one or more (different) agents may be used. Typically the T cells derived from the sample can be placed into an assay with all the agents which it is intended to test or the T cells can be divided and placed into separate assays each of which contain one or more of the agents.

The invention also provides the agents such as two or more of any of the agents mentioned herein (e.g. the combinations of agents which are present in the composition agent discussed above) for simultaneous separate or sequential use (eg. for in vivo use).

In one embodiment agent per se is added directly to an assay comprising T cells and APCs. As discussed above the T cells and APCs in such an assay could be in the form of MCs. When agents which can be recognised by the T cell without the need for presentation by APCs are used then APCs are not required. Analogues which mimic the original (i) or (ii) bound to a MHC molecule are an example of such an agent.

In one embodiment the agent is provided to the APC in the absence of the T cell. The APC is then provided to the T cell, typically after being allowed to present the agent on its surface. The peptide may have been taken up inside the APC and presented, or simply be taken up onto the surface without entering inside the APC.

The duration for which the agent is contacted with the T cells will vary depending on the method used for determining recognition of the peptide. Typically $10^5$ to $10^7$, preferably $5 \times 10^5$ to $10^6$ PBMCs are added to each assay. In the case where agent is added directly to the assay its concentration is from $10^{-1}$ to $10^3$ g/ml, preferably 0.5 to 50 µg/ml or 1 to 10 µg/ml.

Typically the length of time for which the T cells are incubated with the agent is from 4 to 24 hours, preferably 6 to 16 hours. When using ex vivo PBMCs it has been found that $0.3 \times 10^6$ PBMCs can be incubated in 10 µg/ml of peptide for 12 hours at 37° C.

The determination of the recognition of the agent by the T cells may be done by measuring the binding of the agent to the T cells (this can be carried out using any suitable binding assay format discussed herein). Typically T cells which bind the agent can be sorted based on this binding, for example using a FACS machine. The presence of T cells which recognise the agent will be deemed to occur if the frequency of cells sorted using the agent is above a 'control' value. The frequency of antigen-experienced T cells is generally 1 in $10^6$ to 1 in $10^3$, and therefore whether or not the sorted cells are antigen-experienced T cells can be determined.

The determination of the recognition of the agent by the T cells may be measured in vivo. Typically the agent is administered to the host and then a response which indicates recognition of the agent may be measured. The agent is typically administered intradermally or epidermally. The agent is typically administered by contacting with the outside of the skin, and may be retained at the site with the aid of a plaster or dressing. Alternatively the agent may be administered by needle, such as by injection, but can also be administered by other methods such as ballistics (e.g. the ballistics techniques which have been used to deliver nucleic acids). EP-A-0693119 describes techniques which can typically be used to administer the agent. Typically from 0.001 to 1000 µg, for example from 0.01 to 100 µg or 0.1 to 10 µg of agent is administered.

In one embodiment a product can be administered which is capable of providing the agent in vivo. Thus a polynucleotide capable of expressing the agent can be administered, typically in any of the ways described above for the administration of the agent. The polynucleotide typically has any of the characteristics of the polynucleotide provided by the invention which is discussed below. The agent is expressed from the polynucleotide in vivo. Typically from 0.001 to 1000 μg, for example from 0.01 to 100 μg or 0.1 to 10 μg of polynucleotide is administered.

Recognition of the agent administered to the skin is typically indicated by the occurrence of inflammation (e.g. induration, erythema or oedema) at the site of administration. This is generally measured by visual examination of the site.

The method of diagnosis based on the detection of an antibody that binds the agent is typically carried out by contacting a sample from the individual (such as any of the samples mentioned here, optionally processed in any manner mentioned herein) with the agent and determining whether an antibody in the sample binds the agent, such a binding indicating that the individual has, or is susceptible to coeliac disease. Any suitable format of binding assay may be used, such as any such format mentioned herein.

Therapy

The identification of the immunodominant epitope allows the therapeutic products to be made which target the T cells which recognise this epitope (such T cells being ones which participate in the immune response against gliadin). This finding also allows the prevention or treatment of coeliac disease by suppressing (by tolerisation) an antibody or T cell response to the epitope.

Certain agents of the invention bind the TCR which recognises the epitope of the invention (as measured using any of the binding assays discussed above) and cause tolerisation of the T cell that carries the TCR Such agents, optionally in association with a carrier, can therefore be used to prevent or treat coeliac disease.

Generally tolerisation can be caused by the same peptides which can (after being recognised by the TCR) cause antigen specific functional activity of the T cell (such as any such activity mentioned herein, e.g. secretion of cytokines). Such agents cause tolerisation when they are presented to the immune system in a 'tolerising' context.

Tolerisation leads to a decrease in the recognition of a T cell or antibody epitope by the immune system. In the case of a T cell epitope this can be caused by the deletion or anergising of T cells which recognise the epitope. Thus T cell activity (for example as measured in suitable assays mentioned herein) in response to the epitope is decreased. Tolerisation of an antibody response means that a decreased amount of specific antibody to the epitope is produced when the epitope is administered.

Methods of presenting antigens to the immune system in such a context are known and are described for example in Yoshida et al. Clin. Immunol. Immunopathol. 82, 207–215 (1997), Thurau et al. Clin. Exp. Immunol. 109, 370–6 (1997), and Weiner et al. Res. Immunol. 148, 528–33 (1997). In particular certain routes of administration can cause tolerisation, such as oral, nasal or intraperitoneal. Particular products which cause tolerisation may be administered (e.g. in a composition which also comprises the agent) to the individual. Such products include cytokines, such as cytokines which favour a Th2 response (e.g. IL-4, TGF-β or IL-10). Products or agent may be administered at a dose which causes tolerisation.

The invention provides a protein which comprises a sequence able to act as an antagonist of the T cell (which T cell recognises the agent). Such proteins and such antagonists can also be used to prevent or treat coeliac disease. The antagonist will cause a decrease in the T cell response. In one embodiment the antagonist binds the TCR of the T cell (generally in the form of a complex with HLA-DQ2) but instead of causing normal functional activation causing an abnormal signal to be passed through the TCR intracellular signalling cascade which causes the T cell to have decreased function activity (e.g. in response to recognition of an epitope, typically as measured by any suitable assay mentioned herein).

In one embodiment the antagonist competes with epitope to bind a component of MHC processing and presentation pathway, such as an MHC molecule (typically HLA-DQ2). Thus the antagonist may bind HLA-DQ2 (and thus be a peptide presented by this MHC molecule), such as peptide TP (Table 10) or a homologue thereof.

Methods of causing antagonism are known in the art. In one embodiment the antagonist is a homologue of the epitopes mentioned above and may have any of the sequence, binding or other properties of the agent (particularly analogues). The antagonists typically differ from any of the above epitopes (which are capable of causing a normal antigen specific function in the T cell) by 1, 2, 3, 4 or more mutations (each of which may be a substitution, insertion or deletion). Such antagonists are termed "altered peptide ligands" or "APL" in the art. The mutations are typically at the amino acid positions which contact the TCR.

The antagonist may differ from the epitope by a substitution within the sequence which is equivalent to the sequence represented by amino acids 65 to 67 of A-gliadin (such antagonists are shown in Table 9). Thus preferably the antagonist has a substitution at the equivalent of position 64, 65 or 67. Preferably the substitution is 64W, 67W, 67M or 65T.

Since the T cell immune response to the epitope of the invention in an individual is polyclonal more than one antagonist may need to be administered to cause antagonism of T cells of the response which have different TCRs. Therefore the antagonists may be administered in a composition which comprises at least 2, 4, 6 or more different antagonists, which each antagonise different T cells.

The invention also provides a method of identifying an antagonist of a T cell (which recognises the agent) comprising contacting a candidate substance with the T cell and detecting whether the substance causes a decrease in the ability of the T cell to undergo an antigen specific response (e.g. using any suitable assay mentioned herein), the detecting of any such decrease in said ability indicating that the substance is an antagonist.

In one embodiment the antagonists (including combinations of antagonists to a particular epitope) or tolerising (T cell and antibody tolerising) agents are present in a composition comprising at least 2, 4, 6 or more antagonists or agents which antagonise or tolerise to different epitopes of the invention, for example to the combinations of epitopes discussed above in relation to the agents which are a product comprising more than one substance.

Testing Whether a Composition is Capable of Causing Coeliac Disease

As mentioned above the invention provides a method of determining whether a composition is capable of causing coeliac disease comprising detecting the presence of a protein sequence which is capable of being modified by a transglutaminase to as sequence comprising the agent or epitope of the invention (such transglutaminase activity may be a human intestinal transglutaminase activity). Typically this is performed by using a binding assay in which a moiety which binds to the sequence in a specific manner is contacted with the composition and the formation of sequence/moiety complex is detected and used to ascertain the presence of the agent. Such a moiety may be any suitable substance (or type of substance) mentioned herein, and is typically a specific antibody. Any suitable format of binding assay can be used (such as those mentioned herein).

In one embodiment the composition is contacted with at least 2, 5, 10 or more antibodies which are specific for epitopes of the invention from different gliadins, for example a panel of antibodies capable of recognising the combinations of epitopes discussed above in relation to agents of the invention which are a product comprising more than one substance.

The composition typically comprises material from a plant that expresses a gliadin which is capable of causing coeliac disease (for example any of the gliadins or plants mentioned herein). Such material may be a plant part, such as a harvested product (e.g. seed). The material may be processed products of the plant material (e.g. any such product mentioned herein), such as a flour or food that comprises the gliadin. The processing of food material and testing in suitable binding assays is routine, for example as mentioned in Kricka L J, J. Biolumin. Chemilumin. 13, 189–93 (1998).

Binding Assays

The determination of binding between any two substances mentioned herein may be done by measuring a characteristic of either or both substances that changes upon binding, such as a spectroscopic change.

The binding assay format may be a 'band shift' system. This involves determining whether the presence of one substance (such as a candidate substance) advances or retards the progress of the other substance during gel electrophoresis.

The format may be a competitive binding method which determines whether the one substance is able to inhibit the binding of the other substance to an agent which is known to bind the other substance, such as a specific antibody.

Mutant Gliadin Proteins

The invention provides a gliadin protein in which an epitope sequence of the invention, or sequence which can be modified by a transglutaminase to provide such a sequence has been mutated so that it no longer causes, or is recognised by, a T cell response that recognises the epitope. In this context the term recognition refers to the TCR binding the epitope in such a way that normal (not antagonistic) antigen-specific functional activity of the T cell occurs.

Methods of identifying equivalent epitopes in other gliadins are discussed above. The wild type of the mutated gliadin is one which causes coeliac disease. Such a gliadin will have homology with SEQ D NO:3, for example to the degree mentioned above (in relation to the analogue) across all of SEQ ID NO:3 or across 15, 30, 60, 100 or 200 contiguous amino acids of SEQ ID NO:3.

The mutated gliadin will not cause coeliac disease or will cause decreased symptoms of coeliac disease. Typically the mutation decreases the ability of the epitope to induce a T cell response. The mutated epitope may have a decreased binding to HLA-DQ2, a decreased ability to be presented by an APC or a decreased ability to bind to or to be recognised (i.e. cause antigen-specific functional activity) by T cells that recognise the agent. The mutated gliadin or epitope will therefore show no or reduced recognition in any of the assays mentioned herein in relation to the diagnostic aspects of the invention.

The mutation may be one or more deletions, additions or substitutions of length 1 to 3, 4 to 6, 6 to 10, 11 to 15 or more in the epitope, for example across the sequence SEQ ID NO:2 or its equivalent. Preferably the mutant gliadin has at least one mutation in the sequence SEQ ID NO:1. A preferred mutation is at position 65 in A-gliadin (or in an equivalent position in other gliadins). Typically the naturally occurring glutamine at this position is substituted to any of the amino acids shown in Table 3, preferably to histidine, tyrosine, tryptophan, lysine, proline, or arginine.

The invention thus also provides use of a mutation (such any of the mutations in any of the sequences discussed herein) in an epitope of a gliadin protein, which epitope is an epitope of the invention, to decrease the ability of the gliadin protein to cause coeliac disease.

In one embodiment the mutated sequence is able to act as an antagonist. Thus the invention provides a protein that comprises a sequence which is able to bind to a T cell receptor, which T cell receptor recognises an agent of the invention, and which sequence is able to cause antagonism of a T cell that carries such a T cell receptor.

The invention also provides proteins which are fragments of the above mutant gliadin proteins, which are at least 15 amino acids long (e.g. at least 30, 60, 100, 150, 200, or 250 amino acids long) and which comprise the mutations discussed above which decrease the ability of the gliadin to be recognised. Any of the mutant proteins (including fragments) mentioned herein may also be present in the form of fusion proteins, for example with other gliadins or with non-gliadin proteins.

The equivalent wild type protein to the mutated gliadin protein is typically from a graminaceous monocotyledon, such as a plant of genus *Triticum*, e.g. wheat, rye, barley, oats or triticale. The protein is typically an α, αβ, β, γ or ω gliadin. The gliadin may be an A-gliadin.

Kits

The invention also provides a kit for carrying out the method comprising one or more agents and optionally a means to detect the recognition of the agent by the T cell. Typically the different agents are provided for simultaneous, separate or sequential use. Typically the means to detect recognition allows or aids detection based on the techniques discussed above.

Thus the means may allow detection of a substance secreted by the T cells after recognition. The kit may thus additionally include a specific binding moiety for the substance, such as an antibody. The moiety is typically specific for IFN-γ. The moiety is typically immobilised on a solid support. This means that after binding the moiety the substance will remain in the vicinity of the T cell which secreted it. Thus 'spots' of substance/moiety complex are formed on the support, each spot representing a T cell which is secreting the substance. Quantifying the spots, and typically comparing against a control, allows determination of recognition of the agent.

The kit may also comprise a means to detect the substance/moiety complex. A detectable change may occur in the moiety itself after binding the substance, such as a colour change. Alternatively a second moiety directly or indirectly labelled for detection may be allowed to bind the substance/moiety complex to allow the determination of the spots. As discussed above the second moiety may be specific for the substance, but binds a different site on the substance than the first moiety.

The immobilised support may be a plate with wells, such as a microtitre plate. Each assay can therefore be carried out in a separate well in the plate.

The kit may additionally comprise medium for the T cells, detection moieties or washing buffers to be used in the detection steps. The kit may additionally comprise reagents suitable for the separation from the sample, such as the separation of PBMCs or T cells from the sample. The kit may be designed to allow detection of the T cells directly in the sample without requiring any separation of the components of the sample.

The kit may comprise an instrument which allows administration of the agent, such as intradermal or epidermal administration. Typically such an instrument comprises plaster, dressing or one or more needles. The instrument may allow ballistic delivery of the agent. The agent in the kit may be in the form of a pharmaceutical composition.

The kit may also comprise controls, such as positive or negative controls. The positive control may allow the detection system to be tested. Thus the positive control typically mimics recognition of the agent in any of the above methods. Typically in the kits designed to determine recognition in vitro the positive control is a cytokine. In the kit designed to detect in vivo recognition of the agent the positive control may be antigen to which most individuals should response.

The kit may also comprise a means to take a sample containing T cells from the host, such as a blood sample. The kit may comprise a means to separate mononuclear cells or T cells from a sample from the host.

Polynucleotides, Cells, Transgenic Mammals and Antibodies

The invention also provides a polynucleotide which is capable of expression to provide the agent or mutant gliadin proteins. Typically the polynucleotide is DNA or RNA, and is single or double stranded. The polynucleotide will preferably comprise at least 50 bases or base pairs, for example 50 to 100, 100 to 500, 500 to 1000 or 1000 to 2000 or more bases or base pairs. The polynucleotide therefore comprises sequence which encodes the sequence of SEQ ID NO: 1 or 2 or any of the agents mentioned herein. To the 5' and 3' of this coding sequence the polynucleotide of the invention has sequence or codons which are different from the sequence or codons 5' and 3' to these sequences in the corresponding gliadin gene.

5' and/or 3' to the sequence encoding the peptide the polynucleotide has coding or non-coding sequence. Sequence 5' and/or 3' to the coding sequence may comprise sequences which aid expression, such as transcription and/or translation, of the sequence encoding the agent. The polynucleotide may be capable of expressing the agent prokaryotic or eukaryotic cell. In one embodiment the polynucleotide is capable of expressing the agent in a mammalian cell, such as a human, primate or rodent (e.g. mouse or rat) cell.

A polynucleotide of the invention may hybridise selectively to a polynucleotide that encodes SEQ ID NO:3 at a level significantly above background. Selective hybridisation is typically achieved using conditions of medium to high stringency (for example 0.03M sodium chloride and 0.03M sodium citrate at from about 50° C. to about 60° C.). However, such hybridisation may be carried out under any suitable conditions known in the art (see Sambrook et al (1989), Molecular Cloning: A Laboratory Manual). For example, if high stringency is required, suitable conditions include 0.2×SSC at 60° C. If lower stringency is required, suitable conditions include 2×SSC at 60° C.

Agents or proteins of the invention may be encoded by the polynucleotides described herein.

The polynucleotide may form or be incorporated into a replicable vector. Such a vector is able to replicate in a suitable cell. The vector may be an expression vector. In such a vector the polynucleotide of the invention is operably linked to a control sequence which is capable of providing for the expression of the polynucleotide. The vector may contain a selectable marker, such as the ampicillin resistance gene.

The polynucleotide or vector may be present in a cell. Such a cell may have been transformed by the polynucleotide or vector. The cell may express the agent. The cell will be chosen to be compatible with the said vector and may for example be a prokaryotic (bacterial), yeast, insect or mammalian cell. The polynucleotide or vector may be introduced into host cells using conventional techniques including calcium phosphate precipitation, DEAE-dextran transfection, or electroporation.

The invention provides processes for the production of the proteins of the invention by recombinant means. This may comprise (a) cultivating a transformed cell as defined above under conditions that allow the expression of the protein; and preferably (b) recovering the expressed polypeptide. Optionally, the polypeptide may be isolated and/or purified, by techniques known in the art.

The invention also provides TCRs which recognise (or bind) the agent, or fragments thereof which are capable of such recognition (or binding). These can be present in the any form mentioned herein (e.g. purity) discussed herein in relation to the protein of the invention. The invention also provides T cells which express such TCRs which can be present in any form (e.g. purity) discussed herein for the cells of the invention.

The invention also provides monoclonal or polyclonal antibodies which specifically recognise the agents (such as any of the epitopes of the invention) and which recognise the mutant gliadin proteins (and typically which do not recognise the equivalent wild-type gliadins) of the invention, and methods of making such antibodies. Antibodies of the invention bind specifically to these substances of the invention.

For the purposes of this invention, the term "antibody" includes antibody fragments such as Fv, F(ab) and F(ab)$_2$ fragments, as well as single-chain antibodies.

A method for producing a polyclonal antibody comprises immunising a suitable host animal, for example an experimental animal, with the immunogen and isolating immunoglobulins from the serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein (1975) Nature 256, 495497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

The polynucleotide, agent, protein or antibody of the invention, may carry a detectable label. Detectable labels which allow detection of the secreted substance by visual inspection, optionally with the aid of an optical magnifying means, are preferred. Such a system is typically based on an enzyme label which causes colour change in a substrate, for example alkaline phosphatase causing a colour change in a substrate. Such substrates are commercially available, e.g. from BioRad. Other suitable labels include other enzymes such as peroxidase, or protein labels, such as biotin; or radioisotopes, such as $^{32}P$ or $^{35}S$. The above labels may be detected using known techniques.

Polynucleotides, agents, proteins, antibodies or cells of the invention may be in substantially purified form. They may be in substantially isolated form, in which case they will generally comprise at least 80% e.g. at least 90, 95, 97 or 99% of the polynucleotide, peptide, antibody, cells or dry mass in the preparation. The polynucleotide, agent, protein or antibody is typically substantially free of other cellular components. The polynucleotide, agent, protein or antibody may be used in such a substantially isolated, purified or free form in the method or be present in such forms in the kit.

The invention also provides a transgenic mammal which expresses a TCR of the invention. This may be any of the mammals discussed herein (e.g. in relation to the production of the antibody). Preferably the mammal has, or is susceptible, to coeliac disease. The mammal may also express HLA-DQ2 and/or may be given a diet comprising a gliadin which cause coeliac disease (e.g. any of the gliadin proteins mentioned herein). Thus the mammal may act as an animal model for coeliac disease.

The invention also provides a method of identifying a product which is therapeutic for coeliac disease comprising administering a candidate substance to a mammal of the invention which has, or which is susceptible to, coeliac disease and determining whether substance prevents or treats coeliac disease in the mammal, the prevention or treatment of coeliac disease indicating that the substance is a therapeutic product. Such a product may be used to treat or prevent coeliac disease.

The invention provides therapeutic (including prophylactic) agents or diagnostic substances (the agents, proteins and polynucleotides of the invention). These substances are formulated for clinical administration by mixing them with a pharmaceutically acceptable carrier or diluent. For example they can be formulated for topical, parenteral, intravenous, intramuscular, subcutaneous, intraocular, intradermal, epidermal or transdermal administration. The substances may be mixed with any vehicle which is pharmaceutically acceptable and appropriate for the desired route of administration. The pharmaceutically carrier or diluent for injection may be, for example, a sterile or isotonic solution such as Water for Injection or physiological saline, or a carrier particle for ballistic delivery.

The dose of the substances may be adjusted according to various parameters, especially according to the agent used; the age, weight and condition of the patient to be treated; the mode of administration used; the severity of the condition to be treated; and the required clinical regimen. As a guide, the amount of substance administered by injection is suitably from 0.01 mg/kg to 30 mg/kg, preferably from 0.1 mg/kg to 10 mg/kg.

The routes of administration and dosages described are intended only as a guide since a skilled practitioner will be able to determine readily the optimum route of administration and dosage for any particular patient and condition.

The substances of the invention may thus be used in a method of treatment of the human or animal body, or in a diagnostic method practised on the human body. In particular they may be used in a method of treating or preventing coeliac disease. The invention also provide the agents for use in a method of manufacture of a medicament for treating or preventing coeliac disease. Thus the invention provides a method of preventing or treating coeliac disease comprising administering to a human in need thereof a substance of the invention (typically a non-toxic effective amount thereof).

The agent of the invention can be made using standard synthetic chemistry techniques, such as by use of an automated synthesizer. The agent may be made from a longer polypeptide e.g. a fusion protein, which polypeptide typically comprises the sequence of the peptide. The peptide may be derived from the polypeptide by for example hydrolysing the polypeptide, such as using a protease; or by physically breaking the polypeptide. The polynucleotide of the invention can be made using standard techniques, such as by using a synthesiser.

Plant Cells and Plants that Express Mutant Gliadin Proteins or Express Proteins Comprising Sequences which can Act as Antagonists The cell of the invention may be a plant cell, such as a cell of a graminaceous monocotyledonous species. The species may be one whose wild-type form expresses gliadins, such as any of the gliadin proteins mentioned herein (including gliadins with any degree of homology to SEQ ID NO:3 mentioned herein). Such a gliadin may cause coeliac disease in humans. The cell may be of wheat, maize, oats, rye, rice, barley, triticale, sorghum, or sugar cane. Typically the cell is of the *Triticum* genus, such as aestivum, spelta, polonicum or monococcum.

The plant cell of the invention is typically one which does not express a wild-type gliadin (such as any of the gliadins mentioned herein which may cause coeliac disease), or one which does not express a gliadin comprising a sequence that can be recognised by a T cell that recognises the agent. Thus if the wild-type plant cell did express such a gliadin then it may be engineered to prevent or reduce the expression of such a gliadin or to change the amino acid sequence of the gliadin so that it no longer causes coeliac disease (typically by no longer expressing the epitope of the invention).

This can be done for example by introducing mutations into 1, 2, 3 or more or all of such gliadin genes in the cell, for example into coding or non-coding (e.g. promoter) regions). Such mutations can be any of the type or length of mutations discussed herein (e.g in relation to homologous proteins). The mutations can be introduced in a directed manner (e.g using site directed mutagenesis or homologous recombination techniques) or in a random manner (e.g. using a mutagen, and then typically selecting for mutagenised cells which no longer express the gliadin (or a gliadin sequence which causes coeliac disease)).

In the case of plants or plant cells that express a protein that comprises a sequence able to act as an antagonist such a plant or plant cell may express a wild-type gliadin protein (e.g. one which causes coeliac disease). Preferably though the presence of the antagonist sequence will cause reduced coeliac disease symptoms (such as no symptoms) in an individual who ingests a food comprising protein from the plant or plant cell.

The polynucleotide which is present in (or which was transformed into) the plant cell will generally comprise promoter capable of expressing the mutant gliadin protein the plant cell. Depending on the pattern of expression desired, the promoter may be constitutive, tissue- or stage-specific; and/or inducible. For example, strong constitutive expression in plants can be obtained with the CAMV 35S, Rubisco ssu, or histone promoters. Also, tissue-specific or stage-specific promoters may be used to target expression of protein of the invention to particular tissues in a transgenic plant or to particular stages in its development. Thus, for example seed-specific, root-specific, leaf-specific, flower-specific etc promoters may be used. Seed-specific promoters include those described by Dalta et al (Biotechnology Ann. Rev. (1997), 3, pp. 269–296). Particular examples of seed-specific promoters are napin promoters (EP-A-0 255, 378), phaseolin promoters, glutenine promoters, helianthenine promoters (WO92/17580), albumin promoters (WO98/45460), oleosin promoters (WO98/45461) and ATS1 and ATS3 promoters (PCT/US98/06798).

The cell may be in any form. For example, it may be an isolated cell e.g. a protoplast, or it may be part of a plant tissue, e.g. a callus, or a tissue excised from a plant, or it may be part of a whole plant. The cell may be of any type (e.g of any type of plant part). For example, an undifferentiated cell, such as a callus cell; or a differentiated cell, such as a cell of a type found in embryos, pollen, roots, shoots or leaves. Plant parts include roots; shoots; leaves; and parts involved in reproduction, such as pollen, ova, stamens, anthers, petals, sepals and other flower parts.

The invention provides a method of obtaining a transgenic plant cell comprising transforming a plant cell with a polynucleotide or vector of the invention to give a transgenic plant cell. Any suitable transformation method may be used (in the case of wheat the techniques disclosed in Vasil V et al, Biotechnology 10, 667–674 (1992) may be used). Preferred transformation techniques include electroporation of plant protoplasts and particle bombardment. Transformation may thus give rise to a chimeric tissue or plant in which some cells are transgenic and some are not.

The cell of the invention or thus obtained cell may be regenerated into a transgenic plant by techniques known in the art. These may involve the use of plant growth substances such as auxins, giberellins and/or cytokinins to stimulate the growth and/or division of the transgenic cell. Similarly, techniques such as somatic embryogenesis and meristem culture may be used. Regeneration techniques are well known in the art and examples can be found in, e.g. U.S. Pat. No. 4,459,355, U.S. Pat. No. 4,536,475, U.S. Pat. No. 5,464,763, U.S. Pat. No. 5,177,010, U.S. Pat. No. 5,187,073, EP 267,159, EP 604, 662, EP 672, 752, U.S. Pat. No. 4,945,050, U.S. Pat. No. 5,036,006, U.S. Pat. No. 5,100,792, U.S. Pat. No. 5,371,014, U.S. Pat. No. 5,478,744, U.S. Pat. No. 5,179,022, U.S. Pat. No. 5,565,346, U.S. Pat. No. 5,484,956, U.S. Pat. No. 5,508,468, U.S. Pat. No. 5,538,877, U.S. Pat. No. 5,554,798, U.S. Pat. No. 5,489,520, U.S. Pat. No. 5,510,318, U.S. Pat. No. 5,204,253, U.S. Pat. No. 5,405,765, EP 442,174, EP 486,233, EP 486,234, EP 539,563, EP 674,725, WO91/02071 and WO 95/06128.

In many such techniques, one step is the formation of a callus, i.e. a plant tissue comprising expanding and/or dividing cells. Such calli are a further aspect of the invention as are other types of plant cell cultures and plant parts. Thus, for example, the invention provides transgenic plant tissues and parts, including embryos, meristems, seeds, shoots, roots, stems, leaves and flower parts. These may be chimeric in the sense that some of their cells are cells of the invention and some are not. Transgenic plant parts and tissues, plants and seeds of the invention may be of any of the plant species mentioned herein.

Regeneration procedures will typically involve the selection of transformed cells by means of marker genes.

The regeneration step gives rise to a first generation transgenic plant. The invention also provides methods of obtaining transgenic plants of further generations from this first generation plant. These are known as progeny transgenic plants. Progeny plants of second, third, fourth, fifth, sixth and further generations may be obtained from the first generation transgenic plant by any means known in the art.

Thus, the invention provides a method of obtaining a transgenic progeny plant comprising obtaining a second-generation transgenic progeny plant from a first-generation transgenic plant of the invention, and optionally obtaining transgenic plants of one or more further generations from the second-generation progeny plant thus obtained.

Progeny plants may be produced from their predecessors of earlier generations by any known technique. In particular, progeny plants may be produced by:

obtaining a transgenic seed from a transgenic plant of the invention belonging to a previous generation, then obtaining a transgenic progeny plant of the invention belonging to a new generation by growing up the transgenic seed; and/or propagating clonally a transgenic plant of the invention belonging to a previous generation to give a transgenic progeny plant of the invention belonging to a new generation; and/or crossing a first-generation transgenic plant of the invention belonging to a previous generation with another compatible plant to give a transgenic progeny plant of the invention belonging to a new generation; and optionally obtaining transgenic progeny plants of one or more further generations from the progeny plant thus obtained.

These techniques may be used in any combination. For example, clonal propagation and sexual propagation may be used at different points in a process that gives rise to a transgenic plant suitable for cultivation. In particular, repetitive back-crossing with a plant taxon with agronomically desirable characteristics may be undertaken. Further steps of removing cells from a plant and regenerating new plants therefrom may also be carried out.

Also, further desirable characteristics may be introduced by transforming the cells, plant tissues, plants or seeds, at any suitable stage in the above process, to introduce desirable coding sequences other than the polynucleotides of the invention. This may be carried out by the techniques described herein for the introduction of polynucleotides of the invention.

For example, further transgenes may be selected from those coding for other herbicide resistance traits, e.g. tolerance to: Glyphosate (e.g. using an EPSP synthase gene (e.g. EP-A-0 293,358) or a glyphosate oxidoreductase (WO 92/000377) gene); or tolerance to fosametin; a dihalobenzonitrile; glufosinate, e.g. using a phosphinothrycin acetyl transferase (PAT) or glutamine synthase gene (cf. EP-A-0 242,236); asulam; e.g. using a dihydropteroate synthase gene (EP-A-0 369,367); or a sulphonylurea, e.g. using an ALS gene); diphenyl ethers such as acifluorfen or oxyfluorfen, e.g. using a protoporphyrogen oxidase gene); an oxadiazole such as oxadiazon; a cyclic imide such as chlorophthalim; a phenyl pyrazole such as TNP, or a phenopylate or carbamate analogue thereof.

Similarly, genes for beneficial properties other than herbicide tolerance may be introduced. For example, genes for insect resistance may be introduced, notably genes encoding *Bacillus thuringiensis* (Bt) toxins. Likewise, genes for disease resistance may be introduced, e.g. as in WO91/02701 or WO95/06128.

Typically, a protein of the invention is expressed in a plant of the invention Depending on the promoter used, this expression may be constitutive or inducible. Similarly, it may be tissue- or stage-specific, i.e. directed towards a particular plant tissue (such as any of the tissues mentioned herein) or stage in plant development.

The invention also provides methods of obtaining crop products by harvesting, and optionally processing further, transgenic plants of the invention. By crop product is meant any useful product obtainable from a crop plant.

Products that Contain Mutant Gliadin Proteins or Proteins that Comprise Sequence Capable of Acting as an Antagonist The invention provides a product that comprises the mutant gliadin proteins or protein that comprises sequence capable of acting as an antagonist. This is typically derived from or comprise plant parts from plants mentioned herein which express such proteins. Such a product may be obtainable directly by harvesting or indirectly, by harvesting and further processing the plant of the invention. Directly obtainable products include grains. Alternatively, such a product may be obtainable indirectly, by harvesting and further processing. Examples of products obtainable by further processing are flour or distilled alcoholic beverages; food products made from directly obtained or further processed material e.g. baked products (e.g. bread) made from flour. Typically such food products, which are ingestible and digestible (i.e. non-toxic and of nutrient value) by human individuals.

In the case of food products that comprise the protein which comprises an antagonist sequence the food product may also comprise wild-type gliadin, but preferably the antagonist is able to cause a reduction (e.g. completely) in the coeliac disease symptoms after such food is ingested.

The invention is illustrated by the following Examples:

EXAMPLE 1

We carried out epitope mapping in Coeliac disease by using a set of 51 synthetic 15-mer peptides that span the complete sequence of a fully characterized a-gliadin, "A-gliadin" (see Table 1). A-Gliadin peptides were also individually treated with tTG to generate products that might mimic those produced in vivo[3]. We also sought to study Coeliac disease patients at the point of initiation of disease relapse to avoid the possibility that epitope "spreading"or "exhaustion" may have occurred, as described in experimental infectious and autoimmune diseases.

Clinical and A-Gliadin Specific T Cell Responses with 3 and 10 Day Bread Challenge In a pilot study, two subjects with Coeliac disease in remission, defined by absence of serum anti-endomysial antibody (EMA), on a gluten free diet were fed four slices of standard gluten-containing white bread daily in addition to their usual gluten free diet. Subject 1 ceased bread because of abdominal pain, mouth ulcers and mild diarrhoea after three days, but Subject 2 continued for 10 days with only mild nausea at one week. The EMA became positive in Subject 2 one week after the bread challenge, indicating the bread used had caused a relapse of Coeliac disease. But in Subject 1, EMA remained negative up to two months after bread challenge. In both subjects, symptoms that appeared with bread challenge resolved within two days after returning to gluten free diet.

PBMC responses in IFNγ ELISPOT assays to A-gliadin peptides were not found before or during bread challenge. But from the day after bread withdrawal (Day 4) in Subject 1 a single pool of 5 overlapping peptides spanning A-gliadin 51–85 (Pool 3) treated with tTG showed potent IFNg responses (see FIG. 1a). In Subject 1, the PBMC IFNg response to A-gliadin peptide remained targeted to Pool 3 alone and was maximal on Day 8. The dynamics and magnitude of the response to Pool 3 was similar to that elicited by a-chymotrypsin digested gliadin. PBMC IFNγ responses to tTG-treated Pool 3 were consistently 5 to 12-fold greater than Pool 3 not treated with tTG, and responses to α-chymotrypsin digested gliadin were 3 to 10-fold greater if treated with tTG. In Subject 2, Pool 3 treated with tTG was also the only immunogenic set of A-gliadin peptides on Day 8, but this response was weaker than Subject 1, was not seen on Day 4 and by Day 11 the response to Pool 3 had diminished and other tTG-treated pools of A-gliadin peptides elicited stronger IFNα responses (see FIG. 1b).

The pilot study indicated that the initial T cell response in these Coeliac disease subjects was against a single tTG-treated A-gliadin pool of five peptides and was readily measured in peripheral blood. But if antigen exposure is continued for ten days instead of three, T cell responses to other A-gliadin peptides appear, consistent with epitope spreading.

Coeliac Disease-Specific IFN-g Induction by tTG-Treated A-Gliadin Peptides

Figure 2A:
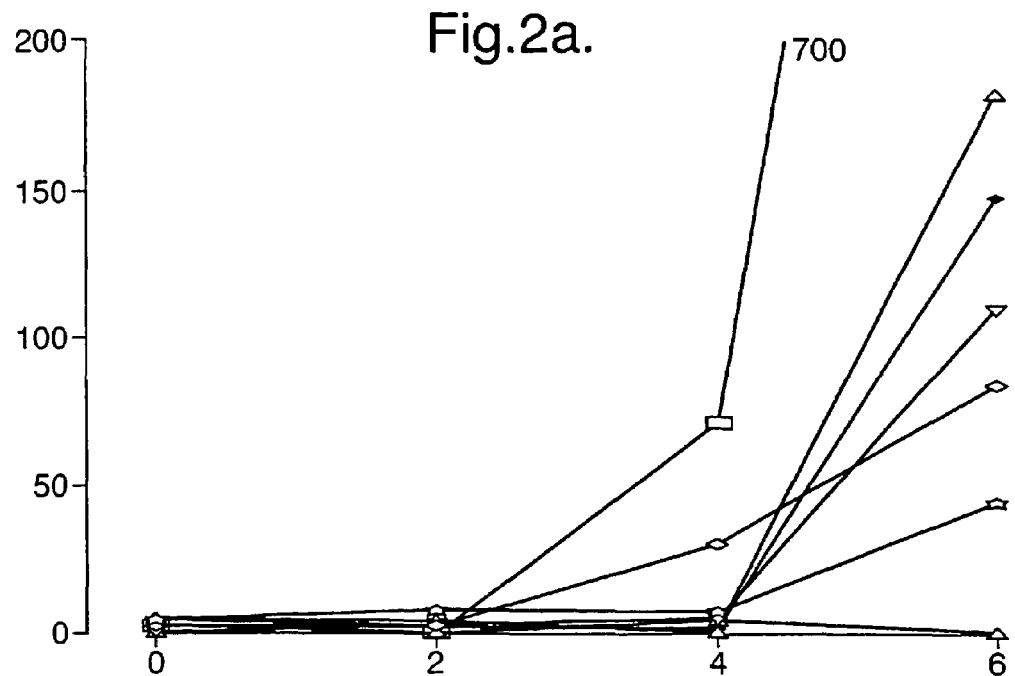
Figure 2B:
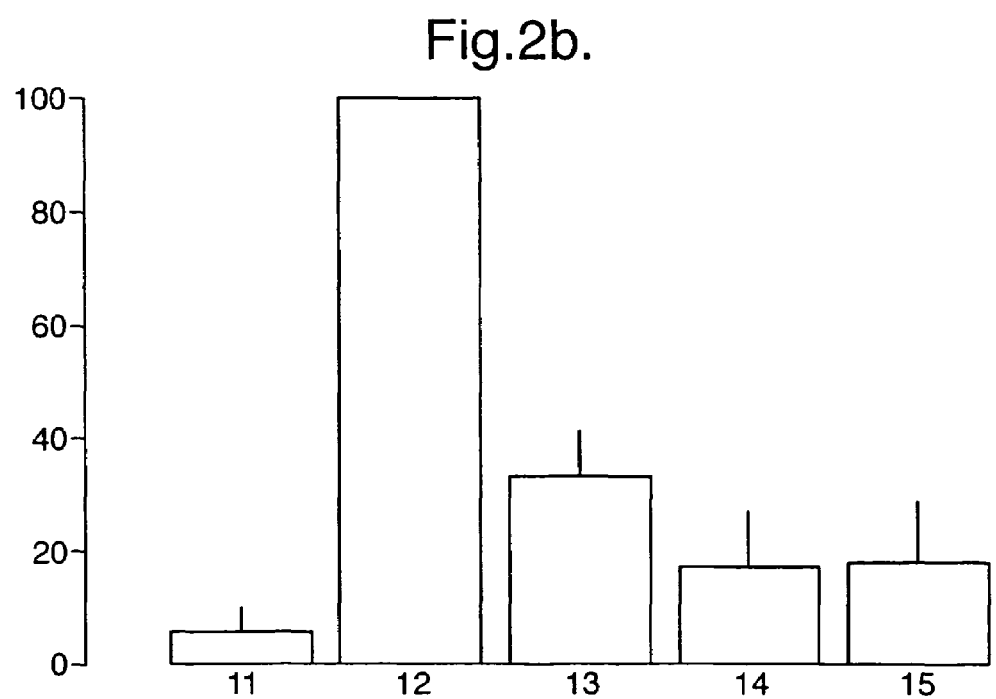

In five out of six further Coeliac disease subjects on gluten free diet (see Table 1), bread challenge for three days identified tTG-treated peptides in Pool 3, and in particular, peptides corresponding to 56–70 (12) and 60–75 (13) as the sole A-gliadin components eliciting IFNγ from PBMC (see FIG. 2). IL-10 ELISPOT assays run in parallel to IFNγ ELISPOT showed no IL-10 response to tTG-treated peptides 12 or 13. In one subject, there were no IFNγ responses to any A-gliadin peptide or α-chymotrypsin digested gliadin before, during or up to four days after bread challenge. In none of these Coeliac disease subjects did EMA status change from baseline when measured for up to two months after bread challenge.

PBMC from four healthy, EMA-negative subjects with the HLA-DQ alleles α1*0501, β1*0201 (ages 28–52, 2 females) who had been challenged for three days with bread after following a gluten free diet for one month, showed no IFNγ responses above the negative control to any of the A-gliadin peptides with or without tTG treatment. Thus, induction of IFNγ in PBMC to tTG-treated Pool 3 and A-gliadin peptides 56–70 (12) and 60–75 (13) were Coeliac disease specific (7/8 vs 0/4, p<0.01 by Chi-squared analysis).

Figure 4A:
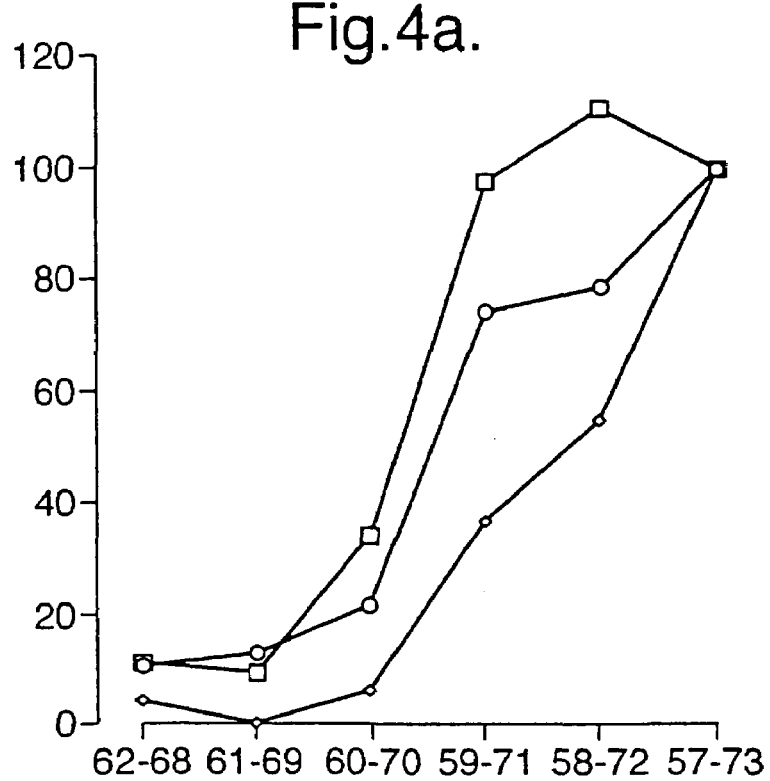
Figure 4B:
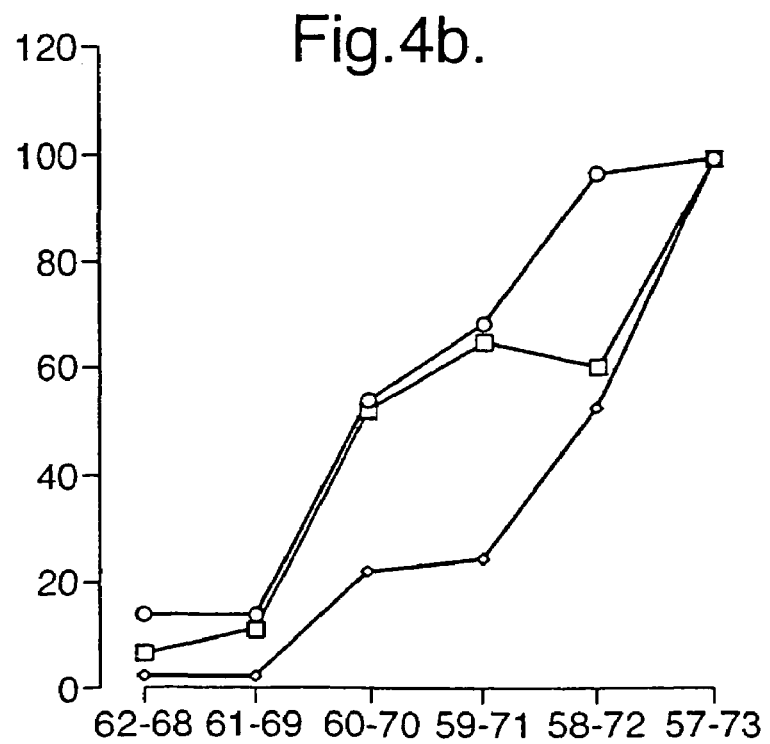

Fine Mapping of the Minimal A-Gliadin T Cell Epitope tTG-treated peptides representing truncations of A-gliadin 56–75 revealed that the same core peptide sequence (QPQLP) was essential for antigenicity in all of the five Coeliac disease subjects assessed (see FIG. 3). PBMC IFNγ responses to tTG-treated peptides spanning this core sequence beginning with the 7-mer PQPQLPY and increasing in length, indicated that the tTG-treated 17-mer QLQPF- PQPQLPYPQPQS (A-gliadin 57–73) possessed optimal activity in the IFNγ ELISPOT (see FIG. 4).

Figure 5:
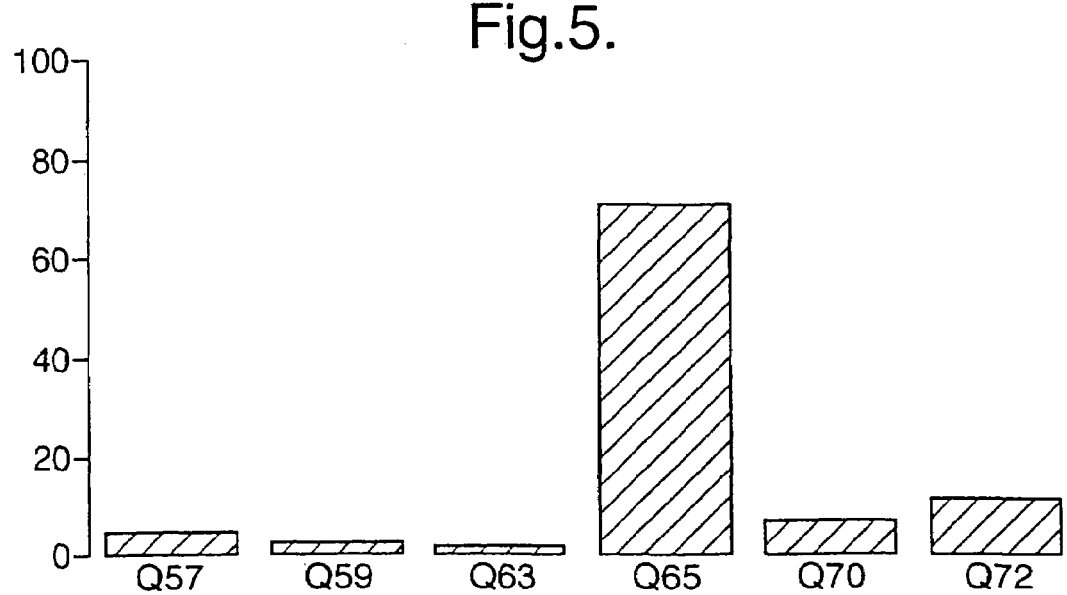
Figure 6:
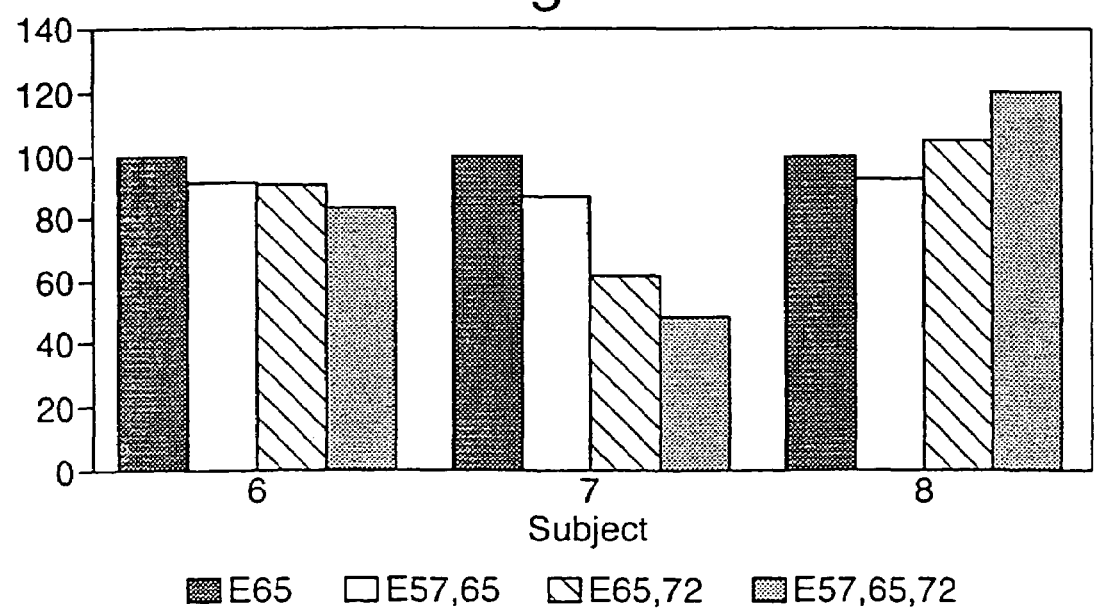

Deamidation of Q65 by tTG Generates the Immunodominant T Cell Epitope in A-Gliadin HPLC analysis demonstrated that tTG treatment of A-gliadin 56–75 generated a single product that eluted marginally later than the parent peptide. Amino acid sequencing indicated that out of the six glutanmine (Q) residues contained in A-gliadin 56–75, Q65 was preferentially deamidated by tTG (see FIG. 5). Bioactivity of peptides corresponding to serial expansions from the core A-gliadin 62–68 sequence in which glutamate (E) replaced Q65, was equivalent to the same peptides with Q65 after tTG-treatment (see FIG. 4a). Replacement of Q57 and Q72 by E together or alone, with E65 did not enhance antigenicity of the 17-mer in the three Coeliac disease subjects studied (see FIG. 6). Q57 and Q72 were investigated because glutamine residues followed by proline in gliadin peptides are not deamidated by tTG in vitro (W. Vader et al, Proceedings 8th International Symposium Coeliac Disease). Therefore, the immunodominant T cell epitope was defined as QLQPFQPELPYPQPQS.

Immunodominant T Cell Epitope Response is DQ2-Restricted and CD4 Dependent

Figure 7A:
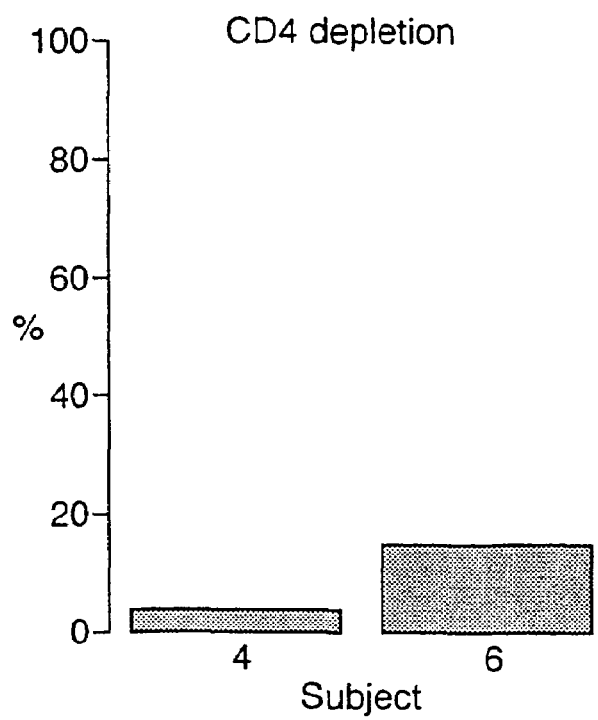
Figure 7B:
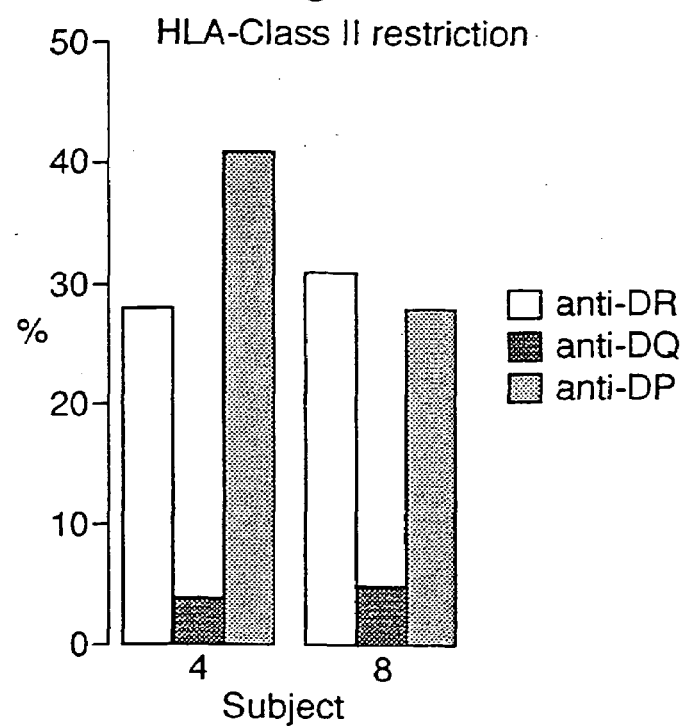

In two Coeliac disease subjects homozygous for HLA-DQ α1*0501, β1*0201, anti-DQ monoclonal antibody blocked the ELISPOT IFNγ response to tTG-treated A-gliadin 56–75, but anti-DP and -DR antibody did not (see FIG. 7). Anti-CD4 and anti-CD8 magnetic bead depletion of PBMC from two Coeliac disease subjects indicated the IFNγ response to tTG-treated A-gliadin 56–75 is CD4 T cell-mediated.

Discussion

In this study we describe a rather simple dietary antigen challenge using standard white bread to elicit a transient population of CD4 T cells in peripheral blood of Coeliac disease subjects responsive to a tTG-treated A-gliadin 17-mer with the sequence: QLQPFPQPELPYPQPQS (residues 57–73). The immune response to A-gliadin 56–75 (Q→E65) is restricted to the Coeliac disease-associated HLA allele, DQ α1*0501, β1*0201. Tissue transglutaminase action in vitro selectively deamidates Q65. Elicited peripheral blood IFNg responses to synthetic A-gliadin peptides with the substitution Q→E65 is equivalent to tTG-treated Q65 A-gliadin peptides; both stimulate up to 10-fold more T cells in the IFNg ELISPOT than unmodified Q65 A-gliadin peptides.

We have deliberately defined this Coeliac disease-specific T cell epitope using in vivo antigen challenge and short-term ex vivo immune assays to avoid the possibility of methodological artifacts that may occur with the use of T cell clones in epitope mapping. Our findings indicate that peripheral blood T cell responses to ingestion of gluten are rapid but short-lived and can be utilized for epitope mapping. In vivo antigen challenge has also shown there is a temporal hierarchy of immune responses to A-gliadin peptides; A-gliadin 57–73 modified by tTG not only elicits the strongest IFNg response in PBMC but it is also the first IFNg response to appear.

Because we have assessed only peptides spanning A-gliadin, there may be other epitopes in other gliadins of equal or greater importance in the pathogenesis of Coeliac disease. Indeed, the peptide sequence at the core of the epitope in A-gliadin that we have identified (PQPQLPY) is shared by several other gliadins (SwissProt and Trembl accession numbers: P02863, Q41528, Q41531, Q41533, Q9ZP09, P04722, P04724, P18573). However, A-gliadin peptides that have previously been shown to possess bioactivity in biopsy challenge and in vivo studies (for example: 31–43, 44–55, and 206–217)[4,5] did not elicit IFNg responses in PBMC following three day bread challenge in Coeliac disease subjects. These peptides may be "secondary" T cell epitopes that arise with spreading of the immune response.

EXAMPLE 2

The Effect on T Cell Recognition of Substitutions in the Immunodominant Epitope

Figure 8:
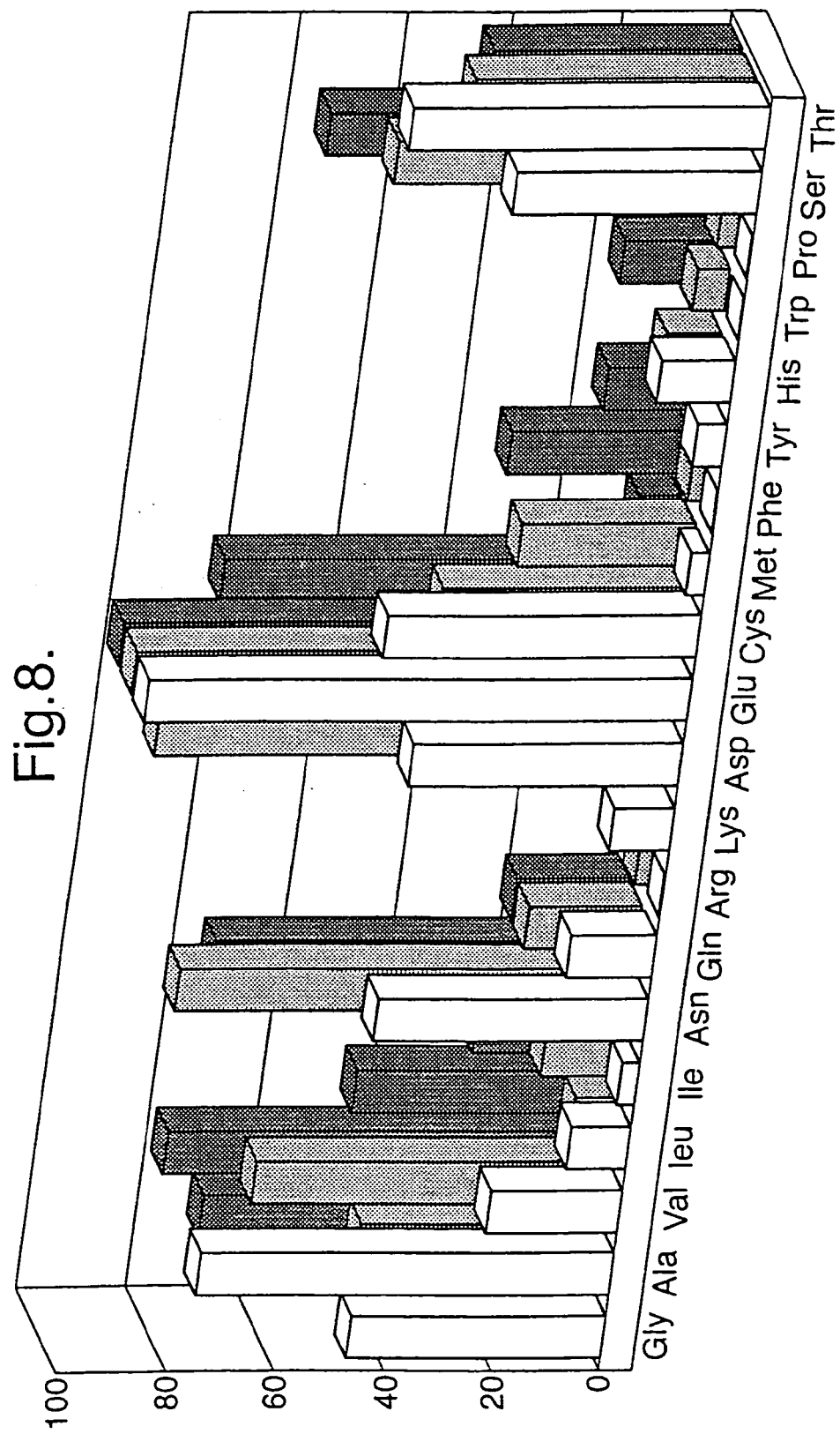
FIG. 8 shows the effect of substituting Glu at position 65 for other amino acids in the immunodominant epitope. The vertical axis shows the % response in the 3 subjects in relation to the immunodominant epitope.

The effect of substituting the glutamate at position 65 in the 57–73 A-gliadin epitope was determined by measuring peripheral blood responses against the substituted epitopes in an IFNγ ELISPOT assay using synthetic peptides (at 50 μg/ml). The responses were measured in 3 Coeliac disease subjects 6 days after commencing gluten challenge (4 slices bread daily for 3 days). Results are shown in table 3 and FIG. 8. As can be seen substitution of the glutamate to histidine, tyrosine, tryptophan, lysine, proline or arginine stimulated a response whose magnitude was less than 10% of the magnitude of the response to the immunodominant epitope. Thus mutation of A-gliadin at this position could be used to produce a mutant gliadin with reduce or absent immunoreactivity.

EXAMPLE 3

Figure 9:
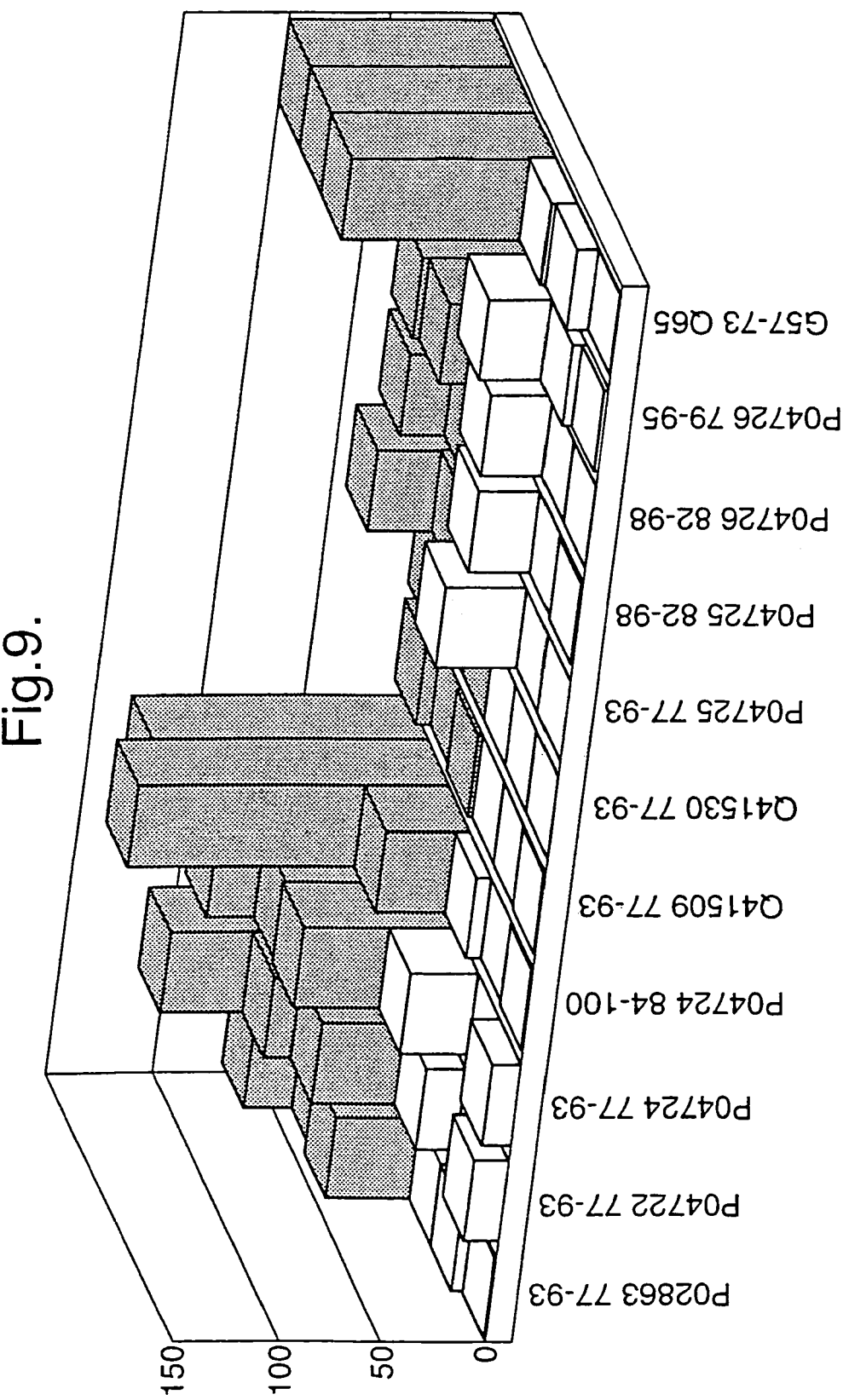
FIG. 9 shows the immunoreactivity of naturally occurring gliadin peptides (measuring responses from 3 subjects) which contain the sequence PQLPY with (shaded) and without (clear) transglutaminase treatment.

Testing the Immunoreactivity of Equivalent Peptides from Other Naturally Occurring Gliadins The immunoreactivity of equivalent peptides form other naturally occurring wheat gliadins was assessed using synthetic peptides corresponding to the naturally occurring sequences which were then treated with transglutaminase. These peptides were tested in an ELISPOT in the same manner and with PBMCs from the same subjects as described in Example 2. At least five of the peptides show immunoreactivity comparable to the A-gliadin 57–73 E65 peptide (after transglutaminase treatment) indicating that other gliadin proteins in wheat are also likely to induce this Coeliac disease-specific immune response (Table 4 and FIG. 9).

Methods

Subjects: Patients used in the study attended a Coeliac Clinic in Oxford, United Kingdom. Coeliac disease was diagnosed on the basis of typical small intestinal histology, and normalization of symptoms and small intestinal histology with gluten free diet.

Tissue typing: Tissue typing was performed using DNA extracted from EDTA-anticoagulated peripheral blood. HLA-DQA and DQB genotyping was performed by PCR using sequence-specific primer mixes[6-8].

Anti-endomysial antibody assay: EMA were detected by indirect immunofluorescence using patient serum diluted 1:5 with monkey oesophagus, followed by FITC-conjugated goat anti-human IgA. IgA was quantitated prior to EMA, none of the subjects were IgA deficient.

Antigen Challenge: Coeliac disease subjects following a gluten free diet, consumed 4 slices of gluten-containing bread (50 g/slice, Sainsbury's "standard white sandwich bread") daily for 3 or 10 days. EMA was assessed the week before and up to two months after commencing the bread challenge. Healthy subjects who had followed a gluten free diet for four weeks, consumed their usual diet including four slices of gluten-containing bread for three days, then returned to gluten free diet for a further six days.

IFNγ and IL-10 ELISPOT: PBMC were prepared from 50–100 ml of venous blood by Ficoll-Hypaque density centrifugation. After three washes, PBMC were resuspended in complete RPMI containing 10% heat inactivated human AB serum. ELISPOT assays for single cell secretion of IFNγ and IL-10 were performed using commercial kits (Mabtech; Stockholm, Sweden) with 96-well plates (MAIP-S-45; Millipore, Bedford, Mass.) according to the manufacturers instructions (as described elsewhere[9]) with $2-5 \times 10^5$ (IFNγ) or $0.4-1 \times 10^5$ (IL-10) PBMC in each well. Peptides were assessed in duplicate wells, and *Mycobacterium tuberculosis* purified protein derivative (PPD RT49) (Serum Institute; Copenhagen, Denmark) (20 μg/ml) was included as a positive control in all assays.

Peptides: Synthetic peptides were purchased from Research Genetics (Huntsville, Ala.) Mass-spectroscopy and HPLC verified peptides' authenticity and >70% purity. Digestion of gliadin (Sigma; G-3375) (100 mg/ml) with a-chymotrypsin (Sigma; C-3142) 200:1 (w/w) was performed at room temperature in 0.1 M $NH_4HCO_3$ with 2M urea and was halted after 24 h by heating to 98° C. for 10 minutes. After centrifugation (13 000 g, 10 minutes), the gliadin digest supernatant was filter-sterilized (0.2 mm). Digestion of gliadin was verified by SDS-PAGE and protein concentration assessed. α-Chymotrypsin-digested gliadin (640 μg/ml) and synthetic gliadin peptides (15-mers: 160 μg/ml, other peptides: 0.1 mM) were individually treated with tTG (Sigma; T-5398) (50 μg/ml) in $PBS+CaCl_2$ 1 mM for 2 h at 37° C. Peptides and peptide pools were aliquotted into sterile 96-well plates and stored frozen at −20° C. until use.

Amino acid sequencing of peptides: Reverse phase HPLC was used to purify the peptide resulting from tTG treatment of A-gliadin 56–75. A single product was identified and subjected to amino acid sequencing (automated sequencer Model 494A, Applied Biosystems, Foster City, Calif.). The sequence of unmodified G56–75 was confirmed as: LQLQPFQPQPQLPYPQPQPSFP, and tTG treated G56–75 was identified as: LQLQPFQPQPELPYPQPQPSFP. Deamidation of glutamyl residues was defined as the amount (pmol) of glutamate recovered expressed as a percent of the combined amount of glutamine and glutamate recovered in cycles 2, 4, 8, 10, 15 and 17 of the amino acid sequencing. Deamidation attributable to tTG was defined as (% deamidation of glutamine in the tTG treated peptide–% deamidation in the untreated peptide)/(100–% deamidation in the untreated peptide).

CD4/CD8 and HLA Class II Restriction: Anti-CD4 or anti-CD8 coated magnetic beads (Dynal, Oslo, Norway) were washed four times with RPMI then incubated with PBMC in complete RPMI containing 10% heat inactivated human AB serum ($5 \times 10^6$ cells/ml) for 30 minutes on ice. Beads were removed using a magnet and cells remaining counted. In vivo HLA-class II restriction of the immune response to tTG-treated A-gliadin 56–75 was established by incubating PBMC ($5 \times 10^6$ cells/ml) with anti-HLA-DR (L243), -DQ (L2), and -DP (B7.21) monoclonal antibodies (10 μg/ml) at room temperature for one hour prior to the addition of peptide.

EXAMPLE 4

Mucosal Integrin Expression by Gliadin-Specific Peripheral Blood Lymphocytes

Interaction between endothelial and lymphocyte adressins facilitates homing of organ-specific lymphocytes. Many adressins are known. The herterodimer $\alpha_4\beta_7$ is specific for lamina propria gut and other mucosal lymphocytes, and $\alpha^E\beta_7$ is specific and intra-epithelial lymphocytes in the gut and skin. Approximately 30% of perpheral blood CD4 T cells express $\alpha_4\beta_7$ and are presumed to be in transit to a mucosal site, while 5% of perpheral blood T cells express $\alpha^E\beta_7$. Immunomagnetic beads coated with antibody specifc for $\alpha^E$ or $\beta_7$ deplete PBMC of cells expressing $\alpha^E\beta_7$ or $\alpha^E\beta_7$ and $\alpha_4\beta_7$, respectively. In combination with ELISpot assay, immunomagnetic bead depletion allows determination of gliadin-specific T cell addressin expression that may identify these cells as homing to a mucosal surface. Interestingly, gluten challenge in vivo is associated with rapid influx of CD4T cells to the small intestinal lamina propria (not intra-epithelial sites), where over 90% lymphocytes express $\alpha_4\beta_7$.

Immunomagnetic beads were prepared and used to deplete PBMC from coeliac subjects on day 6 or 7 after commencing 3 day gluten challenge. FACS analysis demonstrated $\alpha^E$ beads depleted approximately 50% of positive CD4 T cells, while $\beta_7$ beads depleted all $\beta_7$ positive CD4 T cells. Depletion of PBMC using CD4- or $\beta_7$-beads, but not CD8- or $\beta^E$-beads, abolished responses in the interferon gamma ELISpot. tTG gliadin and PPD responses were abolished by CD4 depletion, but consistently affected by integrin-specific bead depletion.

Thus A-gliadin 57–73 QE65-specific T cells induced after gluten challenge in coeliac disease express the integrin, $\alpha_4\beta_7$, present on lamina propria CD4 T cells in the small intestine.

EXAMPLE 5

Optimal T Cell Epitope Length

Previous data testing peptides from 7 to 17 aminoacids in length spanning the core of the dominant T cell epitope in A-gliadin indicated that the 17mer, A-gliadin 57–73 QE65 induced maximal responses in the interferon gamma Elispot using peripheral blood mononuclear cells (PBMC) from coeliac volunteers 6 days after commencing a 3-day gluten challenge.

Peptides representing expansions form the core sequence of the dominant T cell epitope in A-gliadin were assessed in the IFN gamma ELISPOT using peripheral blood mononuclear cells (PBMC) from coeliac volunteers in 6 days after commencing a 3-day gluten challenge (n=4). Peptide 13: A-gliadin 59–71 QE65 (13mer), peptide 15: 58–72 QE65 (15mer), . . . , peptide 27: 52–78 QE65 (27mer).

Figure 11:
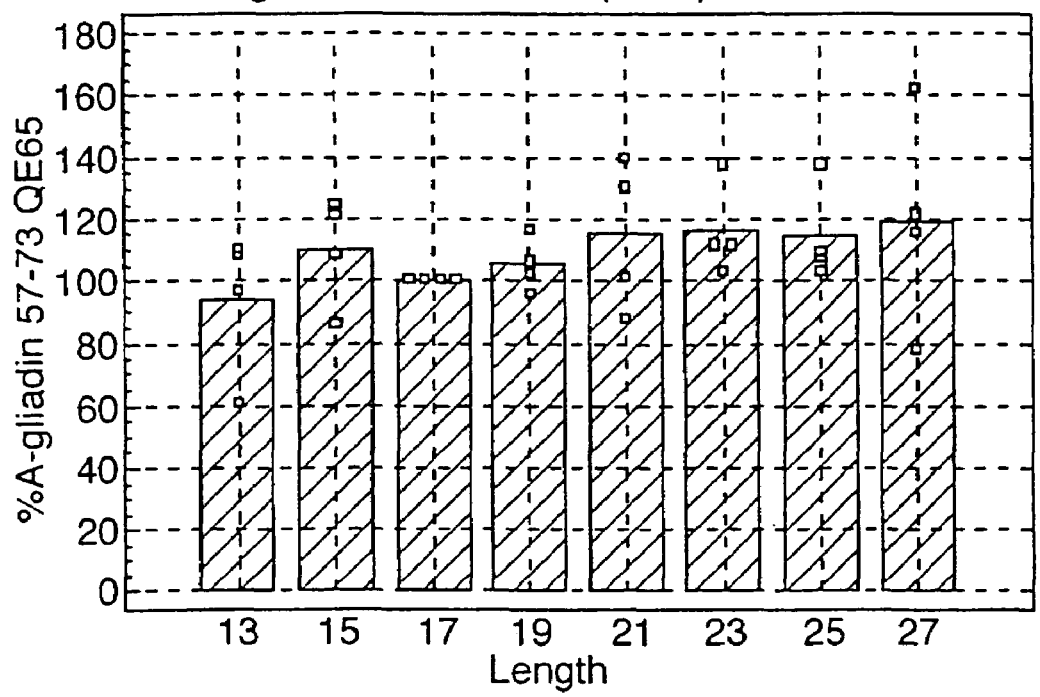
FIG. 11 shows the optimal T cell epitope length.
Figure 12A:
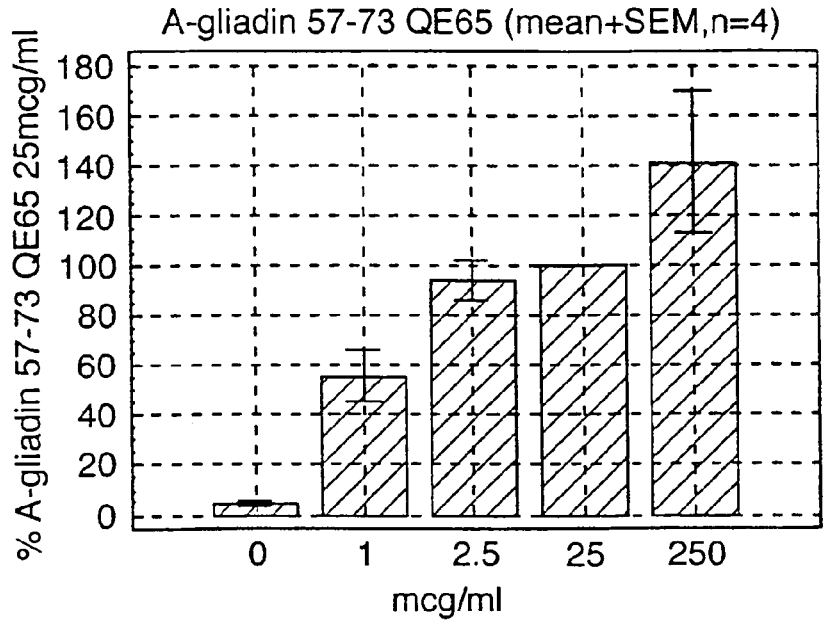
FIG. 12 shows a comparison of A-gliadin 57–73 QE65 with other peptides in a dose response study.
Figure 12B:
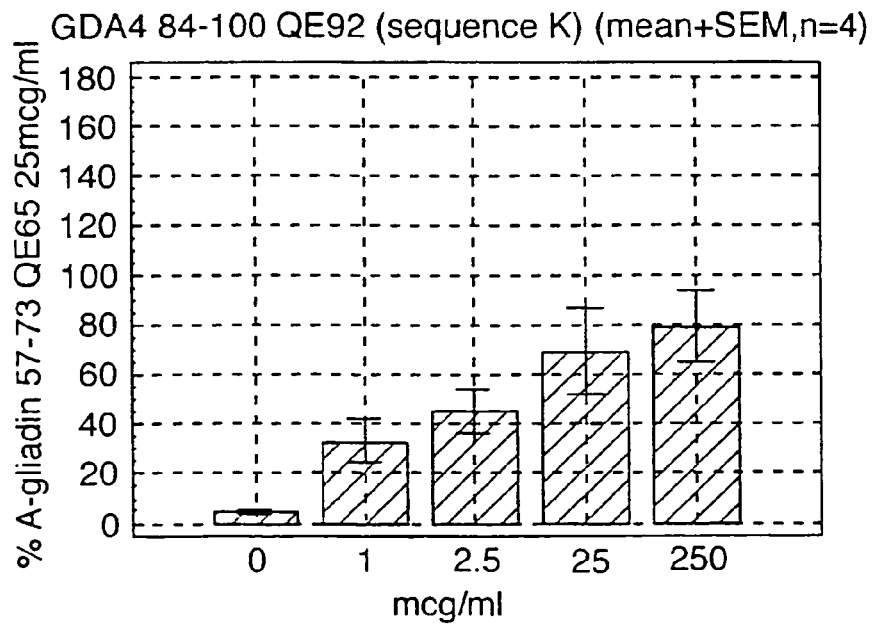
Figure 12C:
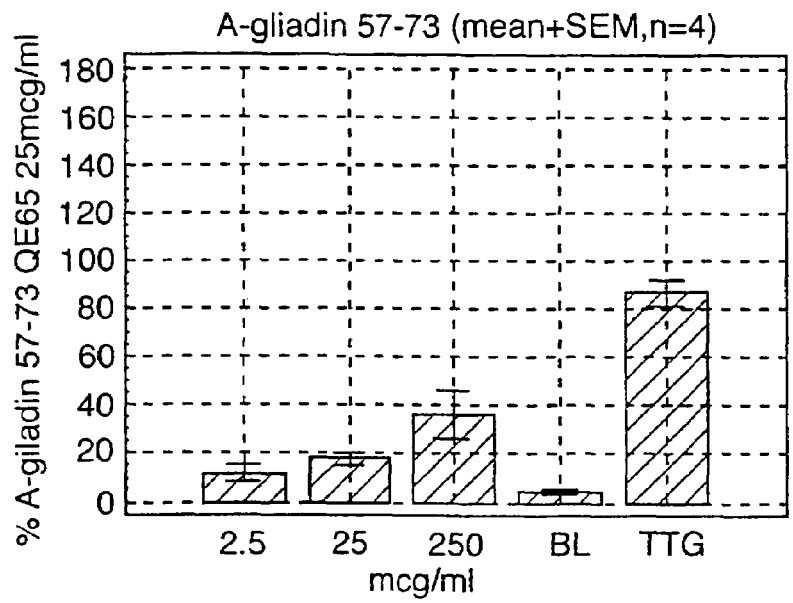
Figure 12D:
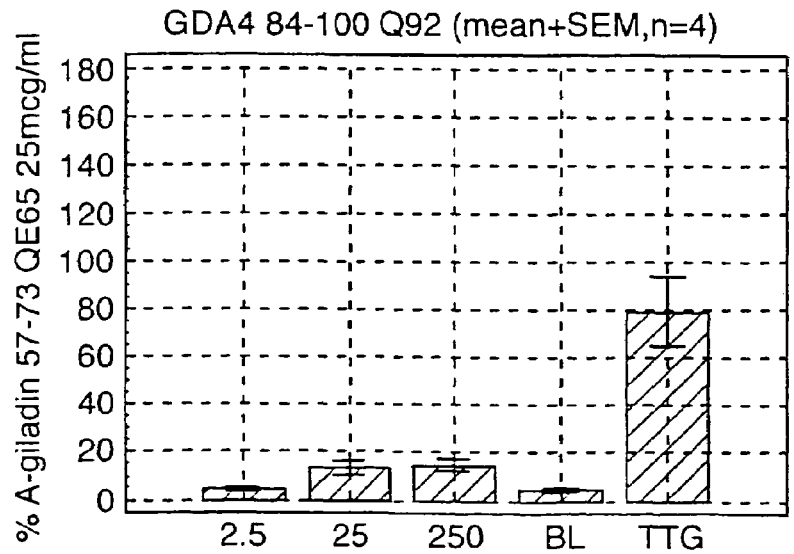
Figure 12E:
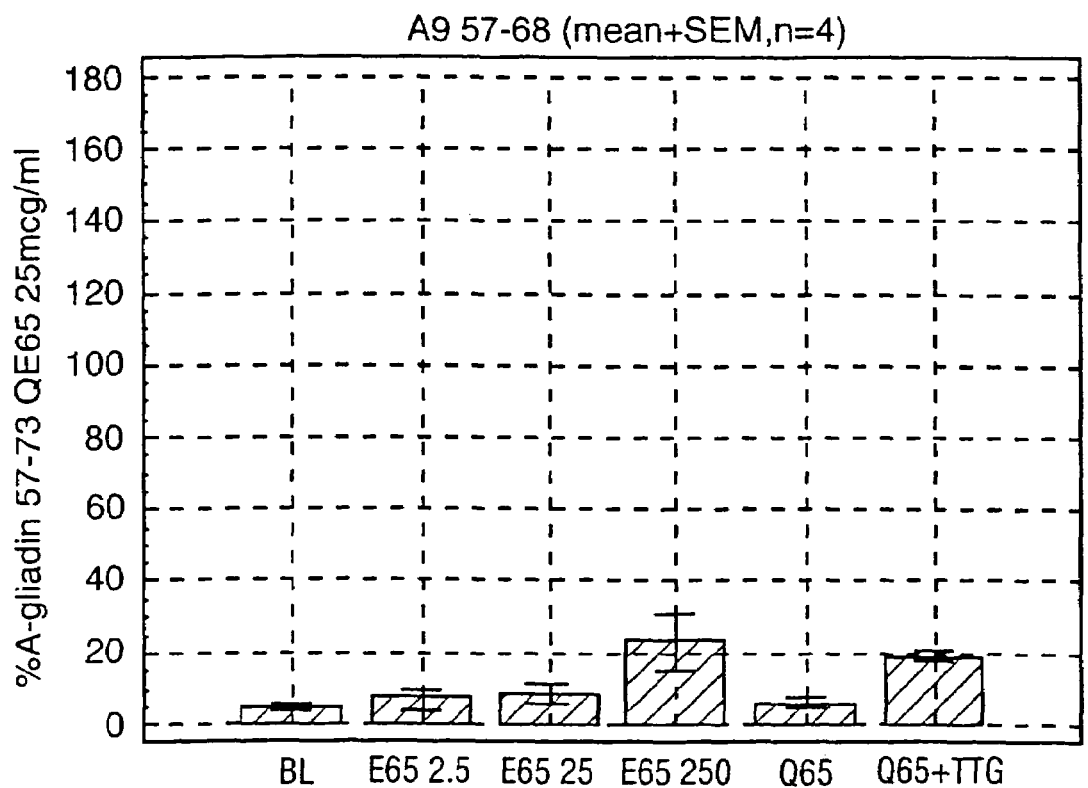
Figure 12F:
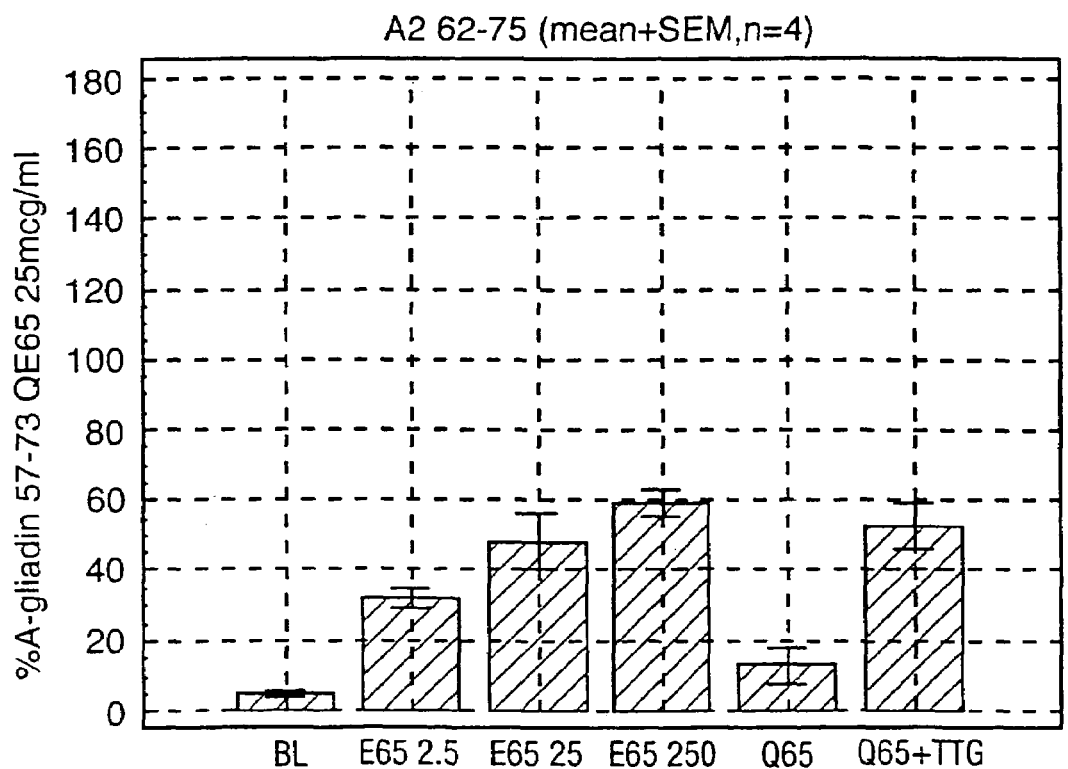
Figure 12G:
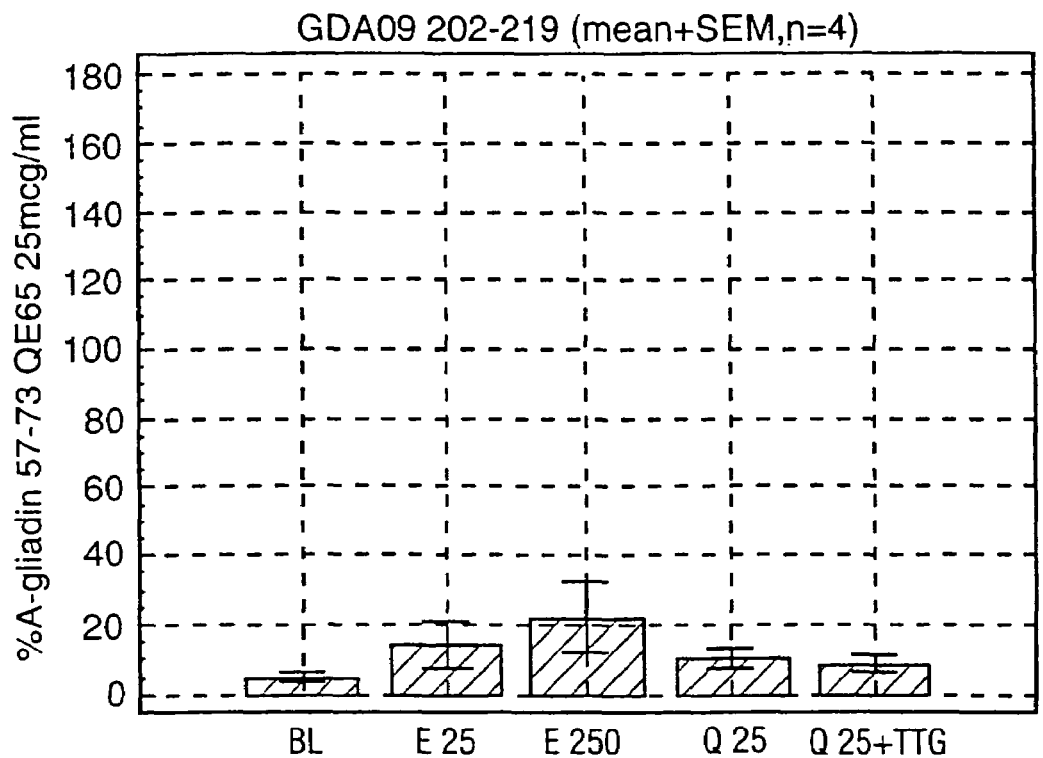
Figure 12H:
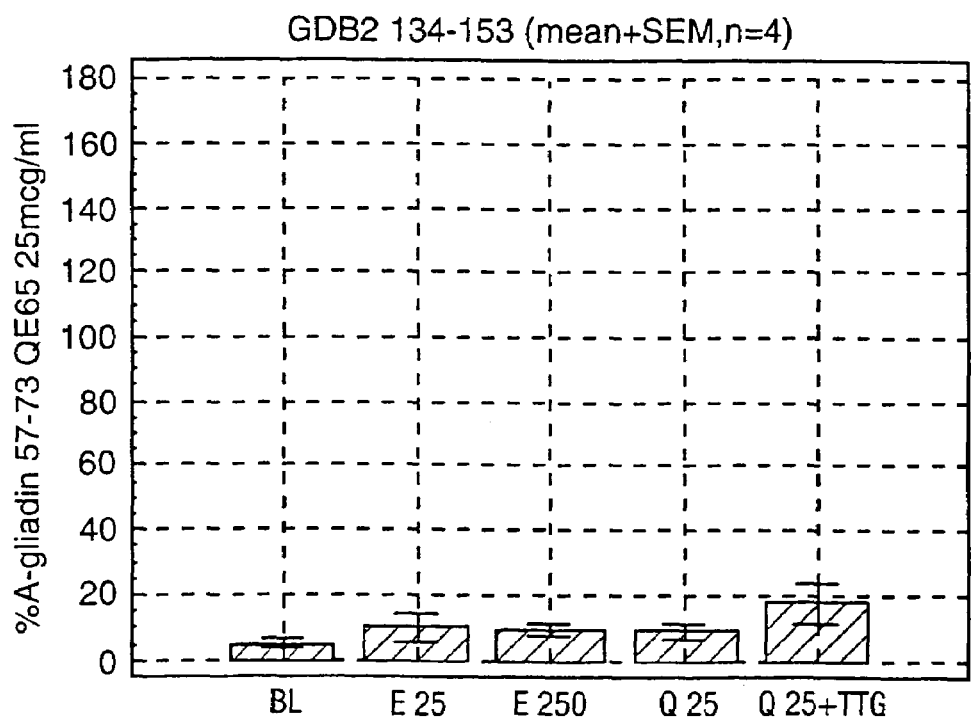

As shown in FIG. 11 expansion of the A-gliadin 57–73 QE65 sequence does not substantially enhance response in the IFNgamma Elispot. Subsequent Examples characterise the agonist and antagonist activity of A-gliadin 57–73 QE65 using 17mer peptides.

EXAMPLE 6

Comparison of A-Gliadin 57–73 QE65 with Other DQ2-Restricted T Cell Epitopes in Coeliac Disease Dose response studies were performed using peptides corresponding to unmodified and transglutaminase-treated peptides corresponding to T cell epitopes of gluten-specific T cell clones and lines from intestinal biopsies of coeliac subjects. Responses to peptides were expressed as percent of response to A-gliadin 57–73 QE65. All subjects were HLA-DQ2+(none were DQ8+).

The studies indicate that A-gliadin 57–73 QE65 is the most potent gliadin peptide for induction of interferon gamma in the ELISpot assay using coeliac PBMC after gluten challenge (see FIGS. 12a–h, and Tables 5 and 6). The second and third epitopes are suboptimal fragments of larger peptides i.e. A-gliadin 57–73 QE65 and GDA4_WHEAT P04724-84–100 QE92. The epitope is only modestly bioactive (approximately $\frac{1}{20}^{th}$ as active as A-gliadin 57–73 QE65 after blank is substracted).

A-gliadin 57–73 QE65 is more potent than other known T cell epitopes in coeliac disease. There are 16 polymorphisms of A-gliadin 57–73 (including the sequence PQLPY) amongst sequenced gliadin genes, their bioactivity is assessed next.

EXAMPLE 7

Comparison of Gliadin- and A-gliadin 57–73 QE65-Specific Responses in Peripheral Blood The relative contribution of the dominant epitope, A-gliadin 57–73 QE65, to the total T cell response to gliadin in coeliac disease is a critical issue. Pepsin-trypsin and chymotrypsin-digested gliadin have been traditionally used as antigen for development of T cell lines and clones in coeliac disease. However, it is possible that these proteases may cleave through certain peptide epitopes. Indeed, chymotrypsin digestion of recombinant α9-gliadin generates the peptide QLQPFPQPELPY, that is a truncation of the optimal epitope sequence QLQPFPQPELPYPQPQS (see above). Transglutaminase-treatment substantially increases the potency of chymotrypsin-digested gliadin in poliferation assays of gliadin-specific T cell clones and lines. Hence, transglutaminase-treated chymotrypsin-digested gliadin (tTG gliadin) may not be an ideal antigen, but responses against this mixture may approximate the "total" number of peripheral blood lymphocyte specific for gliadin. Comparison of responses against A-gliadin 57–73 QE65 and tTG gliadin in the ELISpot assay gives an indication of the contribution of this dominant epitope to the overall immune response to gliadin in coeliac disease, and also be a measure of epitope spreading.

Figure 13A:
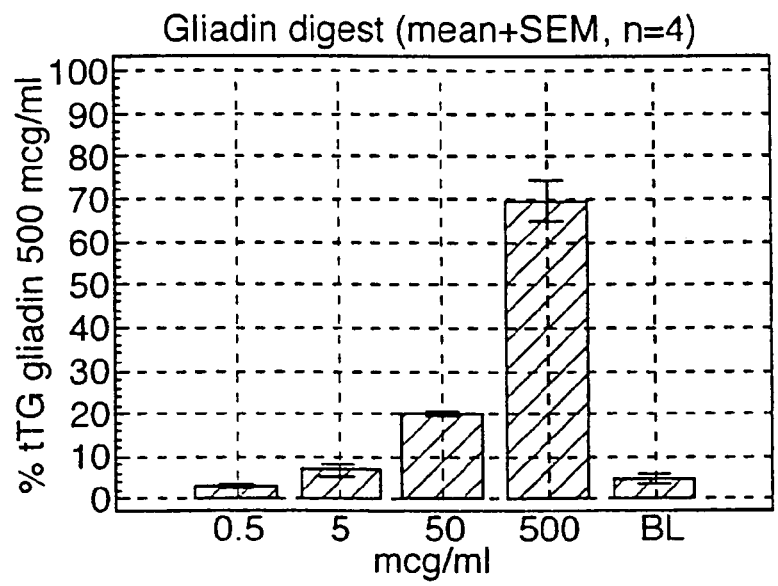
FIG. 13 shows a comparison of gliadin and A-gliadin 57–73 QE65 specific responses.
Figure 13B:
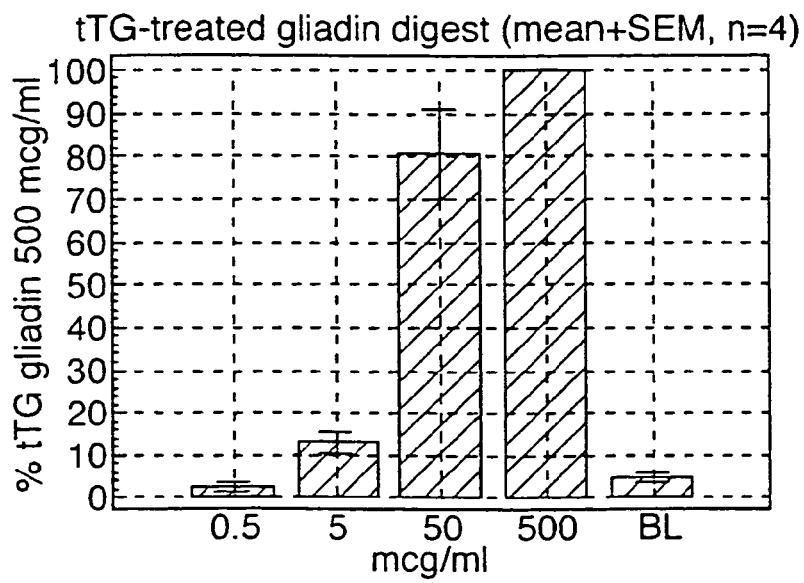
Figure 13C:
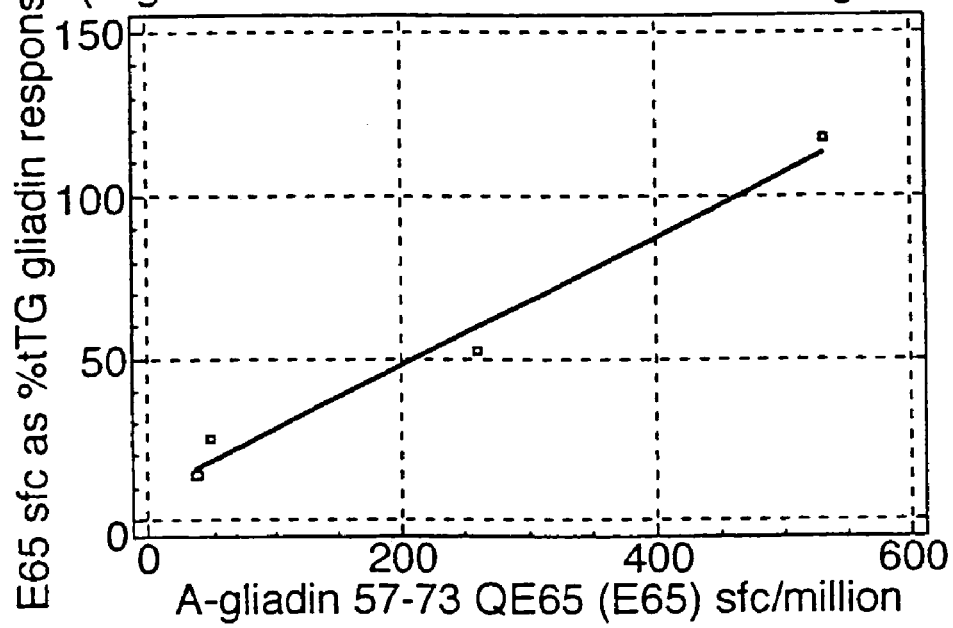

PBMC collected on day 6 or 7 after commencing gluten challenge in 4 coeliac subjects were assessed in dose response studies using chymotrypsin-digested gliadin +/−tTG treatment and compared with ELISpot responses to an optimal concentration of A-gliadin 57–73 QE65 (25 mcg/ml). TTG treatment of gliadin enhanced PBMC responses in the ELISpot approximately 10-fold (tTG was comparable to blank when assessed alone) (see FIGS. 13a–c). In the four coeliac subjects studied, A-gliadin 57–73 QE65 (25 mcg/ml) elicited responses between 14 and 115% those of tTG gliadin (500 mcg/ml), and the greater the response to A-gliadin 57–73 QE65 the greater proportion it represented of the tTG gliadin response.

Relatively limited data suggest that A-gliadin 57–73 QE65 responses are comparable to tTG gliadin in some subjects. Epitope spreading associated with more evolved anti-gliadin T cell responses may account for the smaller contribution of A-gliadin 57–73 QE65 to "total" gliadin responses in peripheral blood in some individuals. Epitope spreading may be maintained in individuals with less strictly gluten free diets.

EXAMPLE 8

Definition of Gliadin Peptides Bioactive in Coeliac Disease: Polymorphisms of A-Gliadin 57–73

Overlapping 15mer peptides spanning the complete sequence of A-gliadin were assessed in order to identify the immunodominant sequence in coeliac disease. A-gliadin was the first fully sequenced alpha gliadin protein and gene, but is one of approximately 30–50 related alpha gliadin proteins in wheat. Twenty five distinct alpha-gliadin genes have been identified by searching protein data bases, Swiss-Prot and TREMBL describing a further 8 alpha-gliadins. Contained within these 25 alpha-gliadins, there are 16 distinct polymorphisms of the sequence corresponding to A-gliadin 57–73 (see Table 7).

Figure 14B:
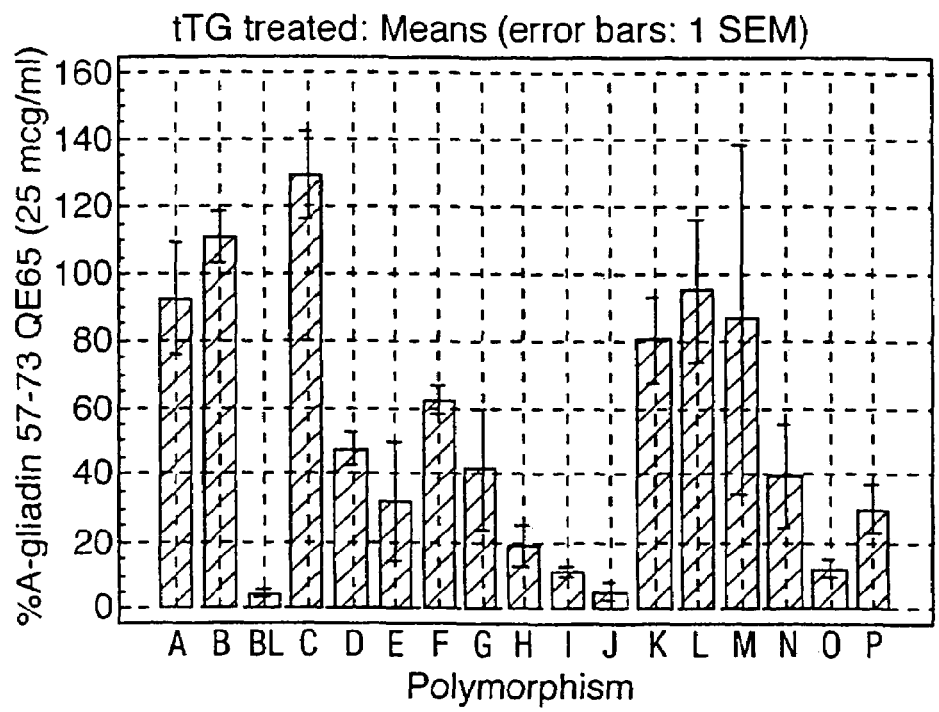
FIG. 14 shows the bioactivity of gliadin polymorphisms in coeliac subjects.
Figure 14D:
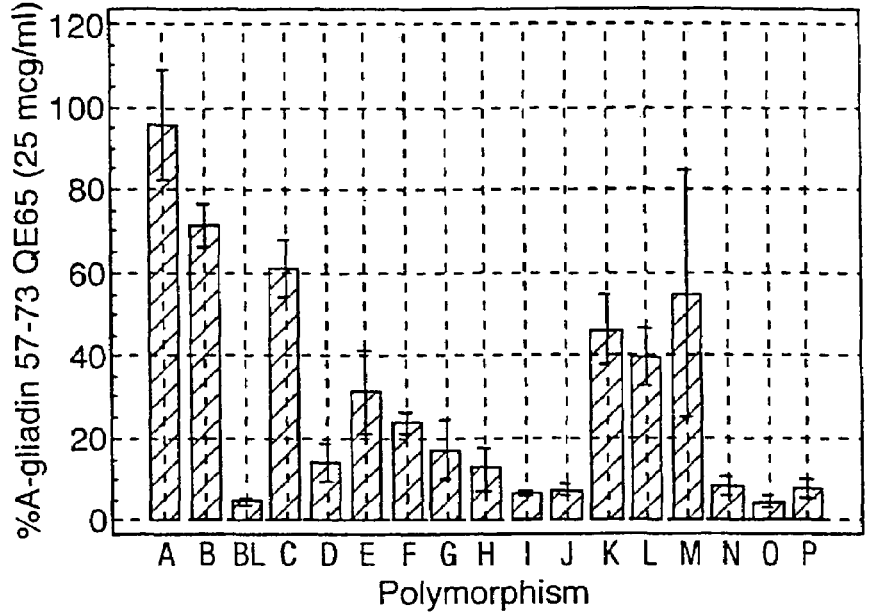
Figure 14E:
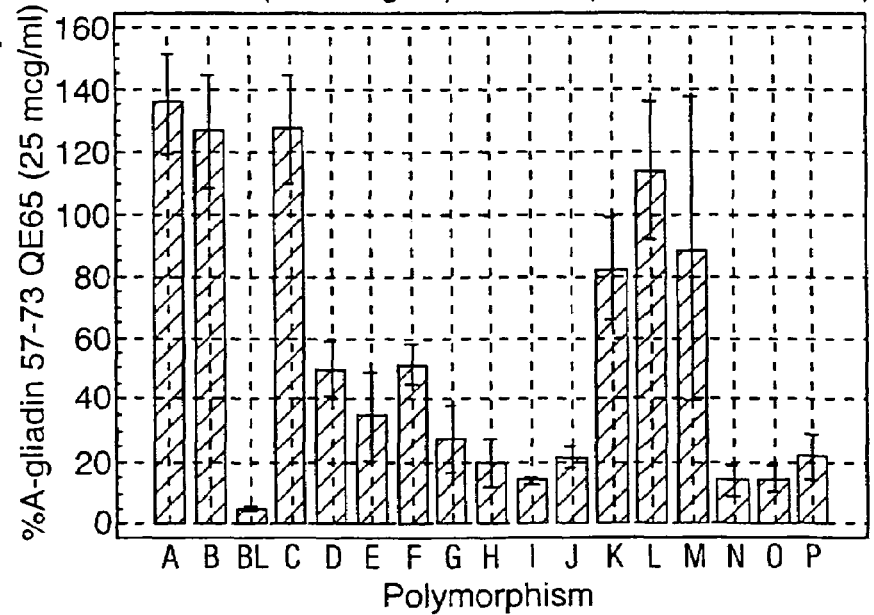

Synthetic peptides corresponding to these 16 polymorphisms, in an unmodified form, after treatment with transglutaminase in vitro, as well as with glutamate substituted at position 10 (equivalent to QE65 in A-gliadin 57–73) were assessed using PBMC from coeliac subjects, normally following a gluten free diet, day 6 or 7 after gluten challenge in interferon gamma ELISpot assays. Glutamate-substituted peptides were compared at three concentrations (2.5, 25 and 250 mcg/ml), unmodified peptide and transglutaminase-treated peptides were assessed at 25 mcg/ml only. Bioactivity was expressed as % of response associated with A-gliadin 57–73 QE65 25 mcg/m in individual subjects (n=4). (See FIG. 14).

Bioactivity of "wild-type" peptides was substantially increased (>5-fold) by treatment with transglutaminase. Transglutaminase treatment of wild-type peptides resulted in bioactivity similar to that of the same peptides substituted with glutamate at position 10. Bioactivities of five glutamate-substituted peptides (B, C, K, L, M), were >70% that of A-gliadin 57–73 QE65 (A), but none was significantly more bioactive than A-gliadin 57–73 QE65. PBMC responses to glutamate-substituted peptides at concentrations of 2.5 and 250 mcg/ml were comparable to those at 25 mcg/ml. Six glutamate-substituted gliadin peptides (H, I, J, N, O, P) were <15% as bioactive as A-gliadin 57–73 QE65. Other peptides were intermediate in bioactivity.

At least six gliadin-derived peptides are equivalent in potency to A-gliadin 57–73 QE65 after modfication by transglutaminase. Relatively non-bioactive polymorphisms of A-gliadin 57–73 also exist. These data indicate that transglutaminase modification of peptides from several gliadins of Tricetum aestivum, T. uartu and T. spelta may be capable of generating the immunodominant T cell epitope in coeliac disease.

Genetic modification of wheat to generate non-coeliac-toxic wheat is likely require removal or modification of multiple gliadin genes. Generation of wheat containing gliadins or other proteins or peptides incorporating sequences defining altered peptide ligand antagonists of A-gliadin 57–73 is an alternative strategy to generate genetically modified wheat that is therapeutic rather than "non-toxic" in coeliac disease.

EXAMPLE 9

Definition of Core Epitope Sequence:

Comparison of peptides corresponding to truncations of A-gliadin 56–75 from the N- and C-terminal indicated that the core sequence of the T cell epitope is PELPY (A-gliadin 64–68). Attempts to define non-agonists and antagonists will focus on variants of A-gliadin that are substituted at residues that substantially contribute to its bioactivity.

Figure 15:
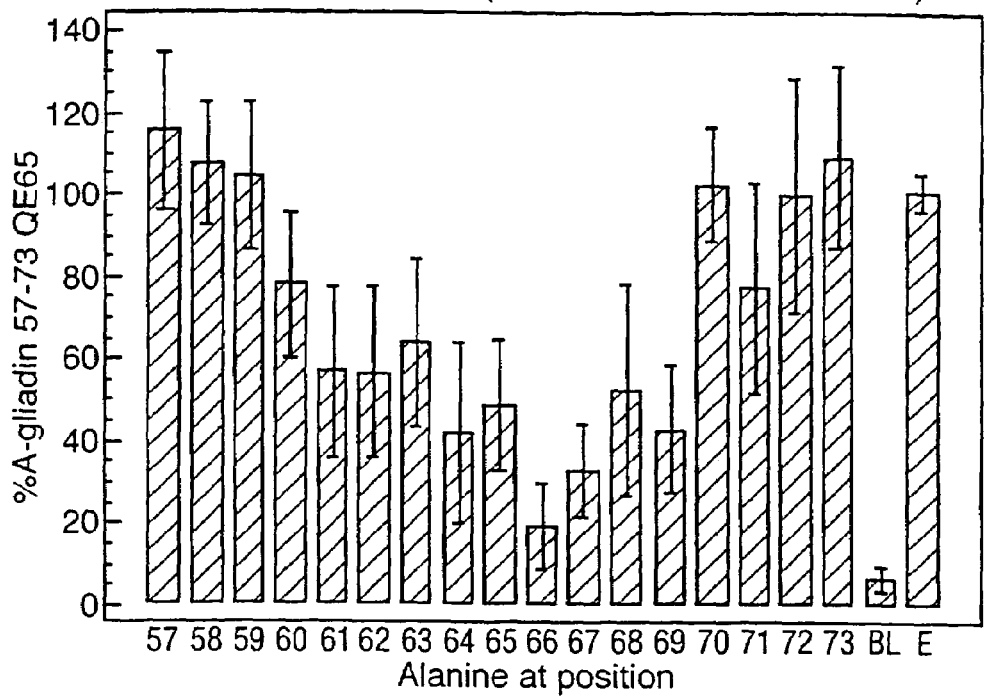
FIGS. 15 and 16 show the defining of the core epitope sequence.
Figure 16:
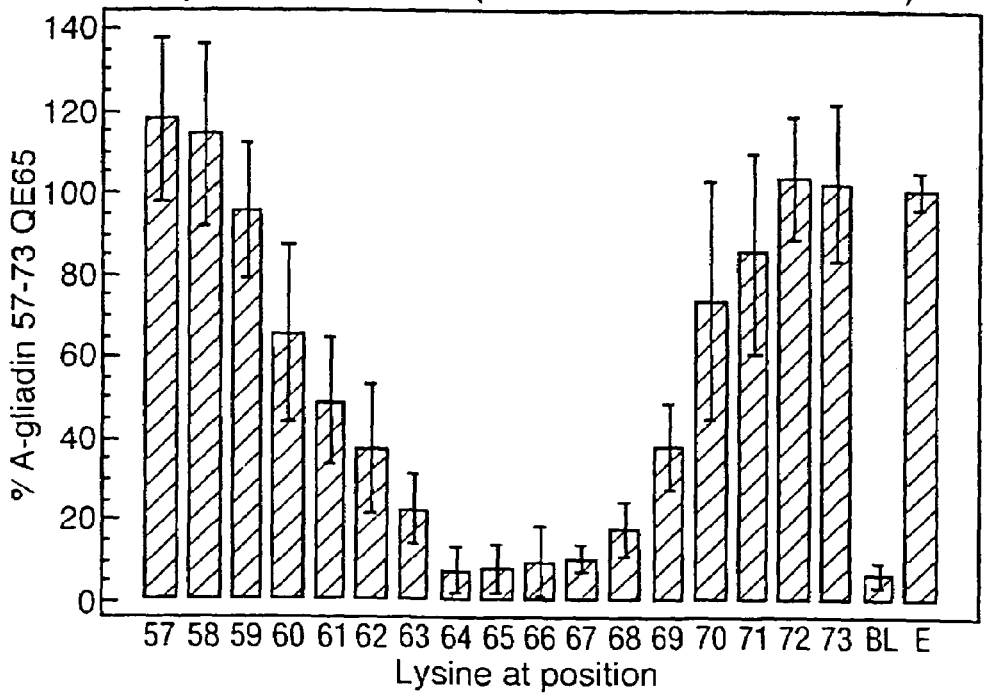
Figure 18:
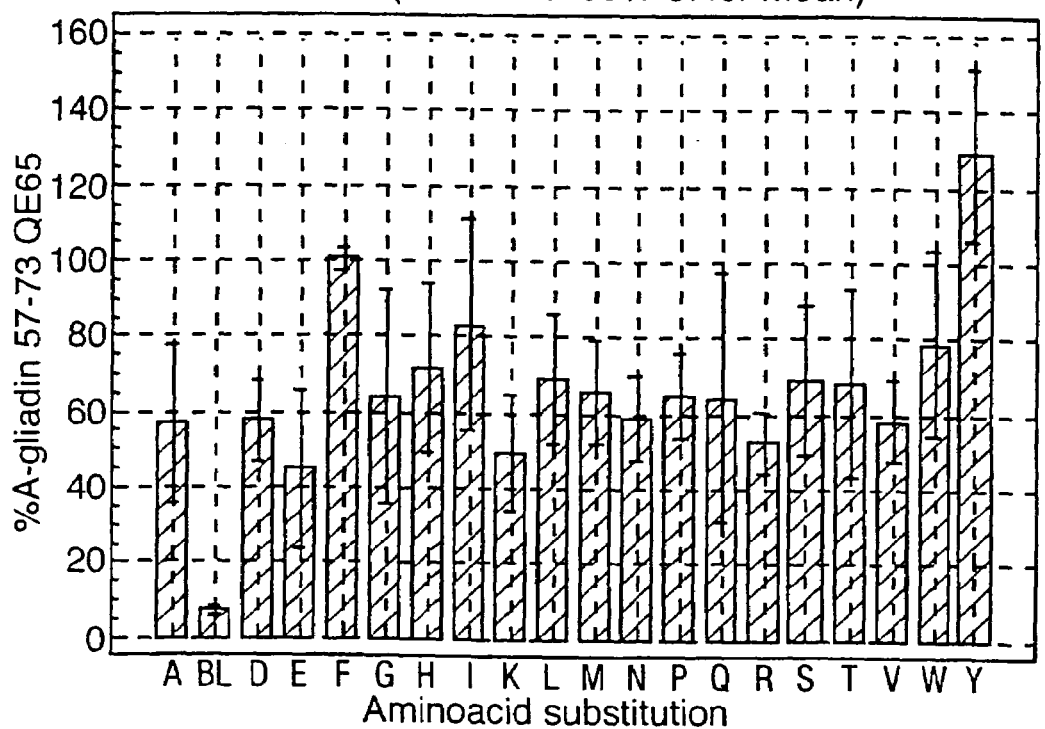
Figure 19:
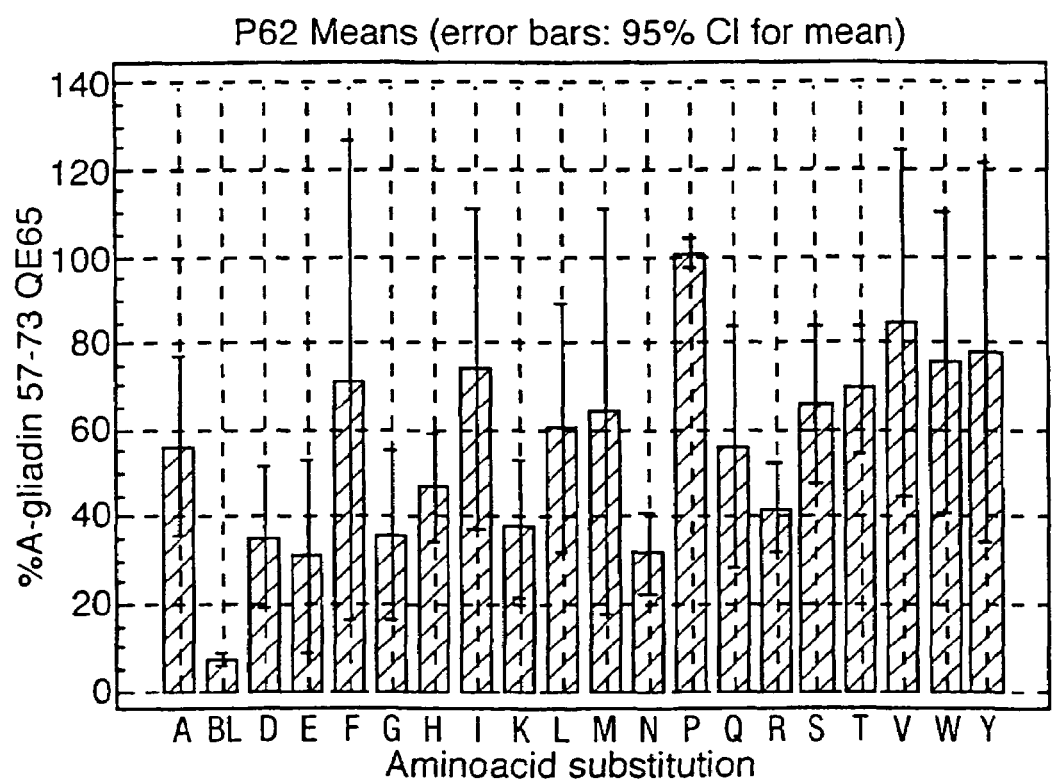
Figure 20:
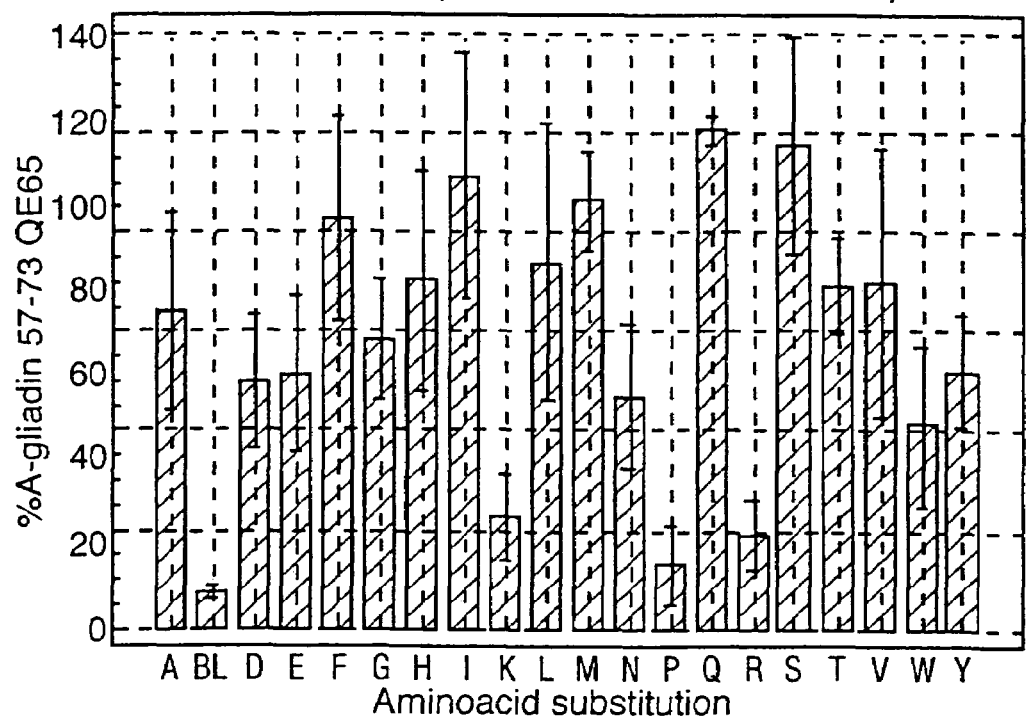
Figure 21:
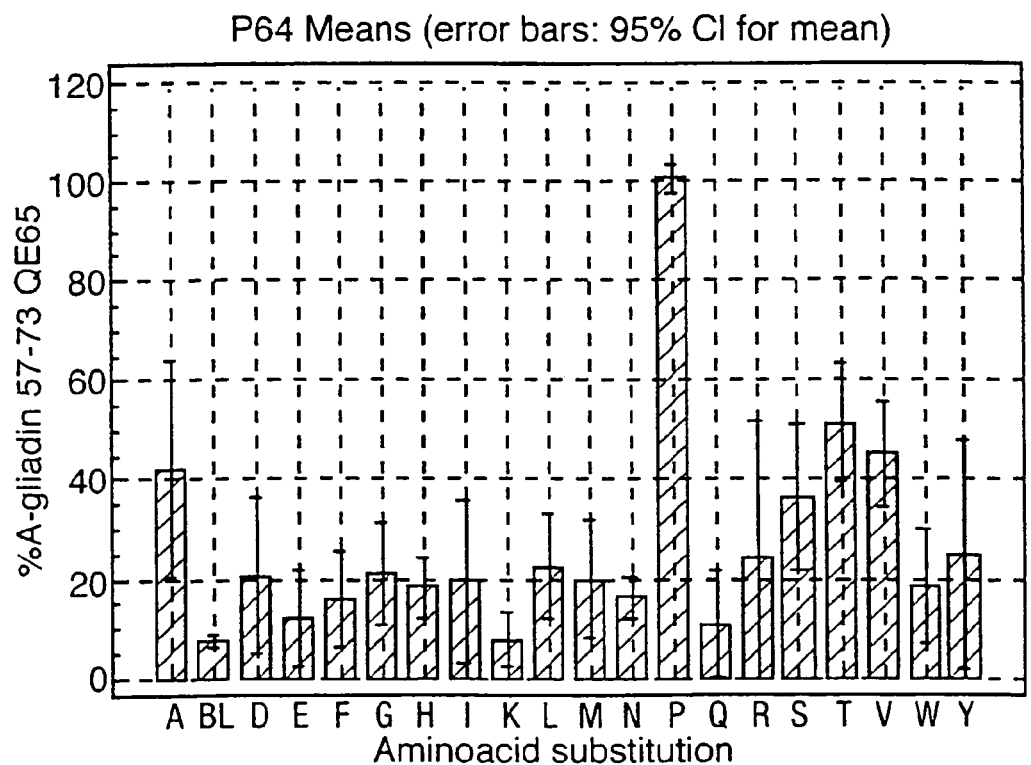
Figure 24:
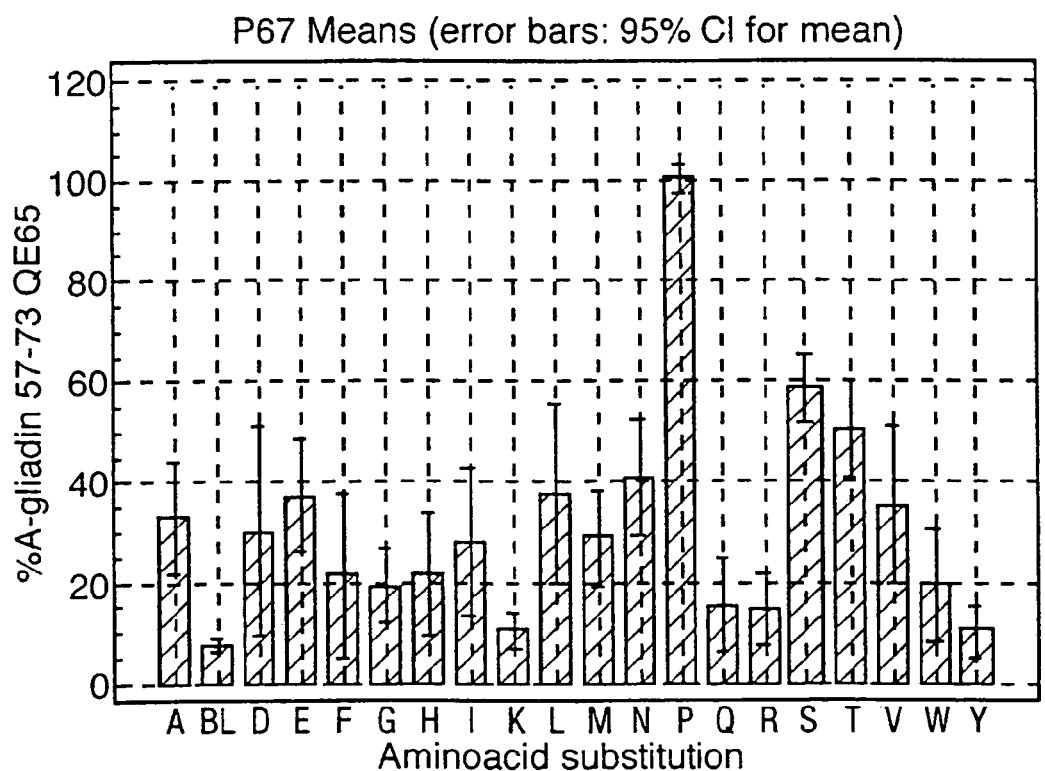
Figure 25:
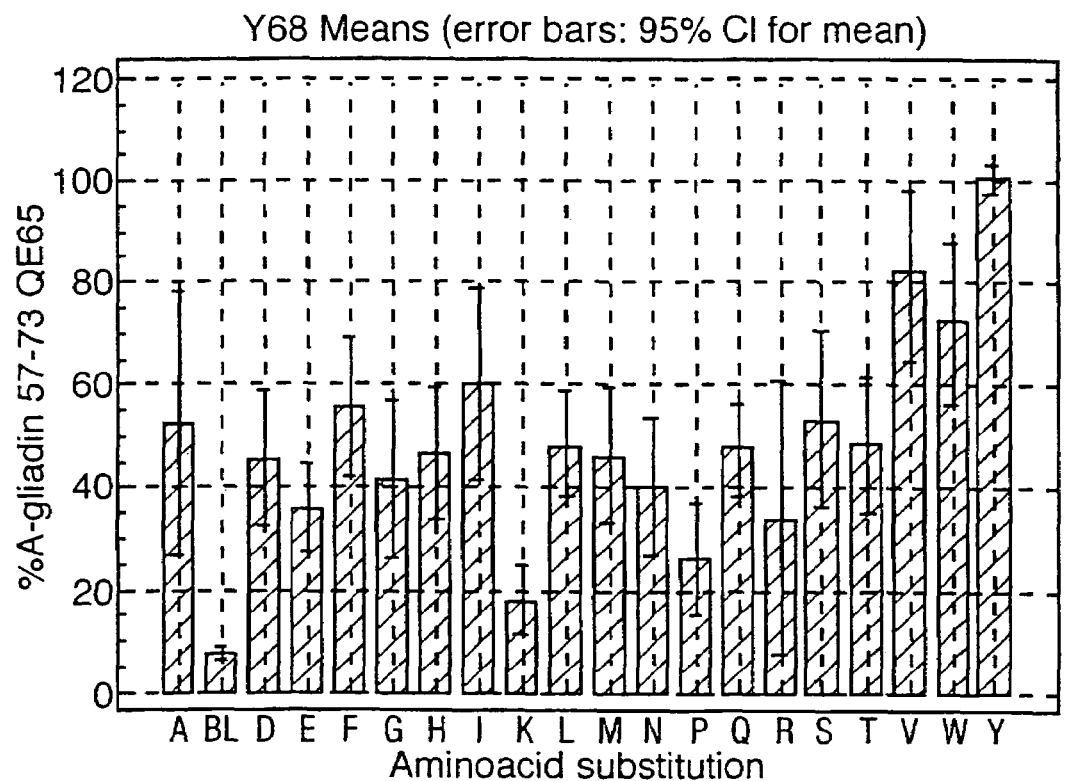
Figure 26:
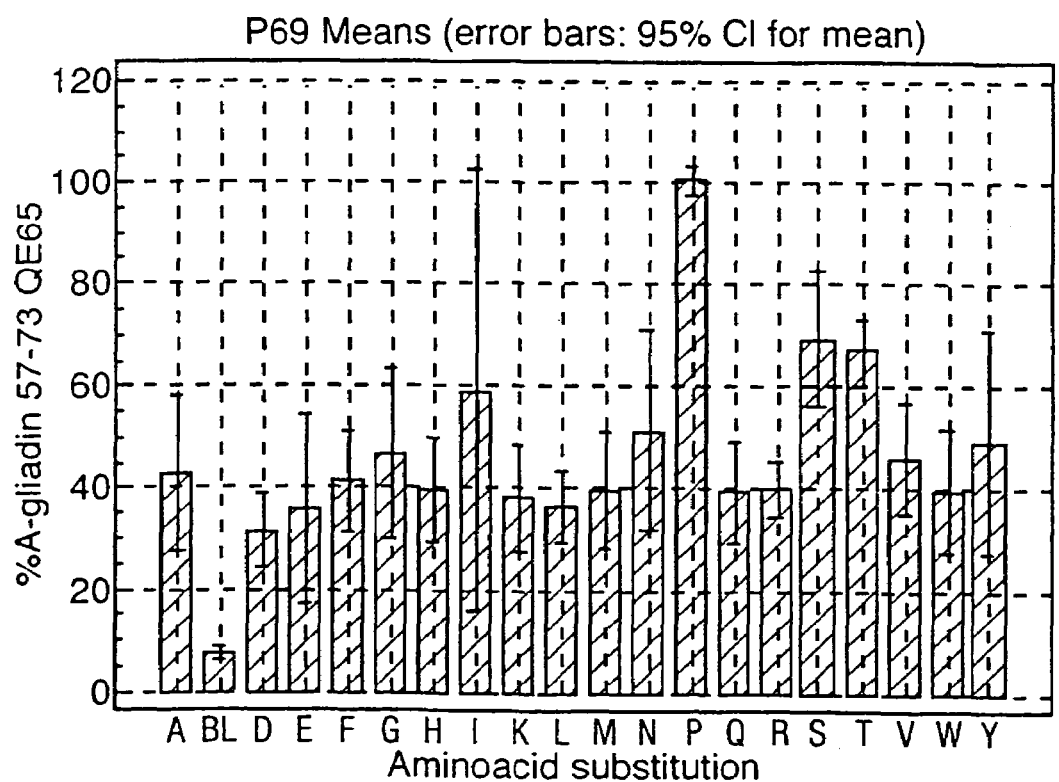
Figure 28B:
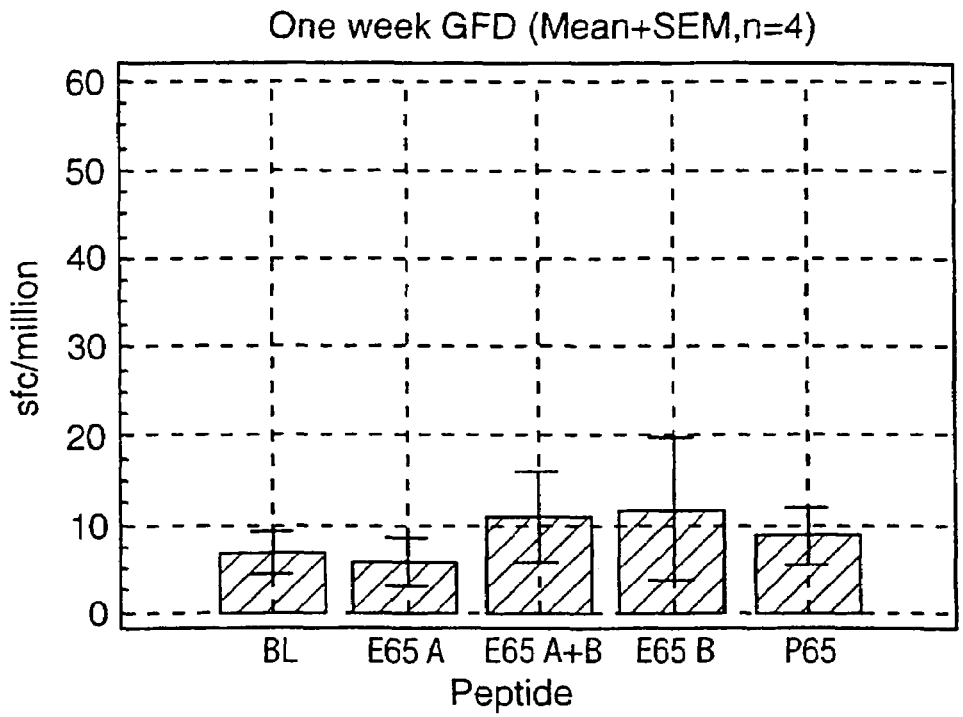
FIG. 28 shows responses in different patient groups.
Figure 28C:
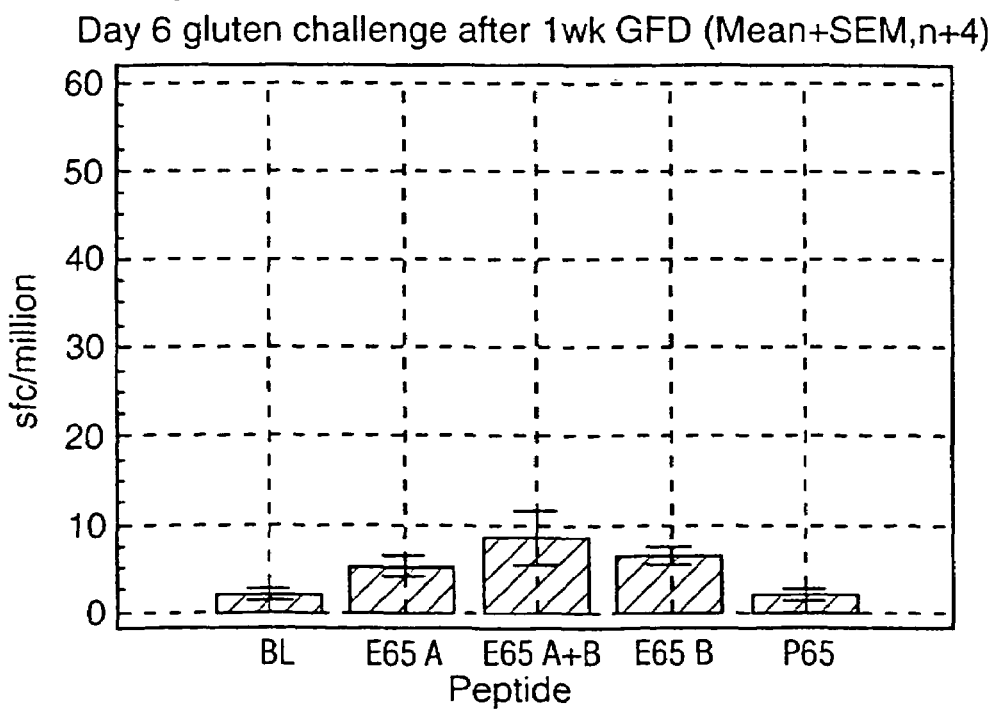
Figure 28D:
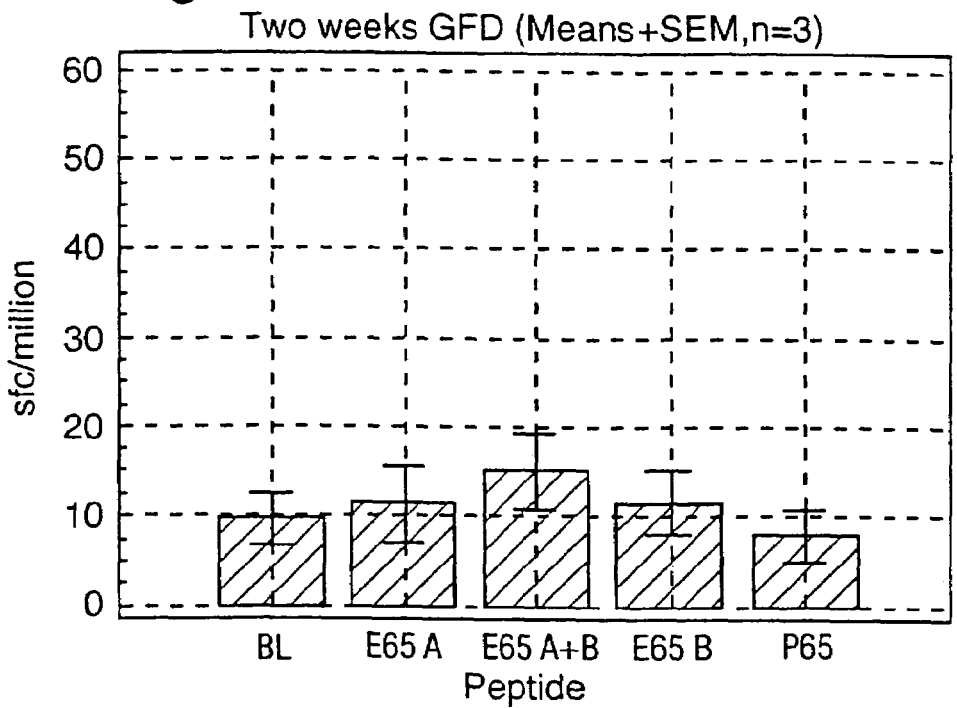
Figure 28E:
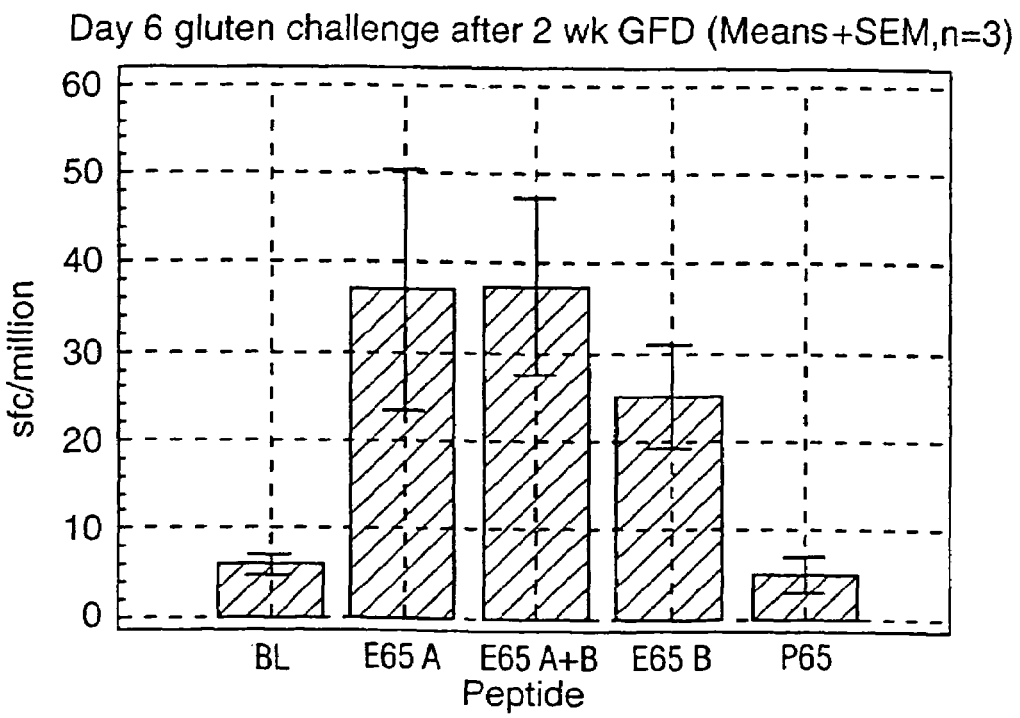
Figure 28F:
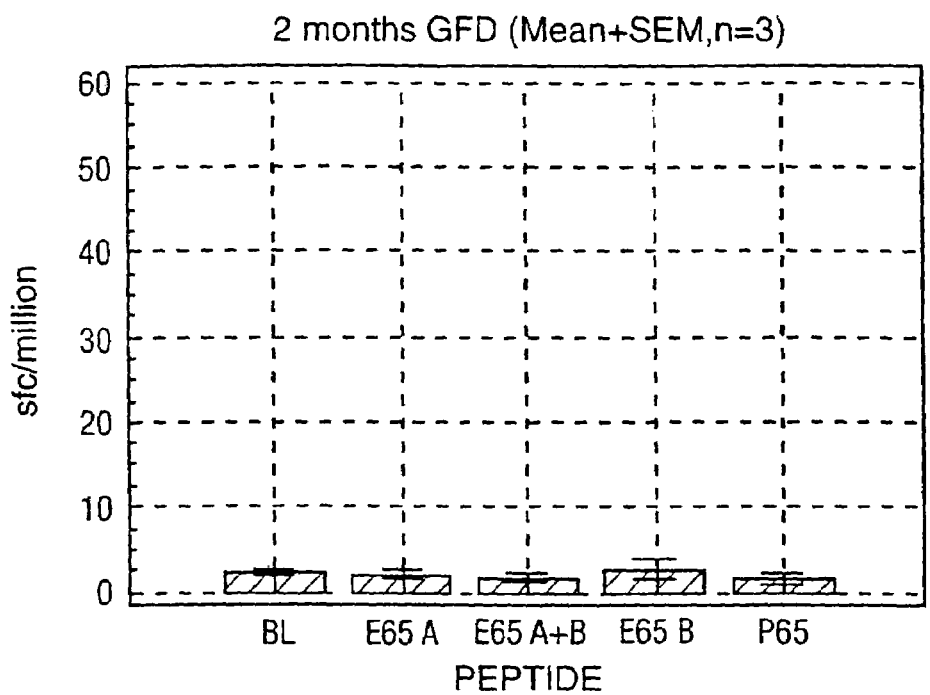
Figure 28G:
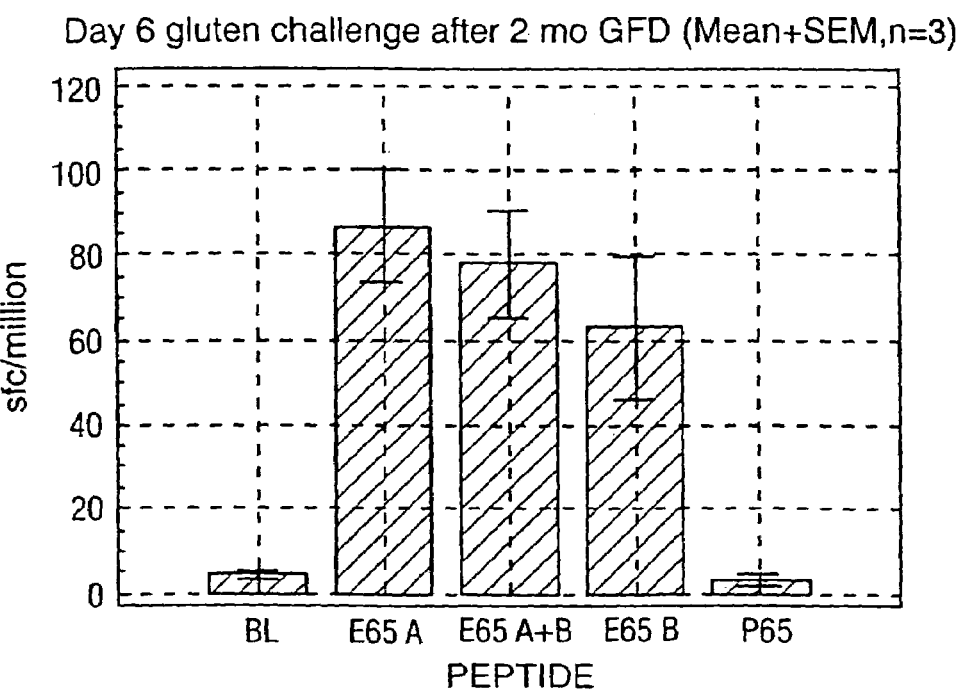

Peptides corresponding to A-gliadin 57–73 QE65 with alanine (FIG. 15) or lysine (FIG. 16) substituted for residues 57 to 73 were compared in the IFN gamma ELISPOT usng peripheral blood mononuclear cells (PBMC) from coeliac volunteers 6 days after commencing a 3-day gluten challenge (n=8). [BL is blank, E is A-gliadin 57–73 QE65: QLQPFPQPELPYPQPQS].

It was found that residues corresponding to A-gliadin 60–70 QE65 (PFPQPELPYPQ) contribute substantially to the bioactivity in A-gliadin 57–73 QE65. Variants of A-gliadin 57–73 QE65 substituted at positions 60–70 are assessed in a 2-step procedure. Initially, A-gliadin 57–73 QE65 substituted at positions 60–70 using 10 different aminoacids with contrasting properties are assessed. A second group of A-gliadin 57–73 QE65 variants (substituted with all other naturally occurring aminoacids except cysteine at positions that prove are sensitive to modification) are assessed in a second round.

EXAMPLE 10

Agonist Activity of Substituted Variants of A-Gliadin 57–73 QE65

A-gliadin 60–70 QE65 is the core sequence of the dominant T cell epitope in A-gliadin. Antagonist and non-agonist peptide variants of this epitope are most likely generated by modification of this core sequence. Initially, A-gliadin 57–73 QE65 substituted at positions 60–70 using 10 different aminoacids with contrasting properties will be assessed in the IFNgamma ELISPOT using PBMC from coeliac subjects 6 days after starting 3 day gluten challenge. A second group of A-gliadin 57–73 QE65 variants (substituted with all other naturally occurring aminoacids except cysteine) at positions 61–70 were also assessed. Both groups of peptides (all at 50 mcg/ml, in duplicate) were assessed using PBMC from 8 subjects and compared to the unmodified peptide (20 replicates per assay). Previous studies indicate that the optimal concentration for A-gliadin 57–73 QE65 in this assay is between 10 and 100 mcg/ml.

Results are expressed as mean response in spot forming cells (95% confidence interval) as % A-G 57–73 QE65 mean response in each individual. Unpaired t-tests will be used to compare ELISPOT responses of modified peptides with A-G 57–73 QE65. Super-agonists were defined as having a greater response than A-G 57–73 QE65 at a level of significance of $p<0.01$; partial agonists as having a response less than A-G 57–73 QE65 at a level of significance of $p<0.01$, and non-agonists as being not significantly different ($p>0.01$) from blank (buffer without peptide). Peptides with agonist activity 30% or less that of A-gliadin 57–73 QE65 were considered "suitable" partial or non-agonists to assess for antagonistic activity (see Table 8 and FIGS. 17–27).

The IFNgamma ELISPOT response of PBMC to A-gliadin 57–73 QE65 is highly specific at a molecular level. Proline at position 64 (P64), glutamate at 65 (E65) and leucine at position 66 (L66), and to a lesser extent Q63, P67, Y68 and P69 are particularly sensitive to modification. The substitutions Y61 and Y70 both generate super-agonists with 30% greater bioactivity than the parent peptide, probably by enhancing binding to HLA-DQ2 since the motif for this HLA molecule indicates a preference for bulky hydrophobic resides at positions 1 and 9. Eighteen non-agonist peptides were identified. Bioactivities of the variants (50 mcg/ml): P65, K64, K65 and Y65 (bioactivity 7–8%) were comparable to blank (7%). In total, 57 mutated variants of A-gliadin 57–73 QE65 were 30% or less bioactive than A-gliadin 57–73 QE65.

The molecular specificity of the peripheral blood lymphocyte (PBL) T cell response to the dominant epitope, A-gliadin 57–73 QE65, is consistently reproducible amongst HLA-DQ2+ coeliac subjects, and is highly specific to a restricted number of aminoacids in the core 7 aminoacids. Certain single-aminoacid variants of A-gliadin 57–73 QE65 are consistently non-agonists in all HLA-DQ2+ coeliac subjects.

EXAMPLE 11

Antagonist Activity of Substituted Variants

The homogeneity of the PBL T cell response to A-gliadin 57–73 QE65 in HLA-DQ2+ coeliac disease suggests that altered peptide ligands (APL) capable of antagonism in PBMC ex vivo may exist, even though the PBL T cell response is likely to be poly- or oligo-clonal. APL antagonists are generally weak agonists. Fifty-seven single aminoacid-substituted variants of A-gliadin 57–73 QE65 with agonist activity 30% or less have been identified and are suitable candidates as APL antagonists. In addition, certain weakly bioactive naturally occurring polymorphisms of A-gliadin 57–73 QE65 have also been identified (see below) and may be "naturally occurring" APL antagonists. It has also been suggested that competition for binding MHC may also antagonise antigen-specific T cell immune. Hence, non-gliadin peptides that do not induce IFNgamma responses in coeliac PBMC after gluten challenge but are known to bind to HLA-DQ2 may be capable of reducing T cell responses elicited by A-gliadin 57–73 QE65. Two peptides that bind avidly to HLA-DQ2 are HLA class 1α46–60 (HLA 1 a) (PRAPWIEQEGPEYW) and thyroid peroxidase (tp) 632–645Y (IDVWLGGLLAENFLPY).

Simultaneous addition of peptide (50 µg/ml) or buffer and A-gliadin 57–73 QE65 (10 µg/ml) in IFNgamma ELISPOT using PBMC from coeliac volunteers 6 days after commencing 3 day gluten challenge (n=5). Results were expressed as response with peptide plus A-G 57–73 QE65 (mean of duplicates) as % response with buffer plus A-G 57–73 QE65 (mean of 20 replicates). (See Table 9).

Four single aminoacid-substituted variants of A-gliadin 57–73 QE65 reduce the interferon gamma PBMC ELISPOT response to A-gliadin 57–73 QE65 ($p<0.01$) by between 25% and 28%, 13 other peptide variants reduce the ELISPOT response by between 18% and 24% ($p<0.06$). The HLA-DQ2 binder, thyroid peroxidase (tp) 632–645Y reduces PBMC interferon gamma responses to A-gliadin 57–73 QE65 by 31% ($p<0.0001$) but the other HLA-DQ2 binder, HLA class 1 a 46–60, does not alter responses (see Table 9). The peptide corresponding to a transglutaminase-modified polymorphism of A-glaidin 57–73, SwissProt accession no.: P04725 82–98 QE90 (PQPQPFP- PELPYPQPQS) reduces responses to A-gliadin 57–73 QE65 by 19% (p<0.009) (see Table 11).

Interferon gamma responses of PBMC to A-gliadin 57–73 QE65 in ELISPOT assays are reduced by co-administration of certain single-aminoacid A-gliadin 57–73 QE65 variants, a polymorphism of A-gliadin 57–73 QE65, and an unrelated peptide known to bind HLA-DQ2 in five-fold excess. These finding suggest that altered peptide ligand antagonists of A-gliadin 57–73 QE65 exist. Not only putative APL antagonists but also certain peptides that bind HLA-DQ2 effectively reduce PBL T cell responses to A-gliadin 57–73 QE65.

These findings support two strategies to interrupt the T cell response to the dominant A-gliadin epitope in HLA-DQ2+ coeliac disease.
1. Optimisation of APL antagonists by substituting aminoacids at more than one position (64–67) for use as "traditional" peptide pharmaceuticals or for specific genetic modification of gliadin genes in wheat.
2. Use of high affinity HLA-DQ2 binding peptides to competitively inhibit presentation of A-gliadin 57–73 QE65 in association with HLA-DQ2.
   These two approaches may be mutually compatible. Super-agonists were generated by replacing F61 and Q70 with tyrosine residues. It is likely these super-agonists resulted from improved binding to HLA-DQ2 rather than enhanced contact with the T cell receptor. By combining these modifications with other substitutions that generate modestly effective APL antagonists might substantially enhance the inhibitory effect of substituted A-gliadin 57–73 QE65 variants.

EXAMPLE 12

Development of Interferon Gamma ELISpot Using PBMC and A-Gliadin 57–73 QE65 and P04724 84–100 QE92 as a Diagnostic for Coeliac Disease: Definition of Immune-Responsiveness in Newly Diagnosed Coeliac Disease Induction of responsiveness to the dominant A-gliadin T cell epitope in PBMC measured in the interferon gamma ELISpot follows gluten challenge in almost all DQ2+ coeliac subjects following a long term strict gluten free diet (GFD) but not in healthy DQ2+ subjects after 4 weeks following a strict GFD. A-gliadin 57–73 QE65 responses are not measurable in PBMC of coeliac subjects before gluten challenge and pilot data have suggested these responses could not be measured in PBMC of untreated coeliacs. These data suggest that in coeliac disease immune-responsiveness to A-gliadin 57–73 QE65 is restored following antigen exclusion (GFD). If a diagnostic test is to be developed using the ELISpot assay and PBMC, it is desireable to define the duration of GFD required before gluten challenge is capable of inducing responses to A-gliadin 57–73 QE65 and other immunoreactive gliadin peptides in blood.

Newly diagnosed DQ2+ coeliac subjects were recruited from the gastroenterology outpatient service. PBMC were prepared and tested in interferon gamma ELISpot assays before subjects commenced GFD, and at one or two weeks after commencing GFD. In addition, gluten challenge (3 days consuming 4 slices standard white bread, 200 g/day) was performed at one or two weeks after starting GFD. PBMC were prepared and assayed on day six are after commencing gluten challenge. A-gliadin 57–73 QE65 (A), P04724 84–100 QE92 (B) (alone and combined) and A-gliadin 57–73 QP65 (P65) (non-bioactive variant, see above) (all 25 mcg/ml) were assessed.

All but one newly diagnosed coeliac patient was DQ2+ (one was DQ8+) (n=11). PBMC from newly diagnosed coeliacs that were untreated, or after 1 or 2 weeks following GFD did not show responses to A-gliadin 57–73 QE65 and P04724 84–100 QE92 (alone or combined) that were not significantly different from blank or A-gliadin 57–73 QP65 (n=9) (see FIG. 28). Gluten challenge in coeliacs who had followed GFD for only one week did not substantially enhance responses to A-gliadin 57–73 QE65 or P04724 84–100 QE92 (alone or combined). But gluten challenge 2 weeks after commencing GFD did induce responses to A-gliadin 57–73 QE65 and P04724 84–100 QE92 (alone or combined) that were significantly greater than the non-bioactive variant A-gliadin 57–73 QP65 and blank. Although these responses after gluten challenge at 2 weeks were substantial they appear to be less than in subjects >2 months after commencing GFD. Responses to A-gliadin 57–73 QE65 alone were equivalent or greater than responses to P04724 84–100 QE92 alone or when mixed with A-gliadin 57–73 QE65. None of the subjects experienced troubling symptoms with gluten challenge.

Immune responsiveness (as measured in PBMC after gluten challenge) to A-gliadin is partially restored 2 weeks after commencing GFD, implying that "immune unresponsiveness" to this dominant T cell epitope prevails in untreated coeliac disease and for at least one week after starting GFD. The optimal timing of a diagnostic test for coeliac disease using gluten challenge and measurement of responses to A-gliadin 57–73 QE65 in the ELISpot assay is at least 2 weeks after commencing a GFD.

Interferon gamma-secreting T cells specific to A-gliadin 57–73 QE65 cannot be measured in the peripheral blood in untreated coeliacs, and can only be induced by gluten challenge after at least 2 weeks GFD (antigen exclusion). Therefore, timing of a diagnostic test using this methodology is crucial and further studies are needed for its optimization. These finding are consistent with functional anergy of T cells specific for the dominant epitope, A-gliadin 57–73 QE65, reversed by antigen exclusion (GFD). This phenomenon has not been previously demonstrated in a human disease, and supports the possibility that T cell anergy may be inducible with peptide therapy in coeliac disease.

REFERENCES

1. Molberg O, et al. Nature Med. 4, 713–717 (1998).
2. Quarsten H, et al. Eur. J. Immunol. 29, 2506–2514 (1999).
3. Greenberg C S et al. FASEB 5, 3071–3077 (1991).
4. Mantzaris G, Jewell D. Scand. J. Gastroenterol. 26, 392–398 (1991).
5. Mauri L, et al. Scand. J. Gastroenterol. 31, 247–253 (1996).
6. Bunce M, et al. Tissue Antigens 46, 355–367 (1995).
7. Olerup O. et al. Tissue antigens 41, 119–134 (1993).
8. Mullighan C G, et al. Tissue-Antigens. 50, 688–92 (1997).
9. Plebanski M et al. Eur. J. Immunol. 28, 4345–4355 (1998).

TABLE 1

A-Gliadin protein sequence (based on amino acid sequencing)

```
VRVPVPQLQP  QNPSQQQPQE  QVPLVQQQQF  PGQQQQFPPQ  QPYPQPQPFP  SQQPYLQLQP  FPQPQLPYPQ
1           11          21          31          41          51          61

PQSFPPQQPY  PQPQPQYSQP  QQPISQQQAQ  QQQQQQQQQQ  QQQILQQILQ  QQLIPCMDVV  LQQHNIAHAR
71          81          91          101         111         121         131

SQVLQQSTYQ  LLQELCCQHL  WQIPEQSQCQ  AIHNVVHAII  LHQQQKQQQQ  PSSQVSFQQP  LQQYPLGQGS
141         151         161         171         181         191         201

FRPSQQNPQA  QGSVQPQQLP  QFEEIRNLAL  QTLPAMCNVY  IAPYCTIAPF  GIFGTN
211         221         231         241         251         261
```

TABLE 2

Coeliac disease subjects studied

| | Age Sex | Gluten free diet | HLA-DQ2 | Bread challenge | Symptoms with bread |
|---|---|---|---|---|---|
| 1 | 64 f | 14 yr | Homozygote | 3 days | Abdominal pain, lethargy, month ulcers, diarrhoea |
| 2 | 57 m | 1 yr | Heterozygote | 10 days | Lethargy, nausea |
| 3 | 35 f | 7 yr | Heterozygote | 3 days | Nausea |
| 4 | 36 m | 6 wk | Homozygote | 3 days | Abdominal pain, mouth ulcers, diarrhoea |
| 5 | 26 m | 19 yr | Heterozygote | 3 days | None |
| 6 | 58 m | 35 yr | Heterozygote | 3 days | None |
| 7 | 55 m | 1 yr | Heterozygote | 3 days | Diarrhoea |
| 8 | 48 f | 15 yr | Homozygote | 3 days | Abdominal pain, diarrhoea |

TABLE 3

| Aminoacid at position 65 | Range | Mean |
|---|---|---|
| Glutamate | (100) | 100% |
| Asparagine | (50–84) | 70% |
| Aspartate | (50–94) | 65% |
| Alanine | (44–76) | 64% |
| Cysteine | (45–83) | 62% |
| Serine | (45–75) | 62% |
| Valine | (24–79) | 56% |
| Threonine | (46–66) | 55% |
| Glycine | (34–47) | 40% |
| Leucine | (8–46) | 33% |
| Glutamine | (16–21) | 19% |
| Isoleucine | (3–25) | 14% |
| Methionine | (3–32) | 14% |
| Phenylalanine | (0–33) | 12% |
| Histidine | (0–13) | 8% |
| Tyrosine | (0–17) | 8% |
| Tryptophan | (0–17) | 8% |
| Lysine | (0–11) | 4% |
| Proline | (0–4) | 2% |
| Arginine | (0–2) | 1% |

TABLE 4

| Elisopt response No TG | TG | Peptide sequence | Corresponding residues in gliadin protein sequences (Accession no.) |
|---|---|---|---|
| 8 (1–13) | | QLQPFPQPQLPYPQPQS | 57–73 α-Gliadin (*T. aestivum*) Q41545 |
| | 100 (100) | QLQPFPQPELPYPQPQS | 57–73 α-Gliadin (*T. aestivum*) Q41545 |
| 5 (1–7) | 53 (44–67) | QLQPFPQPQLPYSQPQP | 77–93 α/β-Gliadin precursor (*Tricetum aestivum*) P02863 |
| | | | 76–92 α-Gliadin (*T. aestivum*) Q41528 |
| | | | 77–93 α-Gliadin storage protein (*T. aestivum*) Q41531 |
| | | | 57–73 α-Gliadin mature peptide (*T. aestivum*) Q41533 |
| | | | 77–93 α-Gliadin precursor (*T. spelta*) Q9ZP09 |
| 12 (0–20) | 83 (61–113) | QLQPFPQPQLPYPQPQP | 77–93 α/β-Gliadin A-II precursor (*T. aestivum*) P0472 |
| 19 (0–33) | 83 (74.97) | QLQPFPQPQLPYPQPQL | 77–93 α/β-Gliadin A-IV precursor (*T. aestivum*) P04724 |
| | | | 77–93 α/β-Gliadin MMI precursor (*T. aestivum*) P18573 |
| 3 (0–7) | 109 (41–152) | PQLPYPQPQLPYPQPQP | 84–100 α/βGliadin A-IV precursor (*T. aestivum*) P04724 |
| ND | | PQLPYPQPQLPYPQPQL | 84–100 α/β-Gliadin MMI precursor (*T. aestivum*) P18573 |
| 0 (0–1) | 3 (0–7) | QLQPPLQPQLPYSQPQP | 77–93 α/β-Gliadin A-I precursor (*T. aestivum*) P04721 |
| | | | 77–93 α-Gliadin (*T. aestivum*) Q41509 |
| 0 (0–0) | 2 (0–7) | QLQPFSQPQLPYSQPQP | 77–93 α-Gliadin storage protein (*T. aestivum*) Q41530 |
| ND | | PQPQPFPPQLPYPQTQP | 77–93 α/β-Gliadin A-III precursor (*T. aestivum*) P04723 |
| 17 (0–40) | 24 (11–43) | PQPQPFPPQLPYPQPQS | 82–98 α/β-Gliadin A-V precursor (*T. aestivum*) P04725 |
| 10 (0–30) | 19 (11–33) | PQPQPFPPQLPYPQPPP | 82–98 α/β-Gliadin clone PW1215 precursor (*T. aestivum*) P04726 |
| | | | 82–98 α/β-Gliadin (*T. urartu*) Q41632 |

TABLE 4-continued

| Elisopt response No TG TG | Peptide sequence | Corresponding residues in gliadin protein sequences (Accession no.) |
|---|---|---|
| 10 (0-30) 21 (11-33) | PQPQPFLPQLPYPQPQS | 79-95 α/β-Gliadin clone PW8142 precursor (*T. aestivum*) P04726<br>79-95 α-Gliadin (*T. aestivum*) Q41529<br>79-95 α/β-Gliadin precursor (*T. aestivum*) Q41546 |

TABLE 5

T cell epitopes described in coeliac disease

| Source | Restriction | Frequency | Sequence* |
|---|---|---|---|
| Gamma-gliadin | DQ2 | 3/NS (iTCC) | QQLPQPEQPQQSFPEQERPF |
| Alpha-gliadin | DQ2 | 12/17 (iTCL) | QLQPFPQPELPY |
| Alpha-gliadin | DQ2 | 11/17 (iTCL) | PQPELPYPQPELPY |
| Alpha-gliadin | DQ2 | 1/23 (bTCC) | LGQQQPFPPQQPYPQPQPF |
| Alpha-gliadin | DQ8 | 3/NS (iTCC) | QQYPSGEGSFQPSQENPQ |
| Glutenin | DQ8 | 1/1 (iTCC) | GQQGYYPTSPQQSGQ |
| Alpha-gliadin | DQ2 | 11/12 in vivo | QLQPFPQPELPYPQPQS |

NS not stated in original publication, iTCC intestinal T cell clone, iTCL intestinal polyclonal T cell line, bTCC peripheral blood T cell clone
*All peptides are the products of transglutaminase modifying wild type gluten peptides except the fourth and sixth peptides

TABLE 6

Relative bioactivity of gliadin T cell epitopes in coeliac PBMC after gluten challenge

| | ELISpot response as % A-gliadin 57-73 QE65 (all 25 mcg/ml) | | |
|---|---|---|---|
| Sequence* | Wild type | Wildtype+tTG | E-substituted |
| QQLPQPEQPQQSFPEQERPF | 9 (3) | 18 (7) | 10 (5) |
| QLQPFPQPELPY | 6 (2) | 19 (1) | 8 (3) |
| PQPELPYPQPELPY | 13 (6) | 53 (8) | 48 (9) |
| QQYPSGEGSFQPSQENPQ | 10 (3) | 9 (3) | 14 (8) |
| QLQPFPQPELPYPQPQS | 18 (7) | 87 (7) | 100 |
| PQLPYPQPELPYPQPQP | 14 (4) | 80 (17) | 69 (20) |

*sequence refers that of transglutaminase (tTG) modified peptide and the T cell epitope. Wild type is the unmodified gliadin peptide. Data from 4 subjects. Blank was 5 (1)%.

TABLE 7

Polymorphisms of A-gliadin 57-73

A. Sequences derived from Nordic autumn wheat strain *Mjoelner*

| Alpha-gliadin protein (single letter code refers to FIG. 14 peptides) | Polymorphism |
|---|---|
| Q41545 A-gliadin (from sequenced protein) 57-73 (A) | QLQPFPQPQLPYPQPQS |
| Gli alpha 1,6: (EMBL: AJ133605 & AJ133602 58-74) (J) | QPQPFPPPQLPYPQTQP |
| Gli alpha 3,4,5: (EMBL: AJ133606, AJ133607, AJ133608 57-73) (I) | QLQPFPQPQLSYSQPQP |
| Gli alpha 7: (EMBL: AJ133604 57-73) (E) | QLQPFPRPQLPYPQPQP |
| Gli alpha 8,9,11: (EMBL:) (F) | QLQPFPQPQLYSQPQP |
| Gli alpha 10: (EMBL: AJ133610 57-73) (D) | QLQPFPQPQLPYLQPQS |

B. SWISSPROT and TREMBL scan (10.12.99) for gliadins containing the sequence: XXXXXXXPQLPYXXXXX

| Wheat (*Triticum aestivum* unless stated) gliadin accession number | Polymorphism |
|---|---|
| Q41545 A-gliadin (from sequenced protein) 57-73 (A) | QLQPFPQPQLPYPQPQS |
| SWISSPROT:<br>GDA0_WHEAT P02863 77-93 (F) | QLQPFPQPQLPYSQPQP |

TABLE 7-continued

Polymorphisms of A-gliadin 57-73

| | | |
|---|---|---|
| GDA1_WHEAT P04721 77–93 (G) | | QLQPFLQPQLPYSQPQP |
| GDA2_WHEAT P04722 77–93 (B) | | QLQPFQPQLPYPQPQP |
| GDA3_WHEAT P04723 77–93 (O) | | PQPQPFPPQLPYPQTQP |
| GDA4_WHEAT P04724 77–93 (C) | | QLQPFQPQLPYPQPQL |
| GDA4_WHEAT P04724 84–100 (K) | | PQLPYPQPQLPYPQPQP |
| GDA5_WHEAT P04725 82–98 (N) | | PQPQPFPQLPYPQPQS |
| GDA6_WHEAT P04726 82–98 (F) | | PQPQPFPPQLPYPQPPP |
| GDA7_WHEAT P04727 79–95 (M) | | PQPQPFLPQLPYPQPQS |
| GDA9_WHEAT P18573 77–93 (C) | | QLQPFQPQLPYPQPQL |
| GDA9_WHEAT P18573 84–100 (L) | | PQLPYPQPQLPYPQPQL |
| GDA9_WHEAT P18573 91–107 (K) | | PQLPYPQPQLPYPQPQP |
| TREMBL | | |
| Q41509 ALPHA-GLIADIN 77–93 (G) | | QLQPFLQPQLPYSQPQP |
| Q41528 ALPHA-GLIADIN 76–92 (F) | | QLQPFQPQLPYSQPQP |
| Q41529 ALPHA-GLIADIN 79–95 (M) | | PQPQPFLPQLPYPQPQS |
| Q41530 ALPHA-GLIADIN 77–93 (H) | | QLQPFSQPQLPYSQPQP |
| Q41531 ALPHA-GLIADIN 77–93 (F) | | QLQPFQPQLPYSQPQP |
| Q41533 ALPHA-GLIADIN 57–73 (F) | | QLQPFQPQLPYSQPQP |
| Q41546 ALPHA/BETA-GLIADIN 79–95 (M) | | PQPQPFLPQLPYPQPQS |
| Q41632 ALPHA/BETA-TYPE GLIADIN. *Triticum urartu* 82–98 (P) | | PQPQPFPPQLPYPQPPP |
| Q9ZP09 ALPHA-GLIADIN *Triticum elta* 77–93 (F) | | QLQPFQPQLPYSQPQP |

TABLE 8

Bioactivity of substituted variants of A-gliadin 57-73 QE65 (Subst) compared t unmodified A-gliadin 57-73 QE65 (G) (mean 100%, 95% CI 97–104) and blank (no peptide, bl) (mean 7.1%, 95% CI: 5.7–8.5)

| Subst | % | P vs G | P vs bl |
|---|---|---|---|
| *Super-agonists* | | | |
| Y61 | 129 | <0.0001 | |
| Y70 | 129 | 0.0006 | |
| *Agonists* | | | |
| W70 | 119 | 0.017 | |
| K57 | 118 | 0.02 | |
| Y59 | 117 | 0.04 | |
| A57 | 116 | 0.046 | |
| S70 | 116 | 0.045 | |
| K58 | 114 | 0.08 | |
| W59 | 110 | 0.21 | |
| A73 | 109 | 0.24 | |
| I59 | 108 | 0.37 | |
| G59 | 108 | 0.34 | |
| A58 | 108 | 0.35 | |
| W60 | 105 | 0.62 | |
| A59 | 104 | 0.61 | |
| K72 | 104 | 0.65 | |
| S59 | 103 | 0.76 | |
| K73 | 102 | 0.8 | |
| A70 | 102 | 0.81 | |
| Y60 | 101 | 0.96 | |
| A72 | 100 | 0.94 | |
| S63 | 98 | 0.67 | |
| K59 | 96 | 0.46 | |
| I60 | 96 | 0.5 | |
| G70 | 95 | 0.41 | |
| D65 | 95 | 0.44 | |
| E70 | 93 | 0.27 | |
| I63 | 92 | 0.19 | |
| S60 | 92 | 0.23 | |
| P59 | 88 | 0.08 | |
| M63 | 87 | 0.03 | |
| K71 | 85 | 0.047 | |
| V62 | 84 | 0.04 | |
| I70 | 84 | 0.04 | |
| I61 | 83 | 0.01 | |
| V68 | 82 | 0.0045 | |
| E59 | 81 | 0.01 | |
| *Partial agonists* | | | |
| W61 | 79 | 0.002 | |
| A60 | 78 | 0.002 | |
| Y62 | 78 | 0.006 | |
| G60 | 77 | 0.003 | |
| A71 | 77 | 0.003 | |
| W62 | 76 | 0.0009 | |
| Q60 | 76 | 0.001 | |
| L63 | 74 | 0.0002 | |
| I62 | 74 | 0.0005 | |
| K70 | 74 | 0.001 | |
| H61 | 72 | <0.0001 | |
| W68 | 72 | <0.0001 | |
| F62 | 71 | 0.001 | |
| V63 | 70 | <0.0001 | |
| S69 | 70 | <0.0001 | |
| H63 | 70 | <0.0001 | |
| F63 | 70 | 0.008 | |
| P70 | 69 | <0.0001 | |
| T62 | 69 | <0.0001 | |
| L61 | 69 | <0.0001 | |
| S61 | 69 | <0.0001 | |
| T61 | 69 | <0.0001 | |
| T63 | 69 | <0.0001 | |
| M66 | 68 | <0.0001 | |
| T69 | 67 | <0.0001 | |
| K60 | 66 | <0.0001 | |
| S62 | 66 | <0.0001 | |
| M61 | 66 | <0.0001 | |
| P61 | 65 | <0.0001 | |
| M62 | 64 | <0.0001 | |
| Q61 | 64 | <0.0001 | |
| G61 | 64 | <0.0001 | |
| A63 | 64 | <0.0001 | |
| L62 | 60 | <0.0001 | |
| I68 | 60 | <0.0001 | |
| S67 | 59 | <0.0001 | |
| N61 | 59 | <0.0001 | |
| I69 | 59 | <0.0001 | |
| V61 | 58 | <0.0001 | |
| D61 | 58 | <0.0001 | |
| E60 | 57 | <0.0001 | |
| A61 | 57 | <0.0001 | |
| Q62 | 56 | <0.0001 | |
| F68 | 56 | <0.0001 | |
| N65 | 56 | <0.0001 | |

TABLE 8-continued

Bioactivity of substituted variants of A-gliadin 57-73 QE65 (Subst) compared t unmodified A-gliadin 57-73 QE65 (G) (mean 100%, 95% CI 97–104) and blank (no peptide, bl) (mean 7.1%, 95% CI: 5.7–8.5)

| Subst | % | P vs G | P vs bl |
|---|---|---|---|
| A62 | 56 | <0.0001 | |
| A68 | 53 | <0.0001 | |
| P66 | 53 | <0.0001 | |
| R61 | 53 | <0.0001 | |
| S68 | 53 | <0.0001 | |
| Y63 | 52 | <0.0001 | |
| N69 | 51 | <0.0001 | |
| E63 | 51 | <0.0001 | |
| T64 | 51 | <0.0001 | |
| T67 | 51 | <0.0001 | |
| Y69 | 50 | <0.0001 | |
| D63 | 50 | <0.0001 | |
| A65 | 49 | <0.0001 | |
| K61 | 49 | <0.0001 | |
| I66 | 49 | <0.0001 | |
| T68 | 48 | <0.0001 | |
| S65 | 48 | <0.0001 | |
| L68 | 48 | <0.0001 | |
| Q68 | 48 | <0.0001 | |
| H62 | 47 | <0.0001 | |
| G69 | 47 | <0.0001 | |
| N63 | 47 | <0.0001 | |
| H68 | 47 | <0.0001 | |
| M68 | 46 | <0.0001 | |
| D68 | 46 | <0.0001 | |
| V69 | 46 | <0.0001 | |
| G63 | 45 | <0.0001 | |
| V64 | 45 | <0.0001 | |
| E61 | 45 | <0.0001 | |
| A69 | 43 | <0.0001 | |
| R62 | 42 | <0.0001 | |
| G68 | 42 | <0.0001 | |
| A64 | 42 | <0.0001 | |
| C65 | 42 | <0.0001 | |
| N67 | 41 | <0.0001 | |
| W63 | 41 | <0.0001 | |
| F69 | 41 | <0.0001 | |
| N68 | 40 | <0.0001 | |
| V66 | 40 | <0.0001 | |
| H69 | 40 | <0.0001 | |
| M69 | 40 | <0.0001 | |
| R69 | 40 | <0.0001 | |
| W69 | 40 | <0.0001 | |
| Q69 | 39 | <0.0001 | |
| L67 | 38 | <0.0001 | |
| K69 | 38 | <0.0001 | |
| K62 | 38 | <0.0001 | |
| E67 | 37 | <0.0001 | |
| L69 | 37 | <0.0001 | |
| S64 | 36 | <0.0001 | |
| G62 | 36 | <0.0001 | |
| E69 | 36 | <0.0001 | |
| E68 | 36 | <0.0001 | |
| V67 | 35 | <0.0001 | |
| D62 | 35 | <0.0001 | |
| R68 | 34 | <0.0001 | |
| Q66 | 34 | <0.0001 | |
| A67 | 33 | <0.0001 | |
| N62 | 32 | <0.0001 | |
| F66 | 31 | <0.0001 | |
| E62 | 31 | <0.0001 | |
| D69 | 31 | <0.0001 | |
| D67 | 30 | <0.0001 | |
| M67 | 29 | <0.0001 | |
| Y66 | 28 | <0.0001 | |
| I67 | 28 | <0.0001 | |
| H65 | 26 | <0.0001 | |
| P68 | 26 | <0.0001 | |
| Y64 | 25 | <0.0001 | |
| EK65 | 25 | <0.0001 | |
| T66 | 25 | <0.0001 | |
| N66 | 24 | <0.0001 | |
| R64 | 24 | <0.0001 | |
| K63 | 23 | <0.0001 | |
| V65 | 23 | <0.0001 | |
| H66 | 23 | <0.0001 | |
| H67 | 22 | <0.0001 | |
| L64 | 22 | <0.0001 | |
| S66 | 22 | <0.0001 | |
| F67 | 21 | <0.0001 | |
| W66 | 21 | <0.0001 | |
| G64 | 21 | <0.0001 | |
| G65 | 21 | <0.0001 | |
| D64 | 21 | <0.0001 | |
| I65 | 21 | <0.0001 | |
| M64 | 20 | <0.0001 | <0.0001 |
| G67 | 19 | <0.0001 | <0.0001 |
| T65 | 19 | <0.0001 | 0.003 |
| A66 | 19 | <0.0001 | <0.0001 |
| I64 | 19 | <0.0001 | 0.0003 |
| R63 | 19 | <0.0001 | <0.0001 |
| W67 | 19 | <0.0001 | <0.0001 |
| K68 | 18 | <0.0001 | <0.0001 |
| H64 | 18 | <0.0001 | <0.0001 |
| W64 | 18 | <0.0001 | 0.0001 |
| Q65 | 18 | <0.0001 | 0.0002 |
| F64 | 16 | <0.0001 | 0.0008 |
| L65 | 16 | <0.0001 | 0.0022 |
| N64 | 16 | <0.0001 | <0.0001 |
| F65 | 16 | <0.0001 | 0.12 |
| Q67 | 15 | <0.0001 | 0.0012 |
| M65 | 14 | <0.0001 | 0.015 |
| D66 | 14 | <0.0001 | 0.013 |
| R67 | 14 | <0.0001 | 0.002 |
| Non-agonists | | | |
| P63 | 13 | <0.0001 | 0.012 |
| E64 | 12 | <0.0001 | 0.053 |
| W65 | 11 | <0.0001 | 0.24 |
| Q64 | 11 | <0.0001 | 0.15 |
| G66 | 11 | <0.0001 | 0.07 |
| R65 | 11 | <0.0001 | 0.26 |
| Y67 | 10 | <0.0001 | 0.13 |
| E66 | 10 | <0.0001 | 0.17 |
| K66 | 10 | <0.0001 | 0.21 |
| R66 | 10 | <0.0001 | 0.23 |
| K67 | 10 | <0.0001 | 0.11 |
| P65 | 8 | <0.0001 | 0.57 |
| K64 | 8 | <0.0001 | 0.82 |
| K65 | 8 | <0.0001 | 0.63 |
| Y65 | 7 | <0.0001 | 0.9 |

TABLE 9

Antagonism of A-gliadin 57-73 QE65 interferon gamma ELISPOT response by substituted variants of A-gliadin 57-73 QE65 (Subst) (P is significance level in unpaired t-test). Agonist activity (% agonist) of peptides compared to A-gliadin 57-73 QE65 is also shown.

| Subst | % Inhibit. | P | % agonist. |
|---|---|---|---|
| Antagonists | | | |
| 65T | 28 | 0.004 | 19 |
| 67M | 27 | 0.0052 | 29 |
| 64W | 26 | 0.007 | 18 |
| 67W | 25 | 0.0088 | 19 |
| Potential antagonists | | | |
| 67I | 24 | 0.013 | 10 |
| 67Y | 24 | 0.013 | 21 |
| 64G | 21 | 0.03 | 21 |
| 64D | 21 | 0.029 | 16 |

TABLE 9-continued

Antagonism of A-gliadin 57-73 QE65 interferon gamma ELISPOT response by substituted variants of A-gliadin 57-73 QE65 (Subst) (P is significance level in unpaired t-test). Agonist activity (% agonist) of peptides compared to A-gliadin 57-73 QE65 is also shown.

| Subst | % Inhibit. | P | % agonist. |
|---|---|---|---|
| 65L | 20 | 0.046 | 26 |
| 66N | 20 | 0.037 | 24 |
| 65H | 20 | 0.038 | 16 |
| 64N | 19 | 0.05 | 16 |
| 64Y | 19 | 0.06 | 25 |
| 66Y | 19 | 0.048 | 28 |
| 64E | 19 | 0.049 | 12 |
| 67A | 18 | 0.058 | 30 |
| 67H | 18 | 0.052 | 22 |
| | Non-antagonists | | |
| 65V | 17 | 0.07 | 23 |
| 65I | 17 | 0.086 | 21 |
| 66T | 17 | 0.069 | 25 |
| 65W | 15 | 0.11 | 11 |
| 67R | 15 | 0.13 | 14 |
| 65P | 15 | 0.13 | 8 |
| 65K | 15 | 0.11 | 8 |
| 66W | 15 | 0.12 | 21 |
| 67G | 14 | 0.14 | 19 |
| 66A | 14 | 0.14 | 19 |
| 65R | 13 | 0.18 | 11 |
| 65M | 13 | 0.16 | 14 |
| 68P | 13 | 0.16 | 26 |
| 63R | 13 | 0.19 | 19 |
| 66G | 12 | 0.19 | 11 |
| 65Q | 12 | 0.2 | 18 |
| 65Y | 12 | 0.22 | 7 |
| 66S | 12 | 0.22 | 22 |
| 67F | 11 | 0.25 | 21 |
| 66R | 10 | 0.29 | 10 |
| 67K | 10 | 0.29 | 10 |
| 64F | 10 | 0.29 | 16 |
| 65F | 9 | 0.41 | 16 |
| 63P | 8 | 0.42 | 13 |
| 65EK | 8 | 0.39 | 25 |
| 64Q | 7 | 0.49 | 11 |
| 641 | 5 | 0.6 | 21 |
| 68K | 5 | 0.56 | 19 |
| 67Q | 5 | 0.61 | 18 |
| 65G | 5 | 0.62 | 15 |
| 64M | 4 | 0.7 | 20 |
| 66H | 4 | 0.66 | 23 |
| 66E | 3 | 0.76 | 10 |
| 66D | 1 | 0.9 | 14 |
| 63K | 1 | 0.88 | 23 |
| 64H | 1 | 0.93 | 18 |
| 66K | 0 | 0.98 | 10 |
| 64K | −2 | 0.88 | 8 |
| 64L | −11 | 0.26 | 22 |

TABLE 10

Inhibition of A-gliadin 57-73 QE65 interferon gamma ELISPOT response by peptides known to bind HLA-DQ2 (P is significance level in unpaired t-test).

| Peptide | % Inhibit. | P |
|---|---|---|
| TP | 31 | <0.0001 |
| HLA1a | 0 | 0.95 |

TABLE 11

Antagonism of A-gliadin 57-73 QE65 interferon gamma ELISpot response by naturally occurring polymorphisms of A-gliadin 57-73 QE65 (P is significance level in unpaired t-test).

| A-gliadin 57-73 QE65 | polymorphism | % Inhibit. | P |
|---|---|---|---|
| P04725 82-98 QE90 | PQPQPFPPELPYPQPQS | 19 | 0.009 |
| Q41509 77-93 QE85 | QLQPFLQPELPYSQPQP | 11 | 0.15 |
| Gliα 1,6 58-74 QE66 | QPQPFPPPELPYPQTQP | 11 | 0.11 |
| P04723 77-93 QE85 | PQPQPFPPELPYPQTQP | 10 | 0.14 |
| Gliα 3-5 57-73 QE65 | QLQPFPQPELSYSQPQP | 7 | 0.34 |
| P02863 77-93 QE85 | QLQPFPQPELPYSQPQP | 6 | 0.35 |
| Q41509 77-93 QE85 | QLQPFLQPELPYSQPQP | 6 | 0.41 |
| P04727 79-95 QE65 | PQPQPFLPELPYPQPQS | 6 | 0.39 |
| P04726 82-98 QE90 | PQPQPFPPELPYPQPPP | 5 | 0.43 |

The invention claimed is:

1. An isolated peptide comprising the amino acid sequence SEQ ID NO:1.

2. The peptide of claim 1 wherein the peptide is 7 to 50 amino acids in length.

3. The peptide of claim 1 comprising the amino acid sequence SEQ ID NO:2.

4. The peptide of claim 3 wherein the peptide is up to 50 amino acids in length.

5. A fusion protein comprising SEQ ID NO:1 and a non-gliadin sequence.

6. A kit comprising a peptide of claim 1 or 5 and a means to detect the recognition of the peptide by a T cell.

7. The kit of claim 6 wherein the means to detect recognition comprises an antibody to IFN-γ.

8. The kit of claim 7 wherein the antibody is immobilised on a solid support and, optionally, comprises a means to detect any complexes formed between the antibody and IFN-γ.

9. A method of diagnosing coeliac disease or susceptibility to coeliac disease in an individual comprising:
   a) contacting the individual or a sample from the individual with a peptide of claim 1 or 5; and
   b) determining whether a T cell in the sample recognises the peptide, wherein recognition by the T cell indicates that the individual has or is susceptible to coeliac disease.

10. The method of claim 9 wherein a) comprises administering the peptide to the skin of the individual, and b) comprises detecting the presence of inflammation at the site of administration, wherein detection of inflammation indicates that the T cell of the individual recognises the peptide.

11. The method of claim 9 wherein the sample is a blood sample.

12. The method of 9 wherein the T cell is not re-stimulated in an antigen specific manner in vitro before determining whether the T cell in the sample recognises the peptide.

13. The method of claim 9 wherein the recognition of the peptide by the T cell is determined by detecting the secretion of a cytokine from the T cell.

14. The method of claim 13 wherein the cytokine is IFN-γ.

15. The method of claim 13 wherein the cytokine is detected by allowing the cytokine to bind to an immobilised antibody specific to the cytokine and then detecting the presence of any complex formed between the antibody and cytokine.

16. The method of claim 9 wherein b) comprises measuring whether the peptide binds a T cell receptor.

17. An isolated product comprising two or more of:
   a peptide comprising the amino acid sequence SEQ ID NO:1;
   a peptide 7 to 50 amino acids in length comprising the amino acid sequence SEQ ID NO:1;
   a peptide comprising the amino acid sequence SEQ ID NO:2;
   a peptide up to 50 amino acids in length comprising the amino acid sequence SEQ ID NO:2; and
   a fusion protein comprising SEQ ID NO:1 and a non-gliadin sequence.

18. A composition comprising a peptide or a fusion protein, and a pharmaceutically acceptable carrier or diluent, wherein the peptide is:
   a peptide comprising the amino acid sequence SEQ ID NO:1;
   a peptide 7 to 50 amino acids in length comprising the amino acid sequence SEQ ID NO:1;
   a peptide comprising the amino acid sequence SEQ ID NO:2; or
   a peptide up to 50 amino acids in length comprising the amino acid sequence SEQ ID NO:2; and
   wherein the fusion protein comprises SEQ ID NO:1 and a non-gliadin sequence.

19. A method of diagnosing coeliac disease or susceptibility to coeliac disease in an individual comprising detecting the presence of an antibody that binds to a peptide comprising SEQ ID NO:1 in a sample from the individual, wherein the presence of the antibody indicates that the individual has or is susceptible to coeliac disease.

\* \* \* \* \*

SEQUENCE LISTING

<160> NUMBER OF SEQ ID NOS: 78

<210> SEQ ID NO 1
<211> LENGTH: 7
<212> TYPE: PRT
<213> ORGANISM: Homo sapiens

<400> SEQUENCE: 1

Pro Gln Pro Glu Leu Pro Tyr

-continued

```
1               5

<210> SEQ ID NO 2
<211> LENGTH: 17
<212> TYPE: PRT
<213> ORGANISM: Homo sapiens

<400> SEQUENCE: 2

Gln Leu Gln Pro Phe Pro Gln Pro Glu Leu Pro Tyr Pro Gln Pro Gln
1               5                   10                  15

Ser

<210> SEQ ID NO 3
<211> LENGTH: 266
<212> TYPE: PRT
<213> ORGANISM: plant

<400> SEQUENCE: 3

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Pro Gly
                20                  25                  30

Gln Gln Gln Gln Phe Pro Pro Gln Gln Pro Tyr Pro Gln Pro Gln Pro
                35                  40                  45

Phe Pro Ser Gln Gln Pro Tyr Leu Gln Leu Gln Pro Phe Pro Gln Pro
            50                  55                  60

Gln Leu Pro Tyr Pro Gln Pro Gln Ser Phe Pro Pro Gln Gln Pro Tyr
65              70                  75                  80

Pro Gln Pro Gln Pro Gln Tyr Ser Gln Pro Gln Gln Pro Ile Ser Gln
                85                  90                  95

Gln Gln Ala Gln Gln Gln Gln Gln Gln Gln Gln Gln Gln Gln Gln Gln
                100                 105                 110

Gln Ile Leu Gln Gln Ile Leu Gln Gln Gln Leu Ile Pro Cys Met Asp
            115                 120                 125

Val Val Leu Gln Gln His Asn Ile Ala His Ala Arg Ser Gln Val Leu
130             135                 140

Gln Gln Ser Thr Tyr Gln Leu Leu Gln Glu Leu Cys Cys Gln His Leu
145             150                 155                 160

Trp Gln Ile Pro Glu Gln Ser Gln Cys Gln Ala Ile His Asn Val Val
                165                 170                 175

His Ala Ile Ile Leu His Gln Gln Gln Lys Gln Gln Gln Gln Pro Ser
            180                 185                 190

Ser Gln Val Ser Phe Gln Gln Pro Leu Gln Gln Tyr Pro Leu Gly Gln
            195                 200                 205

Gly Ser Phe Arg Pro Ser Gln Gln Asn Pro Gln Ala Gln Gly Ser Val
            210                 215                 220

Gln Pro Gln Gln Leu Pro Gln Phe Glu Glu Ile Arg Asn Leu Ala Leu
225             230                 235                 240

Gln Thr Leu Pro Ala Met Cys Asn Val Tyr Ile Ala Pro Tyr Cys Thr
                245                 250                 255

Ile Ala Pro Phe Gly Ile Phe Gly Thr Asn
            260                 265

<210> SEQ ID NO 4
<211> LENGTH: 5
<212> TYPE: PRT
<213> ORGANISM: Homo sapiens
```

```
<400> SEQUENCE: 4

Pro Gln Leu Pro Tyr
1               5

<210> SEQ ID NO 5
<211> LENGTH: 5
<212> TYPE: PRT
<213> ORGANISM: Homo sapiens

<400> SEQUENCE: 5

Gln Pro Gln Leu Pro
1               5

<210> SEQ ID NO 6
<211> LENGTH: 7
<212> TYPE: PRT
<213> ORGANISM: Homo sapiens

<400> SEQUENCE: 6

Pro Gln Pro Gln Leu Pro Tyr
1               5

<210> SEQ ID NO 7
<211> LENGTH: 20
<212> TYPE: PRT
<213> ORGANISM: Homo sapiens

<400> SEQUENCE: 7

Leu Gln Leu Gln Pro Phe Pro Gln Pro Gln Leu Pro Tyr Pro Gln Pro
1               5                   10                  15

Gln Ser Phe Pro
            20

<210> SEQ ID NO 8
<211> LENGTH: 20
<212> TYPE: PRT
<213> ORGANISM: Homo sapiens

<400> SEQUENCE: 8

Leu Gln Leu Gln Pro Phe Pro Gln Pro Glu Leu Pro Tyr Pro Gln Pro
1               5                   10                  15

Gln Ser Phe Pro
            20

<210> SEQ ID NO 9
<211> LENGTH: 17
<212> TYPE: PRT
<213> ORGANISM: Homo sapiens

<400> SEQUENCE: 9

Gln Leu Gln Pro Phe Pro Gln Pro Gln Leu Pro Tyr Pro Gln Pro Gln
1               5                   10                  15

Ser

<210> SEQ ID NO 10
<211> LENGTH: 17
<212> TYPE: PRT
<213> ORGANISM: Homo sapiens

<400> SEQUENCE: 10

Gln Leu Gln Pro Phe Pro Gln Pro Glu Leu Pro Tyr Pro Gln Pro Gln
1               5                   10                  15
```

```
<210> SEQ ID NO 11
<211> LENGTH: 17
<212> TYPE: PRT
<213> ORGANISM: Homo sapiens

<400> SEQUENCE: 11

Pro Gln Pro Gln Pro Phe Pro Pro Glu Leu Pro Tyr Pro Gln Pro Gln
 1               5                  10                  15
Ser

<210> SEQ ID NO 12
<211> LENGTH: 17
<212> TYPE: PRT
<213> ORGANISM: Homo sapiens

<400> SEQUENCE: 12

Gln Leu Gln Pro Phe Pro Gln Pro Glu Leu Pro Tyr Pro Gln Pro Glu
 1               5                  10                  15
Ser

<210> SEQ ID NO 13
<211> LENGTH: 17
<212> TYPE: PRT
<213> ORGANISM: Homo sapiens

<400> SEQUENCE: 13

Gln Leu Gln Pro Phe Pro Gln Pro Glu Leu Pro Tyr Pro Gln Pro Glu
 1               5                  10                  15
Ser

<210> SEQ ID NO 14
<211> LENGTH: 17
<212> TYPE: PRT
<213> ORGANISM: Homo sapiens

<400> SEQUENCE: 14

Glu Leu Gln Pro Phe Pro Gln Pro Glu Leu Pro Tyr Pro Gln Pro Glu
 1               5                  10                  15
Ser

<210> SEQ ID NO 15
<211> LENGTH: 17
<212> TYPE: PRT
<213> ORGANISM: Homo sapiens

<400> SEQUENCE: 15

Gln Pro Gln Pro Phe Pro Pro Pro Gln Leu Pro Tyr Pro Gln Thr Gln
 1               5                  10                  15
Pro

<210> SEQ ID NO 16
<211> LENGTH: 17
<212> TYPE: PRT
<213> ORGANISM: Homo sapiens

<400> SEQUENCE: 16

Gln Leu Gln Pro Phe Pro Gln Pro Gln Leu Ser Tyr Ser Gln Pro Gln
 1               5                  10                  15
```

Pro

<210> SEQ ID NO 17
<211> LENGTH: 17
<212> TYPE: PRT
<213> ORGANISM: Homo sapiens

<400> SEQUENCE: 17

Gln Leu Gln Pro Phe Pro Arg Pro Gln Leu Pro Tyr Pro Gln Pro Gln
1               5                   10                  15

Pro

<210> SEQ ID NO 18
<211> LENGTH: 17
<212> TYPE: PRT
<213> ORGANISM: Homo sapiens

<400> SEQUENCE: 18

Gln Leu Gln Pro Phe Pro Gln Pro Gln Leu Pro Tyr Ser Gln Pro Gln
1               5                   10                  15

Pro

<210> SEQ ID NO 19
<211> LENGTH: 17
<212> TYPE: PRT
<213> ORGANISM: Homo sapiens

<400> SEQUENCE: 19

Gln Leu Gln Pro Phe Pro Gln Pro Gln Leu Pro Tyr Leu Gln Pro Gln
1               5                   10                  15

Ser

<210> SEQ ID NO 20
<211> LENGTH: 17
<212> TYPE: PRT
<213> ORGANISM: Homo sapiens

<400> SEQUENCE: 20

Gln Leu Gln Pro Phe Pro Gln Pro Gln Leu Pro Tyr Ser Gln Pro Gln
1               5                   10                  15

Pro

<210> SEQ ID NO 21
<211> LENGTH: 17
<212> TYPE: PRT
<213> ORGANISM: Homo sapiens

<400> SEQUENCE: 21

Gln Leu Gln Pro Phe Leu Gln Pro Gln Leu Pro Tyr Ser Gln Pro Gln
1               5                   10                  15

Pro

<210> SEQ ID NO 22
<211> LENGTH: 17
<212> TYPE: PRT
<213> ORGANISM: Homo sapiens

<400> SEQUENCE: 22

Gln Leu Gln Pro Phe Pro Gln Pro Gln Leu Pro Tyr Pro Gln Pro Gln
1               5                   10                  15

Pro

```
<210> SEQ ID NO 23
<211> LENGTH: 17
<212> TYPE: PRT
<213> ORGANISM: Homo sapiens

<400> SEQUENCE: 23

Pro Gln Pro Gln Pro Phe Pro Pro Gln Leu Pro Tyr Pro Gln Thr Gln
1               5                   10                  15

Pro

<210> SEQ ID NO 24
<211> LENGTH: 17
<212> TYPE: PRT
<213> ORGANISM: Homo sapiens

<400> SEQUENCE: 24

Gln Leu Gln Pro Phe Pro Gln Pro Gln Leu Pro Tyr Pro Gln Pro Gln
1               5                   10                  15

Leu

<210> SEQ ID NO 25
<211> LENGTH: 17
<212> TYPE: PRT
<213> ORGANISM: Homo sapiens

<400> SEQUENCE: 25

Pro Gln Leu Pro Tyr Pro Gln Pro Gln Leu Pro Tyr Pro Gln Pro Gln
1               5                   10                  15

Pro

<210> SEQ ID NO 26
<211> LENGTH: 17
<212> TYPE: PRT
<213> ORGANISM: Homo sapiens

<400> SEQUENCE: 26

Pro Gln Pro Gln Pro Phe Pro Pro Gln Leu Pro Tyr Pro Gln Pro Gln
1               5                   10                  15

Ser

<210> SEQ ID NO 27
<211> LENGTH: 17
<212> TYPE: PRT
<213> ORGANISM: Homo sapiens

<400> SEQUENCE: 27

Pro Gln Pro Gln Pro Phe Pro Pro Gln Leu Pro Tyr Pro Gln Pro Pro
1               5                   10                  15

Pro

<210> SEQ ID NO 28
<211> LENGTH: 17
<212> TYPE: PRT
<213> ORGANISM: Homo sapiens

<400> SEQUENCE: 28

Pro Gln Pro Gln Pro Phe Leu Pro Gln Leu Pro Tyr Pro Gln Pro Gln
1               5                   10                  15

Ser
```

<210> SEQ ID NO 29
<211> LENGTH: 17
<212> TYPE: PRT
<213> ORGANISM: Homo sapiens

<400> SEQUENCE: 29

Gln Leu Gln Pro Phe Pro Gln Pro Gln Leu Pro Tyr Pro Gln Pro Gln
1               5                   10                  15

Leu

<210> SEQ ID NO 30
<211> LENGTH: 17
<212> TYPE: PRT
<213> ORGANISM: Homo sapiens

<400> SEQUENCE: 30

Pro Gln Leu Pro Tyr Pro Gln Pro Gln Leu Pro Tyr Pro Gln Pro Gln
1               5                   10                  15

Leu

<210> SEQ ID NO 31
<211> LENGTH: 17
<212> TYPE: PRT
<213> ORGANISM: Homo sapiens

<400> SEQUENCE: 31

Pro Gln Leu Pro Tyr Pro Gln Pro Gln Leu Pro Tyr Pro Gln Pro Gln
1               5                   10                  15

Pro

<210> SEQ ID NO 32
<211> LENGTH: 17
<212> TYPE: PRT
<213> ORGANISM: Homo sapiens

<400> SEQUENCE: 32

Gln Leu Gln Pro Phe Leu Gln Pro Gln Leu Pro Tyr Ser Gln Pro Gln
1               5                   10                  15

Pro

<210> SEQ ID NO 33
<211> LENGTH: 17
<212> TYPE: PRT
<213> ORGANISM: Homo sapiens

<400> SEQUENCE: 33

Gln Leu Gln Pro Phe Pro Gln Pro Gln Leu Pro Tyr Ser Gln Pro Gln
1               5                   10                  15

Pro

<210> SEQ ID NO 34
<211> LENGTH: 17
<212> TYPE: PRT
<213> ORGANISM: Homo sapiens

<400> SEQUENCE: 34

Pro Gln Pro Gln Pro Phe Leu Pro Gln Leu Pro Tyr Pro Gln Pro Gln
1               5                   10                  15

Ser

<210> SEQ ID NO 35
<211> LENGTH: 17
<212> TYPE: PRT
<213> ORGANISM: Homo sapiens

<400> SEQUENCE: 35

Gln Leu Gln Pro Phe Ser Gln Pro Gln Leu Pro Tyr Ser Gln Pro Gln
1               5                   10                  15

Pro

<210> SEQ ID NO 36
<211> LENGTH: 17
<212> TYPE: PRT
<213> ORGANISM: Homo sapiens

<400> SEQUENCE: 36

Gln Leu Gln Pro Phe Pro Gln Pro Gln Leu Pro Tyr Ser Gln Pro Gln
1               5                   10                  15

Pro

<210> SEQ ID NO 37
<211> LENGTH: 17
<212> TYPE: PRT
<213> ORGANISM: Homo sapiens

<400> SEQUENCE: 37

Gln Leu Gln Pro Phe Pro Gln Pro Gln Leu Pro Tyr Ser Gln Pro Gln
1               5                   10                  15

Pro

<210> SEQ ID NO 38
<211> LENGTH: 17
<212> TYPE: PRT
<213> ORGANISM: Homo sapiens

<400> SEQUENCE: 38

Pro Gln Pro Gln Pro Phe Leu Pro Gln Leu Pro Tyr Pro Gln Pro Gln
1               5                   10                  15

Ser

<210> SEQ ID NO 39
<211> LENGTH: 17
<212> TYPE: PRT
<213> ORGANISM: Homo sapiens

<400> SEQUENCE: 39

Pro Gln Pro Gln Pro Phe Pro Pro Gln Leu Pro Tyr Pro Gln Pro Pro
1               5                   10                  15

Pro

<210> SEQ ID NO 40
<211> LENGTH: 17
<212> TYPE: PRT
<213> ORGANISM: Homo sapiens

<400> SEQUENCE: 40

Gln Leu Gln Pro Phe Pro Gln Pro Gln Leu Pro Tyr Ser Gln Pro Gln
1               5                   10                  15

Pro

<210> SEQ ID NO 41

<211> LENGTH: 17
<212> TYPE: PRT
<213> ORGANISM: Homo sapiens

<400> SEQUENCE: 41

Gln Leu Gln Pro Phe Pro Gln Pro Gln Leu Pro Tyr Pro Gln Pro Gln
1               5                   10                  15

Pro

<210> SEQ ID NO 42
<211> LENGTH: 17
<212> TYPE: PRT
<213> ORGANISM: Homo sapiens

<400> SEQUENCE: 42

Gln Leu Gln Pro Phe Pro Gln Pro Gln Leu Pro Tyr Ser Gln Pro Gln
1               5                   10                  15

Pro

<210> SEQ ID NO 43
<211> LENGTH: 17
<212> TYPE: PRT
<213> ORGANISM: Homo sapiens

<400> SEQUENCE: 43

Gln Leu Gln Pro Phe Pro Gln Pro Gln Leu Pro Tyr Pro Gln Pro Gln
1               5                   10                  15

Leu

<210> SEQ ID NO 44
<211> LENGTH: 17
<212> TYPE: PRT
<213> ORGANISM: Homo sapiens

<400> SEQUENCE: 44

Gln Leu Gln Pro Phe Leu Gln Pro Gln Leu Pro Tyr Ser Gln Pro Gln
1               5                   10                  15

Pro

<210> SEQ ID NO 45
<211> LENGTH: 17
<212> TYPE: PRT
<213> ORGANISM: Homo sapiens

<400> SEQUENCE: 45

Gln Leu Gln Pro Phe Ser Gln Pro Gln Leu Pro Tyr Ser Gln Pro Gln
1               5                   10                  15

Pro

<210> SEQ ID NO 46
<211> LENGTH: 17
<212> TYPE: PRT
<213> ORGANISM: Homo sapiens

<400> SEQUENCE: 46

Pro Gln Pro Gln Pro Phe Pro Pro Gln Leu Pro Tyr Pro Gln Thr Gln
1               5                   10                  15

Pro

<210> SEQ ID NO 47
<211> LENGTH: 17

```
<212> TYPE: PRT
<213> ORGANISM: Homo sapiens

<400> SEQUENCE: 47

Pro Gln Pro Gln Pro Phe Leu Pro Gln Leu Pro Tyr Pro Gln Pro Gln
1               5                   10                  15

Ser

<210> SEQ ID NO 48
<211> LENGTH: 17
<212> TYPE: PRT
<213> ORGANISM: Homo sapiens

<400> SEQUENCE: 48

Pro Gln Pro Gln Pro Phe Pro Pro Gln Leu Pro Tyr Pro Gln Pro Gln
1               5                   10                  15

Ser

<210> SEQ ID NO 49
<211> LENGTH: 17
<212> TYPE: PRT
<213> ORGANISM: Homo sapiens

<400> SEQUENCE: 49

Pro Gln Pro Gln Pro Phe Pro Pro Gln Leu Pro Tyr Pro Gln Pro Gln
1               5                   10                  15

Pro

<210> SEQ ID NO 50
<211> LENGTH: 17
<212> TYPE: PRT
<213> ORGANISM: Homo sapiens

<400> SEQUENCE: 50

Pro Gln Leu Pro Tyr Pro Gln Pro Gln Leu Pro Tyr Pro Gln Pro Gln
1               5                   10                  15

Pro

<210> SEQ ID NO 51
<211> LENGTH: 17
<212> TYPE: PRT
<213> ORGANISM: Homo sapiens

<400> SEQUENCE: 51

Pro Gln Leu Pro Tyr Pro Gln Pro Gln Leu Pro Tyr Pro Gln Pro Gln
1               5                   10                  15

Leu

<210> SEQ ID NO 52
<211> LENGTH: 20
<212> TYPE: PRT
<213> ORGANISM: Homo sapiens

<400> SEQUENCE: 52

Gln Gln Leu Pro Gln Pro Glu Gln Pro Gln Gln Ser Phe Pro Glu Gln
1               5                   10                  15

Glu Arg Pro Phe
            20

<210> SEQ ID NO 53
<211> LENGTH: 12
```

```
<212> TYPE: PRT
<213> ORGANISM: Homo sapiens

<400> SEQUENCE: 53

Gln Leu Gln Pro Phe Pro Gln Pro Glu Leu Pro Tyr
1               5                   10

<210> SEQ ID NO 54
<211> LENGTH: 14
<212> TYPE: PRT
<213> ORGANISM: Homo sapiens

<400> SEQUENCE: 54

Pro Gln Pro Glu Leu Pro Tyr Pro Gln Pro Glu Leu Pro Tyr
1               5                   10

<210> SEQ ID NO 55
<211> LENGTH: 19
<212> TYPE: PRT
<213> ORGANISM: Homo sapiens

<400> SEQUENCE: 55

Leu Gly Gln Gln Gln Pro Phe Pro Pro Gln Gln Pro Tyr Pro Gln Pro
1               5                   10                  15

Gln Pro Phe

<210> SEQ ID NO 56
<211> LENGTH: 18
<212> TYPE: PRT
<213> ORGANISM: Homo sapiens

<400> SEQUENCE: 56

Gln Gln Tyr Pro Ser Gly Glu Gly Ser Phe Gln Pro Ser Gln Glu Asn
1               5                   10                  15

Pro Gln

<210> SEQ ID NO 57
<211> LENGTH: 15
<212> TYPE: PRT
<213> ORGANISM: Homo sapiens

<400> SEQUENCE: 57

Gly Gln Gln Gly Tyr Tyr Pro Thr Ser Pro Gln Gln Ser Gly Gln
1               5                   10                  15

<210> SEQ ID NO 58
<211> LENGTH: 17
<212> TYPE: PRT
<213> ORGANISM: Homo sapiens

<400> SEQUENCE: 58

Gln Leu Gln Pro Phe Pro Gln Pro Glu Leu Pro Tyr Pro Gln Pro Gln
1               5                   10                  15

Ser

<210> SEQ ID NO 59
<211> LENGTH: 17
<212> TYPE: PRT
<213> ORGANISM: Homo sapiens

<400> SEQUENCE: 59

Pro Gln Leu Pro Tyr Pro Gln Pro Glu Leu Pro Tyr Pro Gln Pro Gln
1               5                   10                  15
```

Pro

<210> SEQ ID NO 60
<211> LENGTH: 11
<212> TYPE: PRT
<213> ORGANISM: Homo sapiens

<400> SEQUENCE: 60

```
Pro Phe Pro Gln Pro Glu Leu Pro Tyr Pro Gln
1               5                   10
```

<210> SEQ ID NO 61
<211> LENGTH: 14
<212> TYPE: PRT
<213> ORGANISM: Homo sapiens

<400> SEQUENCE: 61

```
Pro Arg Ala Pro Trp Ile Glu Gln Glu Gly Pro Glu Tyr Trp
1               5                   10
```

<210> SEQ ID NO 62
<211> LENGTH: 16
<212> TYPE: PRT
<213> ORGANISM: Homo sapiens

<400> SEQUENCE: 62

```
Ile Asp Val Trp Leu Gly Gly Leu Leu Ala Glu Asn Phe Leu Pro Tyr
1               5                   10                  15
```

<210> SEQ ID NO 63
<211> LENGTH: 12
<212> TYPE: PRT
<213> ORGANISM: Homo sapiens

<400> SEQUENCE: 63

```
Gln Leu Gln Pro Phe Pro Gln Pro Glu Leu Pro Tyr
1               5                   10
```

<210> SEQ ID NO 64
<211> LENGTH: 17
<212> TYPE: PRT
<213> ORGANISM: Homo sapiens

<400> SEQUENCE: 64

```
Pro Gln Pro Gln Pro Phe Pro Pro Glu Leu Pro Tyr Pro Gln Pro Gln
1               5                   10                  15
```

Ser

<210> SEQ ID NO 65
<211> LENGTH: 17
<212> TYPE: PRT
<213> ORGANISM: Homo sapiens

<400> SEQUENCE: 65

```
Gln Leu Gln Pro Phe Leu Gln Pro Glu Leu Pro Tyr Ser Gln Pro Gln
1               5                   10                  15
```

Pro

<210> SEQ ID NO 66
<211> LENGTH: 17
<212> TYPE: PRT
<213> ORGANISM: Homo sapiens

```
<400> SEQUENCE: 66

Gln Pro Gln Pro Phe Pro Pro Glu Leu Pro Tyr Pro Gln Thr Gln
1               5                   10                  15

Pro

<210> SEQ ID NO 67
<211> LENGTH: 17
<212> TYPE: PRT
<213> ORGANISM: Homo sapiens

<400> SEQUENCE: 67

Pro Gln Pro Gln Pro Phe Pro Pro Glu Leu Pro Tyr Pro Gln Thr Gln
1               5                   10                  15

Pro

<210> SEQ ID NO 68
<211> LENGTH: 17
<212> TYPE: PRT
<213> ORGANISM: Homo sapiens

<400> SEQUENCE: 68

Gln Leu Gln Pro Phe Pro Gln Pro Glu Leu Ser Tyr Ser Gln Pro Gln
1               5                   10                  15

Pro

<210> SEQ ID NO 69
<211> LENGTH: 17
<212> TYPE: PRT
<213> ORGANISM: Homo sapiens

<400> SEQUENCE: 69

Gln Leu Gln Pro Phe Pro Gln Pro Glu Leu Pro Tyr Ser Gln Pro Gln
1               5                   10                  15

Pro

<210> SEQ ID NO 70
<211> LENGTH: 17
<212> TYPE: PRT
<213> ORGANISM: Homo sapiens

<400> SEQUENCE: 70

Pro Gln Pro Gln Pro Phe Pro Pro Glu Leu Pro Tyr Pro Gln Pro Gln
1               5                   10                  15

Ser

<210> SEQ ID NO 71
<211> LENGTH: 17
<212> TYPE: PRT
<213> ORGANISM: Homo sapiens

<400> SEQUENCE: 71

Gln Leu Gln Pro Phe Leu Gln Pro Glu Leu Pro Tyr Ser Gln Pro Gln
1               5                   10                  15

Pro

<210> SEQ ID NO 72
<211> LENGTH: 17
<212> TYPE: PRT
<213> ORGANISM: Homo sapiens

<400> SEQUENCE: 72
```

```
Gln Pro Gln Pro Phe Pro Pro Pro Glu Leu Pro Tyr Pro Gln Thr Gln
1               5                   10                  15

Pro

<210> SEQ ID NO 73
<211> LENGTH: 17
<212> TYPE: PRT
<213> ORGANISM: Homo sapiens

<400> SEQUENCE: 73

Pro Gln Pro Gln Pro Phe Pro Pro Glu Leu Pro Tyr Pro Gln Thr Gln
1               5                   10                  15

Pro

<210> SEQ ID NO 74
<211> LENGTH: 17
<212> TYPE: PRT
<213> ORGANISM: Homo sapiens

<400> SEQUENCE: 74

Gln Leu Gln Pro Phe Pro Gln Pro Glu Leu Ser Tyr Ser Gln Pro Gln
1               5                   10                  15

Pro

<210> SEQ ID NO 75
<211> LENGTH: 17
<212> TYPE: PRT
<213> ORGANISM: Homo sapiens

<400> SEQUENCE: 75

Gln Leu Gln Pro Phe Pro Gln Pro Glu Leu Pro Tyr Ser Gln Pro Gln
1               5                   10                  15

Pro

<210> SEQ ID NO 76
<211> LENGTH: 17
<212> TYPE: PRT
<213> ORGANISM: Homo sapiens

<400> SEQUENCE: 76

Gln Leu Gln Pro Phe Leu Gln Pro Glu Leu Pro Tyr Ser Gln Pro Gln
1               5                   10                  15

Pro

<210> SEQ ID NO 77
<211> LENGTH: 17
<212> TYPE: PRT
<213> ORGANISM: Homo sapiens

<400> SEQUENCE: 77

Pro Gln Pro Gln Pro Phe Leu Pro Glu Leu Pro Tyr Pro Gln Pro Gln
1               5                   10                  15

Ser

<210> SEQ ID NO 78
<211> LENGTH: 17
<212> TYPE: PRT
<213> ORGANISM: Homo sapiens

<400> SEQUENCE: 78
```

```
-continued
Pro Gln Pro Gln Pro Phe Pro Pro Glu Leu Pro Tyr Pro Gln Pro Pro
1               5                   10                  15
Pro
```